(12) United States Patent
Nagatsuka et al.

(10) Patent No.: US 8,995,614 B2
(45) Date of Patent: Mar. 31, 2015

(54) METHOD FOR DISPLAYING MEDICAL IMAGES AND MEDICAL IMAGE DISPLAY SYSTEM

(75) Inventors: Sumiya Nagatsuka, Hino (JP); Junko Kiyohara, Hino (JP); Shikou Kaneko, Tokorozawa (JP)

(73) Assignee: Konica Minolta Medical & Graphic, Inc. (JP)

( * ) Notice: Subject to any disclaimer, the term of this patent is extended or adjusted under 35 U.S.C. 154(b) by 176 days.

(21) Appl. No.: 13/876,936

(22) PCT Filed: Mar. 7, 2011

(86) PCT No.: PCT/JP2011/055211
§ 371 (c)(1),
(2), (4) Date: Mar. 29, 2013

(87) PCT Pub. No.: WO2012/042924
PCT Pub. Date: Apr. 5, 2012

(65) Prior Publication Data
US 2013/0201198 A1    Aug. 8, 2013

(30) Foreign Application Priority Data

Sep. 29, 2010   (JP) .................................. 2010-219031

(51) Int. Cl.
*H05G 1/64*     (2006.01)
*G09G 5/00*     (2006.01)
*A61B 6/00*     (2006.01)

(52) U.S. Cl.
CPC ................ *G09G 5/003* (2013.01); *A61B 6/463* (2013.01); *A61B 6/484* (2013.01); *A61B 6/5235* (2013.01)
USPC .......................................................... 378/62

(58) Field of Classification Search
USPC ................................. 378/62, 68, 98; 345/581
See application file for complete search history.

(56) References Cited

U.S. PATENT DOCUMENTS

| 7,889,838 B2 * | 2/2011 | David et al. ..................... 378/36 |
| 2010/0220832 A1 * | 9/2010 | Ning et al. ........................ 378/4 |
| 2010/0290590 A1 * | 11/2010 | Ouchi et al. .................... 378/62 |

FOREIGN PATENT DOCUMENTS

| JP | 2003-284690 A | 10/2003 |
| JP | 2003-284707 A | 10/2003 |
| JP | 2009-150875 A | 7/2009 |
| JP | 2010-502977 A | 1/2010 |
| WO | 2008/102632 A1 | 8/2008 |

OTHER PUBLICATIONS

International Preliminary Report on Patentability for International Application No. PCT/JP2011/055211, issued Apr. 16, 2013, with English translation.
International Search Report for International application No. PCT/JP2011/055211, Apr. 22, 2011, with English translation.

* cited by examiner

*Primary Examiner* — Irakli Kiknadze
(74) *Attorney, Agent, or Firm* — Cantor Colburn LLP

(57) ABSTRACT

The present invention provides a method for displaying medical images and a medical image display system that do not require a medical practitioner to move his/her line of sight at the time of comparing/interpreting images and that can improve accuracy in diagnosis. According to the medical image display system of the present invention: an X-ray imaging device captures an image of a subject according to a first imaging mode by a fringe-scanning imaging device or a second imaging mode by a Fourier transform imaging device; a controller creates at least two images from among an X-ray absorption image, a differential phase image, and a small-angle scattering image on the basis of the captured moir image; and said at least two images that have been created are displayed in turn in the same position on a display section.

3 Claims, 40 Drawing Sheets

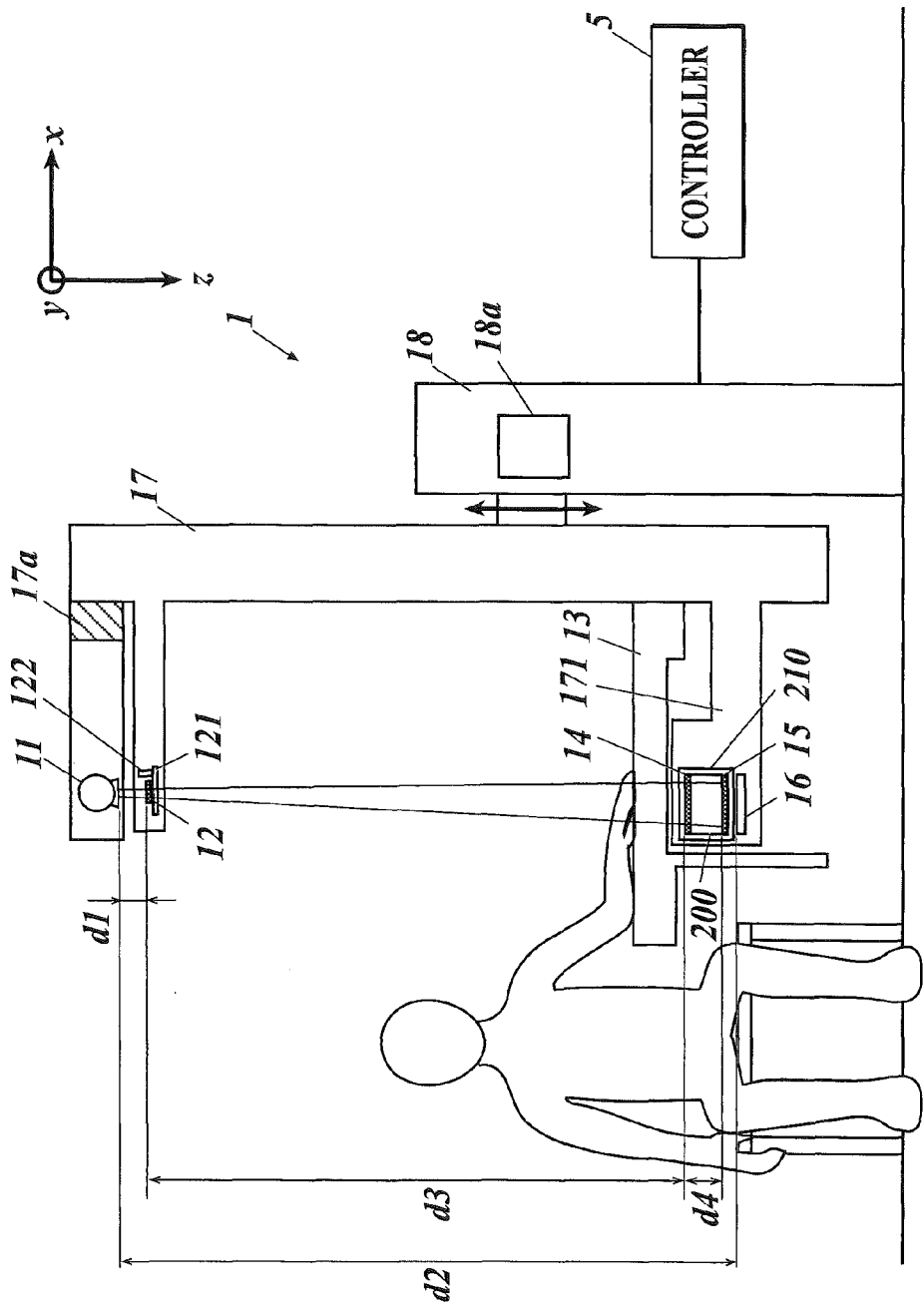

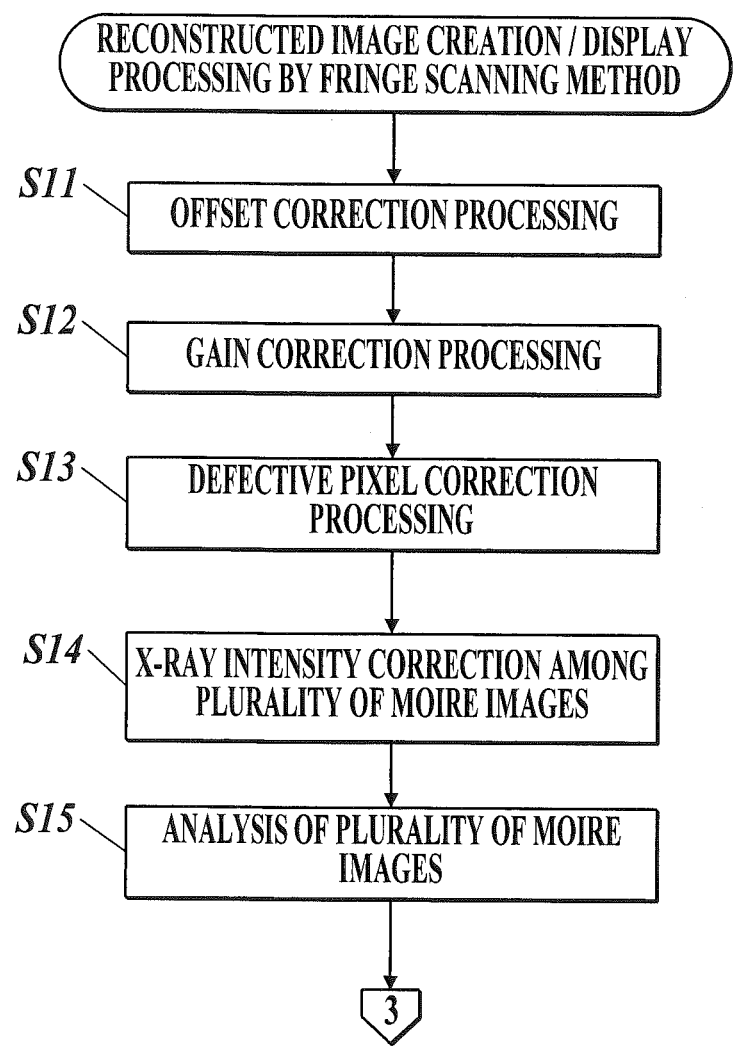

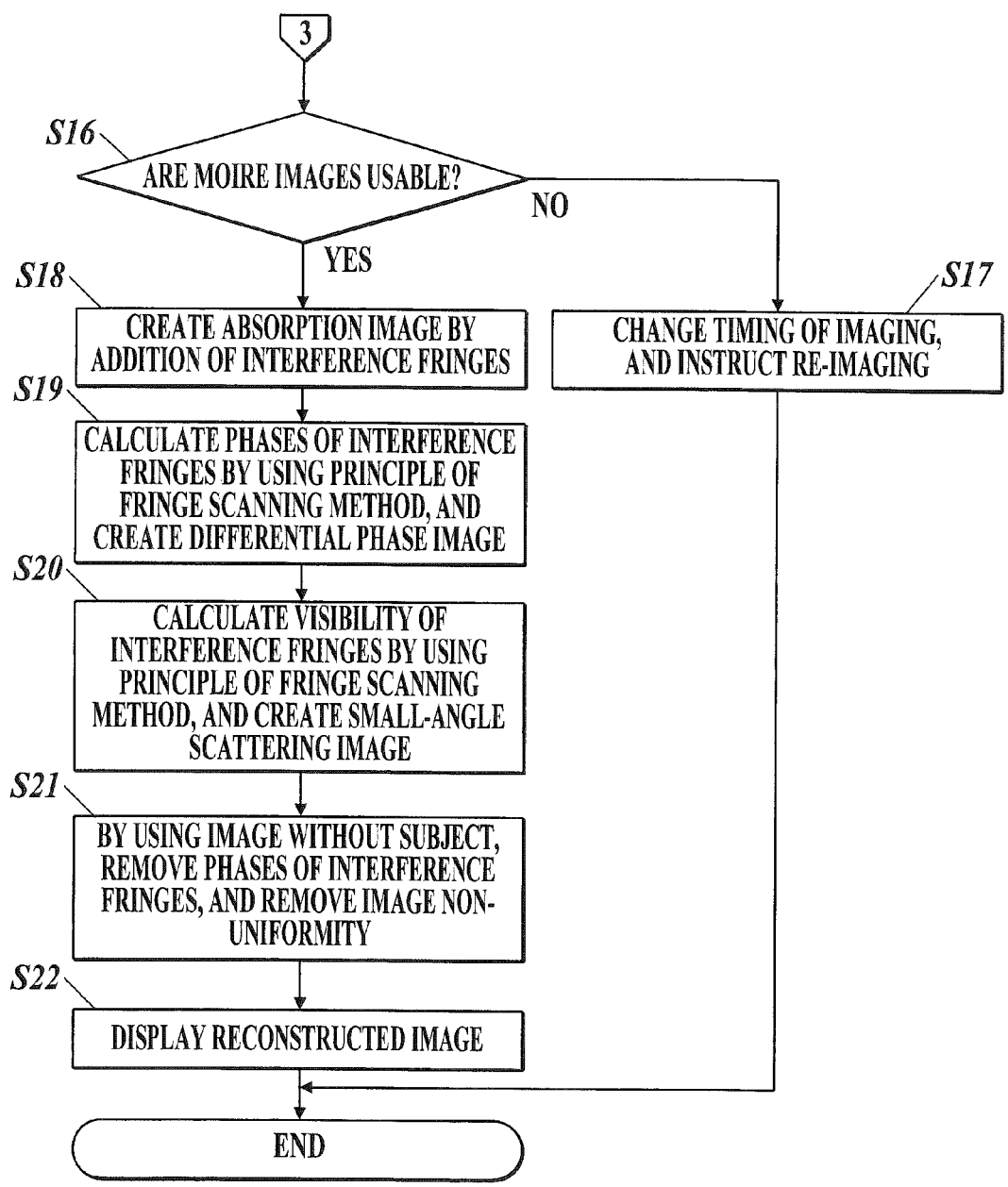

○ VALUE WHEN FEEDING AMOUNT IS CONSTANT
● VALUE WHEN THERE IS DEVIATION IN FEEDING AMOUNT

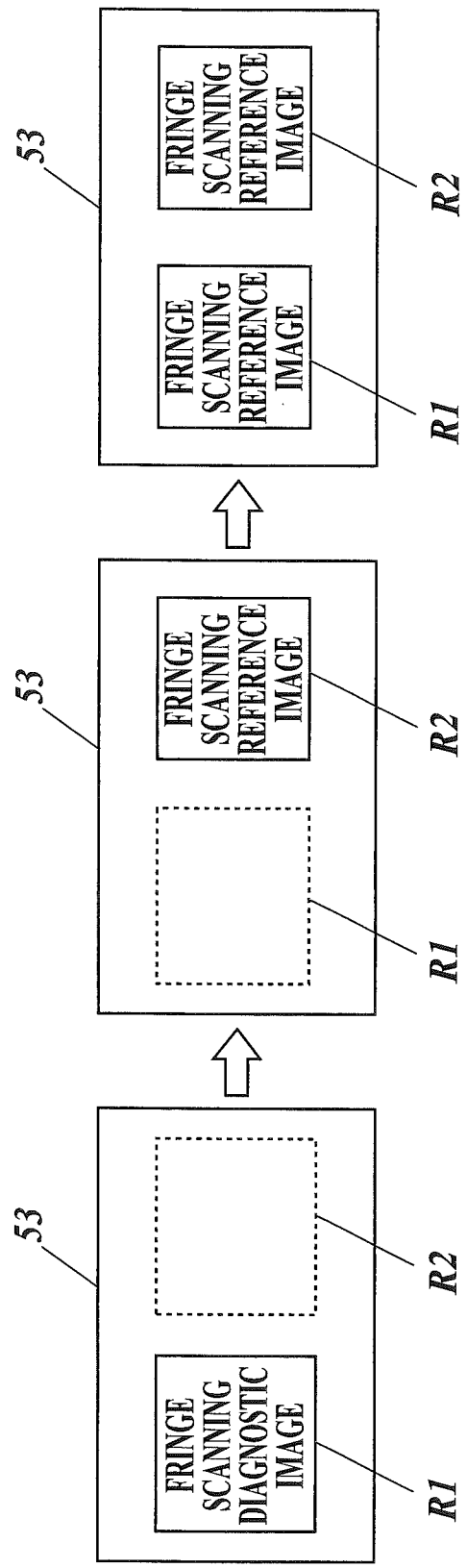

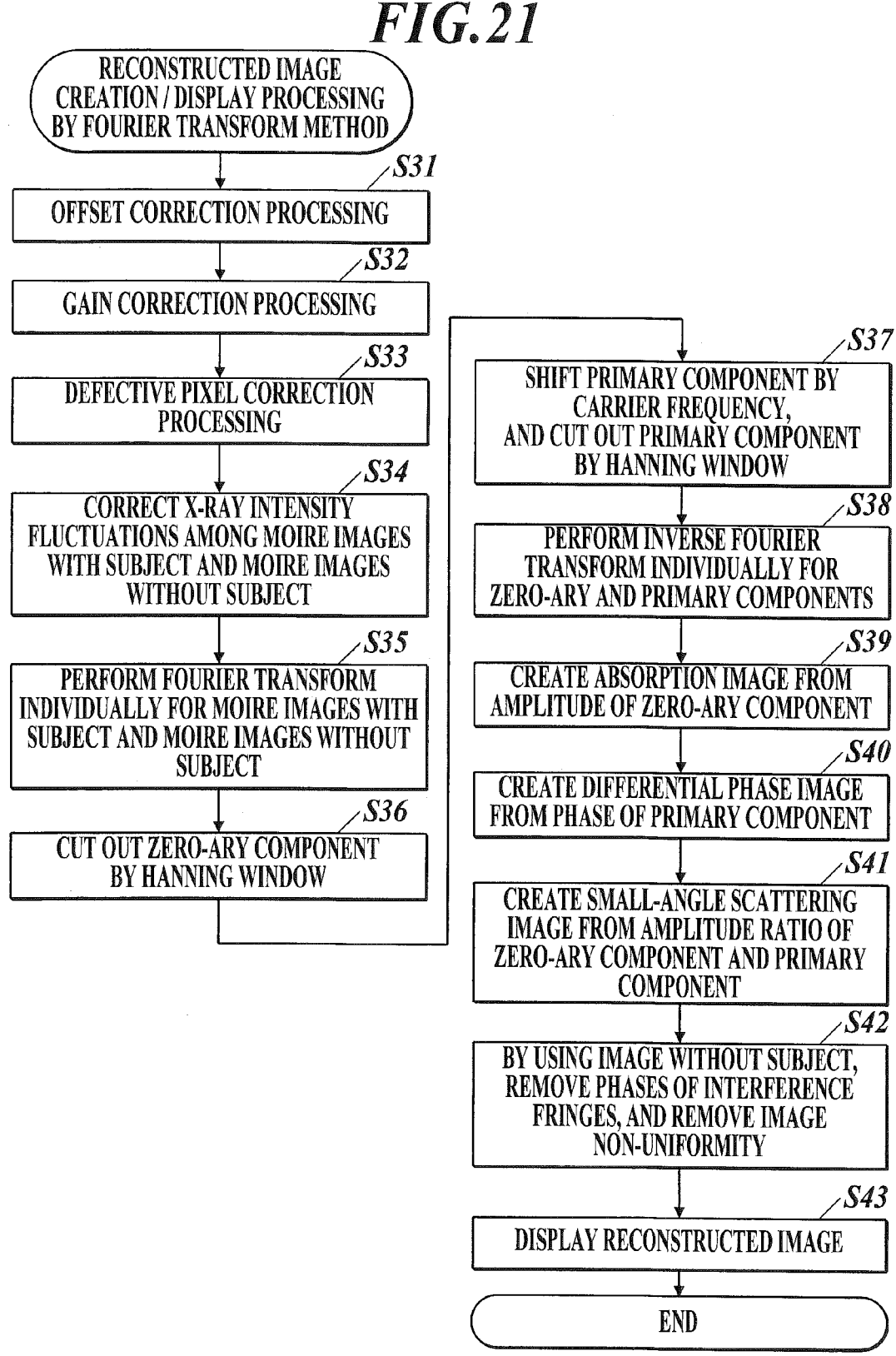

FIG.26
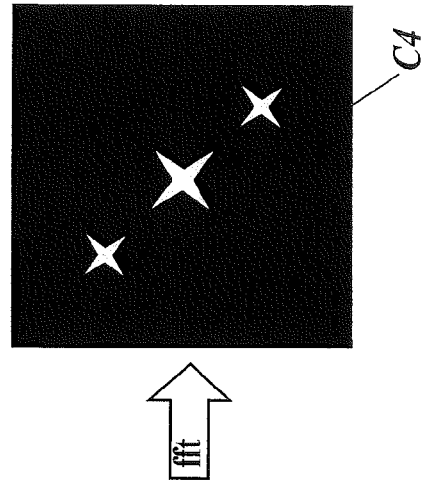
INTERFERENCE FRINGES FOR
FOURIER TRANSFORM METHOD
: DIAGONAL — C3
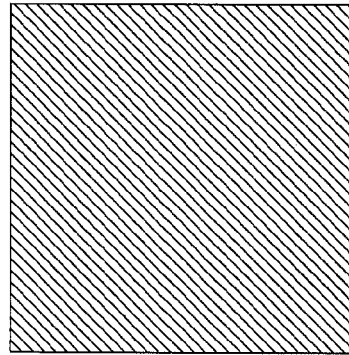
INTERFERENCE FRINGES FOR
FRINGE SCANNING METHOD
: DIAGONAL — C2
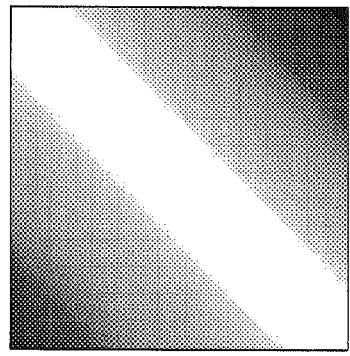
ORIENTATION OF GRATING
: DIAGONAL — C1

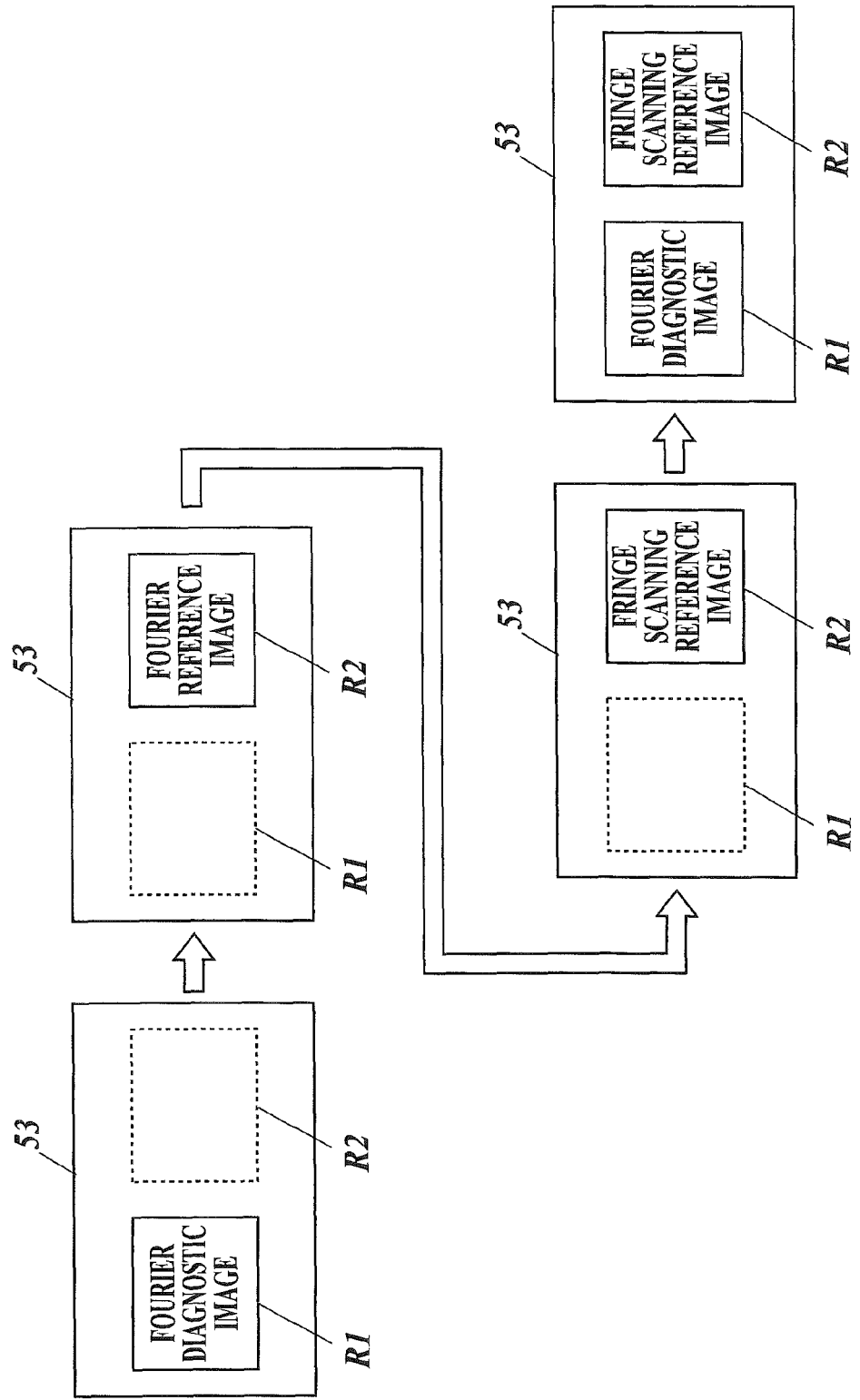

METHOD FOR DISPLAYING MEDICAL IMAGES AND MEDICAL IMAGE DISPLAY SYSTEM

This is the U.S. national stage of application No. PCT/JP2011/055211, filed on Mar. 7, 2011. Priority under 35 U.S.C. §119 (a) and 35 U.S.C. §365 (b) is claimed from Japanese Application No. 2010-219031 filed Sep. 29, 2010, the disclosure of which is also incorporated herein by reference.

TECHNICAL FIELD

The present invention relates to a medical image display method and a medical image display system.

BACKGROUND ART

Most of medical X-ray images for use in a diagnosis are images by the absorption contrast method. The absorption contrast method forms a contrast by an attenuation difference in X-ray intensity when an X-ray transmits through a subject. Meanwhile, the phase contrast method is proposed, which obtains the contrast not by the absorption of the X-ray but by a phase change of the X-ray. For example, phase contrast imaging is performed, which obtains an X-ray image with high visibility by edge enhancement using refraction of the X-ray at the time of magnification imaging (for example, refer to Patent Literatures 1 and 2).

The absorption contrast method is effective for imaging of a subject such as a bone, in which the absorption of the X-ray is large. As opposed to this, the phase contrast method is capable of also imaging a mammary tissue, an articular cartilage, and a soft tissue on the periphery of a joint, which have small X-ray absorption differences and are less likely to appear as images by the absorption contrast method, and is expected to be applied to the x-ray image diagnosis.

As a device for the phase contrast imaging, the Talbot interferometer using the Talbot effect is also examined (for example, Patent Literatures 3 to 5). The Talbot effect refers to a phenomenon that, when coherent light transmits through a first grating in which slits are provided in a constant cycle, a grating image of the light is formed in the constant cycle in a traveling direction thereof. This grating image is called a self-image, and the Talbot interferometer arranges a second grating at a position where the self-image is formed, and measures interference fringes generated by slightly shifting the second grating. When an object is arranged in front of the second grating, moire is disturbed. Accordingly, if X-ray imaging is performed by the Talbot interferometer, then the subject is arranged in front of the first grating, a coherent X-ray is irradiated thereonto, and a moire image thus obtained is arithmetically operated, whereby it is possible to obtain a reconstructed image of the subject.

Moreover, a Talbot-Lau interferometer is also proposed, which places a multi-slit between an X-ray source and the first grating, and increases an exposure dose of the X-ray (for example, refer to Patent Literature 6). The conventional Talbot-Lau interferometer is a meter that images a plurality of moire images at a constant cycle interval while moving the first grating or the second grating (while relatively moving both of the gratings), and the multi-slit is provided in order to increase an X-ray dose.

Moreover, in Japanese Patent Application No. 2009-214483 (PCT/JP2010/53978), the applicant of this application has filed a system in the Talbot-Lau interferometer, which enables scanning with good machine accuracy by moving the multi-slit with respect to the first grating and the second grating, and is capable of obtaining a high-definition image. Furthermore, in Japanese Patent Application No. 2010-061993 (PCT/JP2011/053904), the applicant of this application has filed a system in the Talbot-Lau interferometer, which is capable of obtaining the high-definition image.

As a method of creating the reconstructed image from the moire image, a method of creating the reconstructed image from one moire image by using the Fourier transform method is also known (for example, refer to Non-Patent Literature 1), as well as such methods as mentioned above, each of which creates the reconstructed image by the fringe scanning method from the plurality of moire images at the constant cycle interval, which are obtained by the Talbot interferometer or the Talbot-Lau interferometer. In comparison with the reconstructed image obtained by the fringe scanning method, in the reconstructed image obtained by the Fourier transform method, a spatial resolution thereof is inferior; however, the Fourier transform method does not require the plurality of moire images as the fringe scanning method requires. Therefore, reduction of an imaging time can be achieved, and suppression of an influence of a body motion of the subject at intervals among plural times of the imaging can be achieved. Moreover, mechanical operations at the time of the imaging are eliminated, and accordingly, a false image owing to an error of a feeding mechanism for the grating or the multi-slit is also eliminated.

Incidentally, in the case of following up one patient by using the X-ray images, the following operations are frequently performed, which perform the imaging at the same positioning and the same imaging conditions as those for the past image of the patient concerned, and array and display both of such a diagnostic image imaged this time and the past image so that a physician can be facilitated to compare both with each other and interpret the same (for example, refer to Patent Literature 7).

Moreover, at the time of diagnosing the existence of a certain lesion, for example, the existence of a tumor, a cancer, or calcification in the mamma, the following operation is also performed, which arrays and displays a typical case image, a teaching image, a normal image and the like with regard to a suspected lesion together with the X-ray image of the patient as a diagnosis target, and thereby enhances diagnostic accuracy.

An extent to which the diagnostic accuracy is enhanced when a reference image such as the past image and the case image is arranged at a best position with respect to the diagnostic image differs depending on a type of the lesion. Moreover, in some case, the reference image to be taken as a comparison target is plural. In any case, on a display screen, the diagnostic image and the reference image are displayed in parallel while being physically apart from each other. Accordingly, in the case of performing such comparison and interpretation, a line of sight is moved left and right or up and down between the diagnostic image and the reference image, a movement of the line of sight is increased, and this causes a fatigue. Moreover, every time of moving the line of sight between the respective images, the physician must make a diagnosis while paying attention to a positional relationship in region of interest between the images, and this is also a cause of the fatigue.

Accordingly, in order to reduce the movement of the line of sight at the time of the comparison and the interpretation, there is proposed a technology for repeatedly displaying such a comparison target image on a screen of one display means at a display speed ranging from one frame to five frames per second (for example, refer to Patent Literature 8).

PRIOR ART LITERATURES

Patent Literatures

Patent Literature 1: Japanese Patent Laid-Open Publication No. 2007-268033
Patent Literature 2: Japanese Patent Laid-Open Publication No. 2008-18060
Patent Literature 3: Japanese Patent Laid-Open Publication No. S58-16216
Patent Literature 4: Pamphlet of International Publication No. 2004/058070
Patent Literature 5: Japanese Patent Laid-Open Publication No. 2007-203063
Patent Literature 6: Pamphlet of International Publication No. 2008/102898
Patent Literature 7: Japanese Patent Laid-Open Publication No. 2010-51523
Patent Literature 8: Japanese Patent Laid-Open Publication No. 2006-006435

Non-Patent Literature

Non-Patent Literature 1: M. Takeda, H. Ina, and S. Kobayashi, "Fourier-Transform Method of Fringe-Pattern Analysis for Computer-Based Topography and Interferometry" J. Opt. Soc. Am. 72, 156 (1982)
Non-Patent Literature 2: Asaharu YAMADA and Shunsuke YOKOZEKI, "Moire Fringe/Interference Fringe Application Measurement Method (original title is in Japanese)", Corona Publishing Co., Ltd., Dec. 10, 1996

SUMMARY OF THE INVENTION

Problem to be solved by the Invention

In the technology described in Patent Literature 8, processing for aligning positions of subject regions or regions of interest of the respective displayed images with each other becomes essential. However, it is technically impossible to set accuracy of such positional alignment at 100%, and it is conceived possible that a lack of accuracy of the positional alignment may eventually lead to a decrease of diagnostic efficiency and a wrong diagnosis.

It is an object of the present invention to provide a medical image display method and a medical image display system, each of which eliminates the movement of the physician's line of sight at the time of the comparison and the interpretation, and is capable of enhancing the diagnostic accuracy.

Means for Solving the Problem

To solve the above mentioned problems, according to a first aspect of the present invention, there is provided a medical image display method including:
an imaging step of imaging a subject by a fringe scanning-type imaging apparatus or a Fourier transform-type imaging apparatus, the apparatus including an X-ray source that irradiates an X-ray, a first grating and a second grating, each of which is composed in such a manner that a plurality of slits are arrayed in a direction perpendicular to an irradiation axis direction of the X-ray, a subject platform, and an X-ray detector in which conversion elements generating electric signals in response to the irradiated X-ray are arranged two-dimensionally, the X-ray detector reading, as image signals, the electric signals generated by the conversion elements;
an image processing step of creating at least two images of an X-ray absorption image, a differential phase image and a small-angle scattering image by an image processing unit based on the image signals of the subject, the imaging signals being obtained in the imaging step; and
a display step of displaying the at least two images created by the image processing step on the same position of a display unit while sequentially switching the at least two images.

Preferably, in the imaging step, the fringe scanning-type imaging apparatus relatively moves the first grating and the second grating, and repeats processing for allowing the X-ray detector to read the image signals in response to the X-ray irradiated by the X-ray source, every time when the first grating and the second grating move at a constant cycle interval, thereby creates a plurality of moire images at the constant cycle interval, and
in the image processing step, the image processing unit creates the at least two images of the X-ray absorption image, the differential phase image and the small-angle scattering image based on the moire images at the constant cycle interval.

Preferably, the fringe scanning type-imaging apparatus further includes a multi-slit having a plurality of slits arrayed in a direction perpendicular to the irradiation axis direction of the X-ray,
in the imaging step, the fringe scanning type-imaging apparatus relatively moves the multi-slit with respect to the first grating and the second grating, and repeats processing for allowing the X-ray detector to read the image signals in response to the X-ray irradiated by the X-ray source, every time when the multi-slit moves at a constant cycle interval, thereby creates a plurality of moire images at the constant cycle interval, and
in the image processing step, the image processing unit creates the at least two images of the X-ray absorption image, the differential phase image and the small-angle scattering image based on the moire images at the constant cycle interval.

Preferably, the imaging step performs imaging while mounting the subject on the subject platform, in addition, performs imaging without mounting the subject on the subject platform, and obtains moire images with the subject and moire images without the subject, and
the image processing step creates at least two images of an X-ray absorption image, a differential phase image and a small-angle scattering image based on the moire images with the subject, the moire images being obtained in the imaging step, creates same types of images without the subject as the at least two created images with the subject based on the moire images without the subject, the moire images being obtained in the imaging step, and corrects the images with the subject by using the images without the subject.

Preferably, before or after the at least two images created by the image processing step are displayed on the same position of the display unit while being sequentially switched, the display step displays at least two reference images of an X-ray absorption image, a differential phase image and a small-angle scattering image, the reference images being to be referred to in an event of interpreting the at least two images, on the same position of the display unit, the position being different from the position of the two images to be interpreted, while sequentially switching the at least two reference images.

According to a second aspect of the present invention, there is provided a medical image display system including:
a fringe scanning-type imaging apparatus or a Fourier transform-type imaging apparatus, either of the apparatuses including:

an X-ray source that irradiates an X-ray;

a first grating and a second grating, each of which is composed in such a manner that a plurality of slits are arrayed in a direction perpendicular to an irradiation axis direction of the X-ray;

a subject platform; and an X-ray detector in which conversion elements generating electric signals in response to the irradiated X-ray are arranged two-dimensionally, the X-ray detector reading, as image signals, the electric signals generated by the conversion elements; and image processing unit which creates at least two of an X-ray absorption image, differential phase image and small-angle scattering image of a subject, the subject being imaged by either of the imaging apparatuses, based on image signals of the subject;

display unit which displays the images created by the image processing unit; and control unit which displays the at least two images on the same position of the display unit while sequentially switching the at least two images, the at least two images being created by the image processing unit.

Preferably, the control unit displays the at least two images on the display unit while sequentially switching the at least two images at every predetermined time.

Preferably, the fringe scanning-type imaging apparatus is a Talbot-Lau interferometer that includes a multi-slit arranged in a vicinity of the X-ray source, and relatively moves the multi-slit with respect to the first grating and the second grating.

Advantageous Effect of the Invention

In accordance with the present invention, it is made possible to provide the medical image display method and the medical image display system, each of which eliminates the movement of the physician's line of sight at the time of the comparison and the interpretation, and is capable of enhancing the diagnostic accuracy.

BRIEF DESCRIPTION OF THE DRAWINGS

FIG. 1 is a view showing a medical image display system (including a side view of an X-ray imaging apparatus) according to this embodiment.

FIG. 14A is a flowchart showing reconstructed image creation/display processing by a fringe scanning method to be executed by a control unit of a controller.

FIG. 14B is a flowchart showing the reconstructed image creation/display processing by the fringe scanning method to be executed by the control unit of the controller.

FIG. 20 is a view showing another example of the display method in a case of displaying a reference image in combination in the event of displaying the reconstructed image on the display unit in Step S22 of FIG. 14B.

FIG. 21 is a flowchart showing reconstructed image creation/display processing by a Fourier transform method to be executed by the control unit of the controller.

FIG. 26 is a view showing a grating direction when the slit direction of the grating is arranged diagonally, interference fringes imaged in the first imaging mode, interference fringes imaged in the second imaging mode, and a result of performing the Fourier transform for the interference fringes imaged in the second imaging mode.

FIG. 31 is a view showing another example of the display method in the case of displaying the reference image in combination in the event of displaying the reconstructed image on the display unit in Step S43 of FIG. 21.

BEST MODE FOR CARRYING OUT THE INVENTION

Figure 2A:
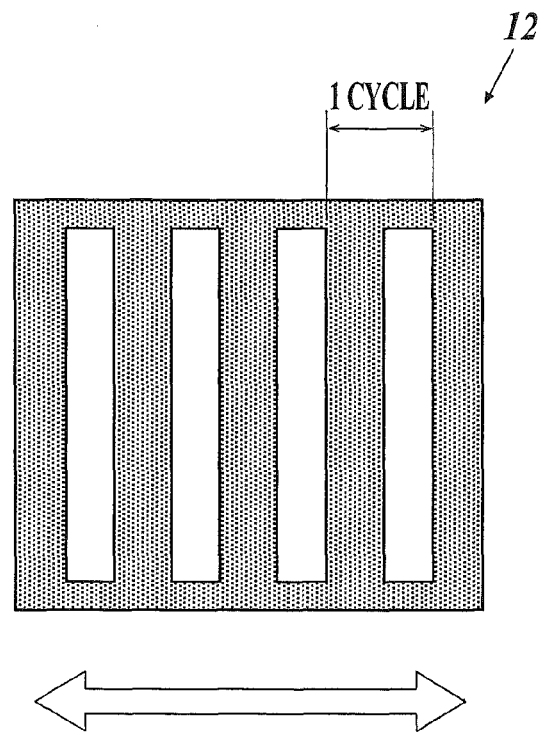
FIG. 2A is a plan view of a multi-slit.

A description is made below of embodiments of the present invention with reference to the drawings.

FIG. 1 shows a medical image display system according to this embodiment. The medical image display system includes: an X-ray imaging apparatus 1; and a controller 5. The X-ray imaging apparatus 1 is an apparatus that has: a first imaging mode where the X-ray imaging apparatus 1 concerned functions as a fringe scanning-type imaging apparatus; and a second imaging mode where the X-ray imaging apparatus 1 concerned functions as a Fourier transform-type imaging apparatus. The fringe scanning-type imaging apparatus is an apparatus that, for use in a reconstructed image by the fringe scanning method, performs imaging in a plurality of steps by a Talbot-Lau interferometer, and creates a plurality of moire images. The Fourier transform-type imaging apparatus is an apparatus that, for use in a reconstructed image by the Fourier transform method, performs imaging in one or two directions, and creates one or more moire images.

In this embodiment, the X-ray imaging apparatus 1 is described to be an apparatus that images the hand and the fingers, which are a subject; however, is not limited to this.

As shown in FIG. 1, the X-ray imaging apparatus includes an X-ray source 11, a multi-slit 12, a subject platform 13, a first grating 14, a second grating 15, an X-ray detector 16, a holding portion 17, a main body section 18 and the like. The X-ray imaging apparatus 1 is a longitudinal-type one, and the X-ray source 11, the multi-slit 12, the subject platform 13, the first grating 14, the second grating 15 and the X-ray detector 16 are arranged in this order in a z-direction as the direction of gravity. A distance between a focal point of the X-ray source 11 and the multi-slit 12 is represented as d1 (mm), a distance between the focal point of the X-ray source 11 and the X-ray detector 16 is represented as d2 (mm), a distance between the multi-slit 12 and the first grating 14 is represented as d3 (mm), and a distance between the first grating 14 and the second grating 15 is represented as d4 (mm).

The distance d1 is preferably 5 to 500 (mm), more preferably, 5 to 300 (mm).

In general, a height of an imaging room of a radiology department is approximately 3 (m) or less, and accordingly, the distance d2 is preferably at least 3000 (mm) or less. In particular, the distance d2 is preferably 400 to 2500 (mm), more preferably, 500 to 2000 (mm).

A distance (d1+d3) between the focal point of the X-ray source 11 and the first grating 14 is preferably 300 to 5000 (mm), more preferably, 400 to 1800 (mm).

A distance (d1+d3+d4) between the focal point of the X-ray source 11 and the second grating 15 is preferably 400 to 5000 (mm), more preferably, 500 to 2000 (mm).

With regard to each of the distances, an optimum distance where a grating image (self-image) by the first grating 14 overlaps the second grating 15 just needs to be calculated and set from a wavelength of an X-ray to be irradiated from the X-ray source 11.

The X-ray source 11, the multi-slit 12, the subject platform 13, the first grating 14 and the second grating 15 and the X-ray detector 16 are held integrally by the same holding portion 17, and positional relationships thereamong in the z-direction are fixed. The holding portion 17 is formed into a C-shaped arm form, and is attached to the main body section 18 so as to be capable of moving (ascending/descending) in the z-direction by a drive unit 18a provided in the main body section 18.

The X-ray source 11 is held through a cushioning member 17a. For the cushioning member 17a, any material can be used as long as the material can absorb impact and vibrations, and for example, elastomer and the like can be mentioned. The X-ray source 11 generates heat by the irradiation of the X-ray, and accordingly, it is preferable that the cushioning member 17a on the X-ray source 11 side be formed of a heat insulating material in addition.

The X-ray source 11 includes an X-ray tube, generates the X-ray by the X-ray tube concerned, and irradiates the X-ray in the z-direction (the direction of gravity). As the X-ray tube, for example, a Coolidge X-ray tube or a rotating anode X-ray tube, which is widely used in general in the medical field, can be used. As an anode, tungsten or molybdenum can be used.

A focal point diameter of the X-ray is preferably 0.03 to 3 (mm), more preferably, 0.1 to 1 (mm).

The multi-slit 12 is a diffraction grating, in which a plurality of slits is arrayed and provided at a predetermined interval as shown in FIG. 2A. The plurality of slits is arrayed in a direction (shown by a white arrow in FIG. 2A) perpendicular to an X-ray irradiation axis direction (the z-direction of FIG. 1). The multi-slit 12 is formed of a material such as tungsten, lead and gold, which has a large X-ray shielding capability, that is, has a high X-ray absorptivity, on a substrate of a material such as silicon and glass, which has a low X-ray absorptivity. For example, by photolithography, a resist layer is masked in a slit pattern, and ultraviolet rays (UV) are irradiated thereonto, whereby the slit pattern is transferred to the resist layer. Slit structures, which have the same shape as that of the pattern concerned, are obtained by exposure, and metal is embedded among the slit structures by electroforming, whereby the multi-slit 12 is formed.

A slit cycle of the multi-slit 12 is 1 to 60 (μm). With regard to the slit cycle, a distance between such slits adjacent to each other is defined as one cycle as shown in FIG. 2A. A width (a length of each slit in a slit array direction) of each slit is a length of 1 to 60 (%) of the slit cycle, preferably, 10 to 40 (%) thereof. A height (a height in the z-direction) of each slit is 1 to 500 (μm), preferably, 1 to 150 (μm).

When the slit cycle of the multi-slit 12 is $w_0$ (μm), and the slit cycle of the first grating 14 is $w_1$ (μm), then the slit cycle $w_0$ can be obtained by the following expression:

$$w_0 = w_1 \cdot (d3 + d4)/d4$$

The cycle $w_0$ is decided so as to satisfy the expression concerned, whereby self-images, which are formed of X-rays having passed through the slits of the multi-slit 12 and the slits of the first grating 14, overlap each other on the second grating 15, and can be brought into a so-called focused state.

Figure 2B:
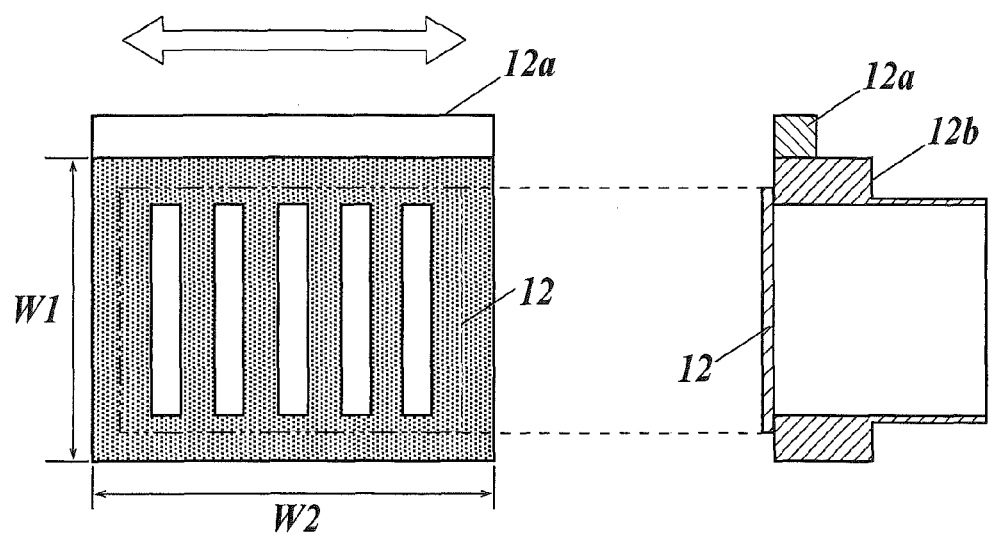
FIG. 2B is a plan view and side view of a state where the multi-slit is held on a holder.

As shown in FIG. 2B, the multi-slit 12 is held in a holder 12b including a rack 12a. The rack 12a is provided in a slit arraying direction of the multi-slit 12. The rack 12a is a portion, which is engaged with a pinion 122c of a drive unit 122 to be described later, and moves the multi-slit 12, which is held in the holder 12b, in the slit arraying direction in response to rotation (a phase angle) of the pinion 122c.

In this embodiment, in the X-ray imaging apparatus 1, a multi-slit rotating unit 121 and the drive unit 122 are provided. The multi-slit rotating unit 121 is a mechanism for rotating the multi-slit 12 about the X-ray irradiation axis in response to rotations of the first grating 14 and the second grating 15 about the X-ray irradiation axis. The drive unit 122 is a mechanism for moving the multi-slit 12 in the slit arraying direction for the purpose of the imaging of the plurality of moire images.

Figure 3:
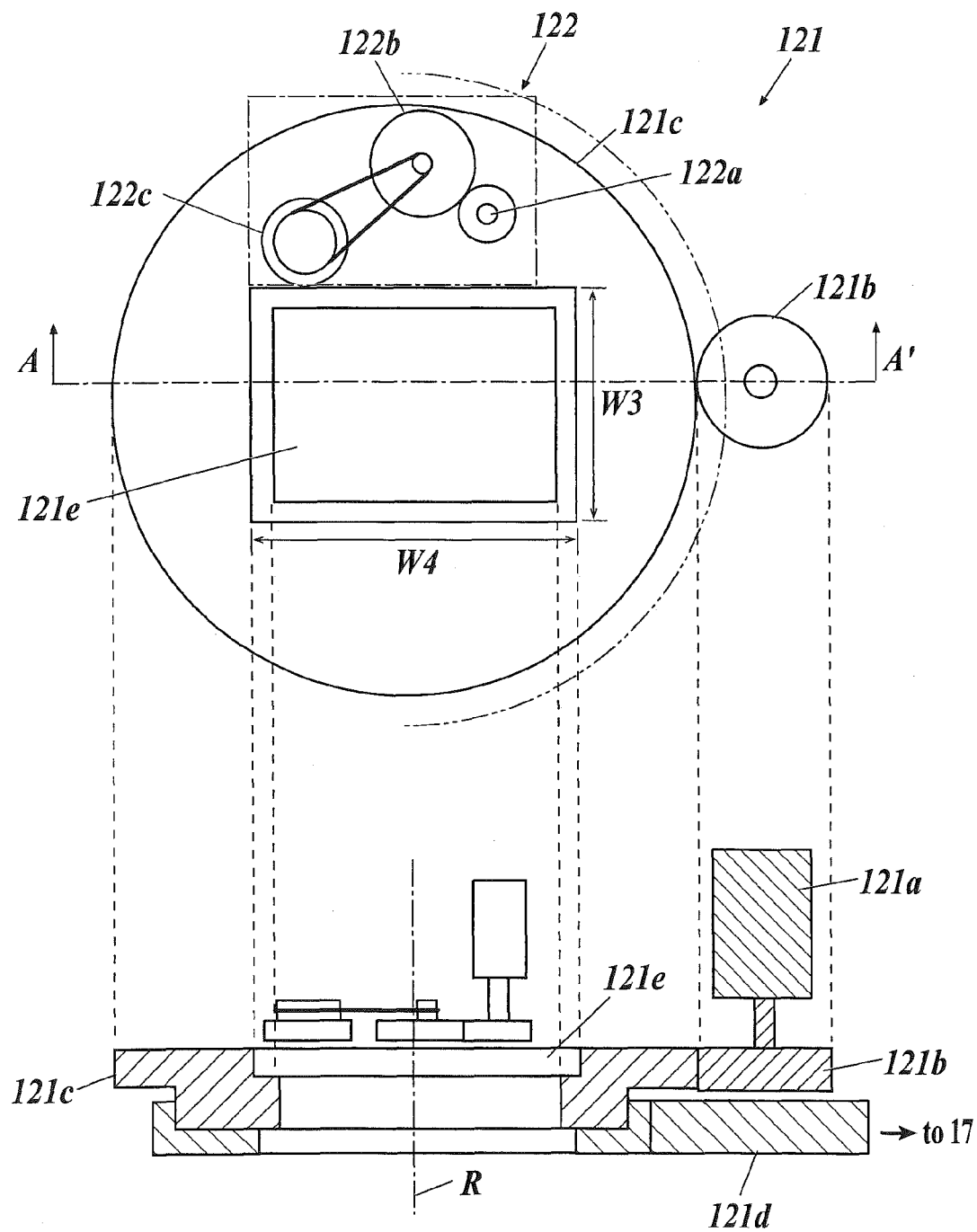
FIG. 3 is a plan view and side view of a multi-slit rotating unit.

FIG. 3 shows a plan view of the multi-slit rotating unit 121 and the drive unit 122 and a cross-sectional view thereof taken along a line A-A'.

As shown in FIG. 3, the multi-slit rotating unit 121 is composed by including a motor unit 121a, a gear unit 121b, a gear unit 121c, a support portion 121d, and the like. The motor unit 121a, the gear unit 121b and the gear unit 121c are held in the holding portion 17 through the support portion 121d.

The motor unit 121a is a pulse motor switchable to micro-step drive. The motor unit 121a is driven in response to control from a control unit 181 (refer to FIG. 8), and through the gear unit 121b, rotates the gear unit 121c about the X-ray irradiation axis (shown by an alternate long and short dash line in FIG. 3) taken as a center. The gear unit 121c includes an opening portion 121e for mounting thereon the multi-slit 12 held in the holder 12b. The gear unit 121c is rotated, whereby the multi-slit 12 mounted on the opening portion 121e can be rotated about the X-ray irradiation axis, and the slit arraying direction of the multi-slit 12 can be varied. Note that, in the imaging, the multi-slit 12 just needs to be capable of rotating approximately from 0° to 90°, and accordingly, it is not necessary that the gear unit 121c be provided around an entire circumference of the multi-slit 12, and the multi-slit 12 just needs to be capable of rotating within a range (90° each in a forward rotation direction and reverse rotation direction) shown by a chain double-dashed line in FIG. 3.

The opening portion 121e has a shape and a size, which enable the multi-slit 12 held in the holder 12b to be fitted thereinto from the above. Here, a size W4 of the holder 12b in the slit arraying direction is slightly larger than a size W2 of the holder 12b in the slit arraying direction, and it is made possible to slide the multi-slit 12 in the slit arraying direction. Note that a size W3 of the opening portion 121e in a direction perpendicular to the slit arraying direction is set to a dimension that is precisely equivalent, in terms of fitting, to the size W1 of the holder 12b in the direction perpendicular to the slit arraying direction. When the holder 12b is mounted on the opening portion 121e, the rack 12a provided on the holder 12b is arranged outside of the opening portion 121e so as to be capable of engaging with the pinion 122c to be described later.

The drive unit 122 is composed by including a precise decelerator that moves the multi-slit 12 in the slit arraying direction in a unit ranging from 0.1 μm to several ten μm in response to a multi-slit cycle, and the like. For example, as shown in FIG. 3, the drive unit 122 includes a motor unit 122a, a gear unit 122b, a pinion 122c, and the like, and is fixed to the gear unit 121c of the multi-slit rotating unit 121 by an L-shaped metal plate (not shown) and the like. In such a way, the multi-slit 12 and the drive unit 122 are configured to rotate integrally with each other.

For example, the motor unit 122a is driven in response to control from the control unit 181, and rotates the pinion 122c through the gear unit 122b. The pinion 122c engages with the rack 12a of the multi-slit 12 and rotates, thereby moves the multi-slit 12 in the slit arraying direction.

Returning to FIG. 1, the subject platform 13 is a platform for placing thereon the hand and the fingers, which are the subject. Preferably, the subject platform 13 is provided at a height that enables the patient's elbow to be placed thereon. As described above, the subject platform 13 is configured so as to be capable of placing all the way to the patient's elbow thereon, whereby the patient can take a comfortable posture, and a motion of imaging target regions on the finger tips can be reduced during an imaging time that is relatively long.

Figure 4A:
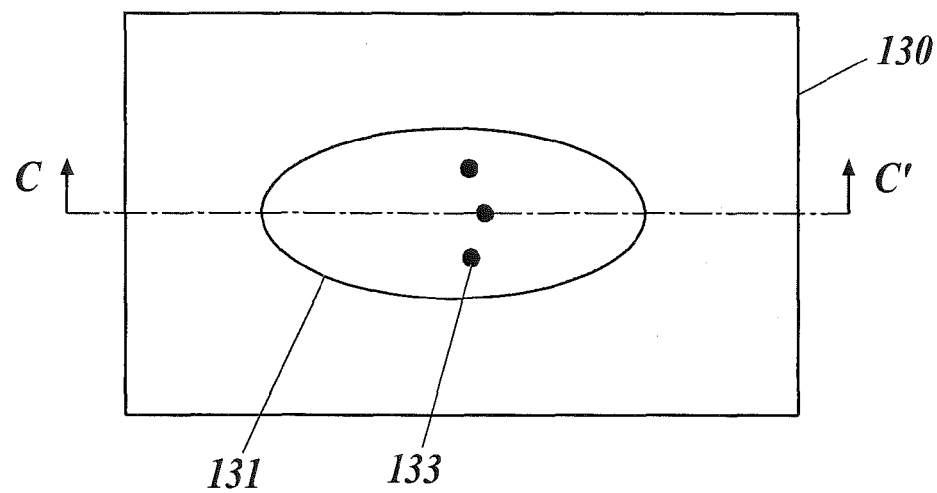
FIG. 4A is a plan view of a subject holder.
Figure 4B:
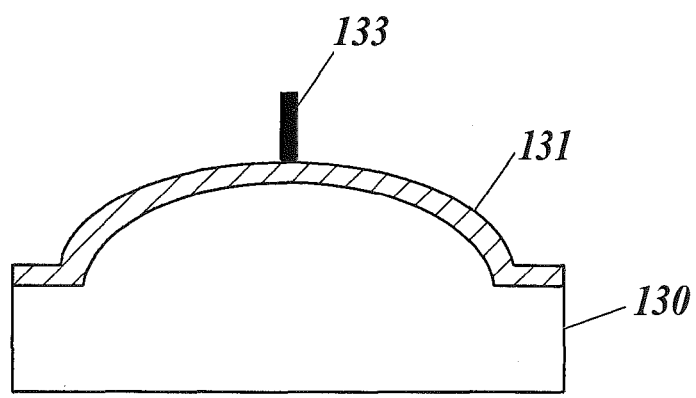
FIG. 4B is a side view of the subject holder.

Moreover, in the subject platform 13, a subject holder 130 for fixing the subject is provided. The subject holder 130 is attachable/detachable in response to the subject. As shown in FIG. 4A, the subject holder 130 is a plate-like member added with an ellipsoidal shape 131 like a mouse easy to grasp by the palm. With regard to the above-described ellipsoidal shape 131, when a cross section thereof is observed from the side, then as shown in FIG. 4B, the ellipsoidal shape 131 has a gentle convex surface with a size of the palm, and by the fact that the patient grasps the ellipsoidal shape 131 by the palm, a downward motion of the subject can be suppressed in a state where the subject is less likely to get tired.

In the case where the subject holder 130 has a shape or thickness, in which an x-ray complex refractive index is uneven from place to place, a dose of the X-ray that reaches the X-ray detector 16 becomes nonuniform since the X-ray complex refractive index of the subject holder 130 is uneven.

Preferably, finger spacers 133 are further provided on the subject holder 130 for the purpose of stabilizing a posture of the subject. Moreover, a size of the hand and spaces among the fingers differ for each subject, and accordingly, it is preferable that the subject holder 130 be created in accordance with the palm shape of each subject, and that the subject holder 130 for each patient be mounted on the subject platform 13 by a magnet and the like at the imaging time. The subject platform 13 supports a load of a portion from the arm to the wrist, and accordingly, the subject holder 130 just needs to endure a load of such fingertip portions and force by which the patient holds down the subject holder 130 concerned from the above, and it is possible to mold the subject holder 130 from plastic, which is inexpensive and enables mass production.

Returning to FIG. 1, in a similar way to the multi-slit 12, the first grating 14 is a diffraction grating, in which a plurality of slits is arrayed and provided in the direction perpendicular to the z-direction as the X-ray irradiation axis direction. The first grating 14 can be formed by the photolithography using the UV in a similar way to the multi-slit 12, or alternatively, a grating structure may be formed only of silicon by performing deep drilling processing in fine lines for a silicon substrate by a so-called ICP method. A slit cycle of the first grating 14 is 1 to 20 (μm). A width of each slit is 20 to 70 (%) of the slit cycle, preferably, 35 to 60 (%). A height of each slit is 1 to 100 (μm).

In the case of using a phase type as the first grating 14, a height (height in the z-direction) of each slit is set to a height at which a phase difference between two types of materials forming the slit cycle, that is, between materials of an X-ray transmission portion and an X-ray shielding portion becomes π/8 to 15×π/8. Preferably, the height concerned is a height at which the phase difference becomes π/4 to 3×π/4. In the case of using an absorption type as the first grating 14, the height of each slit is set to a height at which the X-ray is sufficiently absorbed by the X-ray shielding portion.

In the case where the first grating 14 is a phase type, it is necessary that the distance d4 between the first grating 14 and the second grating 15 substantially satisfy the following condition:

$$d4 = (m+1/2) \cdot x_1^2 / \lambda$$

where m is an integer, and λ is a wavelength of the X-ray.

With regard to the above-described condition, there is described an example of the case where the first grating 14 is a π/2-type grating, that is, the phase difference of the first grating between the materials of the X-ray shielding portion and the X-ray transmission portion is approximately π/2. However, a π-type may be used for the first grating 14, and a condition corresponding to the type of grating for use just needs to be arithmetically operated.

In a similar way to the multi-slit 12, the second grating 15 is a diffraction grating, in which a plurality of slits is arrayed and provided in the direction perpendicular to the z-direction as the X-ray irradiation axis direction. The second grating 15 can also be formed by the photolithography. A slit cycle of the second grating 15 is 1 to 20 (μm). A width of each slit is 30 to 70 (%) of the slit cycle, preferably, 35 to 60 (%). A height of each slit is 1 to 100 (μm).

In this embodiment, grating surfaces of the first grating 14 and the second grating 15 are vertical with respect to the z-direction (that is, parallel to an x-y plane), and the first grating 14 and the second grating 15 are arranged so that the slit arraying direction of both thereof can be tilted with respect to each other by a predetermined angle in the x-y plane; however, the first grating 14 and the second grating 15 may be arranged so that both of the slit arraying directions can be parallel to each other. Moreover, in this embodiment, the first grating 14 and the second grating 15 have a disc shape.

For example, the multi-slit 12, the first grating 14 and the second grating 15, which are described above, can be configured as described below.

With regard to X-ray tube of X-ray source 11, focal point diameter: 300 (μm); tube voltage: 40 (kVP); and additional filter: aluminum with a thickness of 1.6 (mm)

Distance d1 from focal point of X-ray source 11: 240 (mm)
Distance d3 from multi-slit 12 to first grating 14: 1110 (mm)
Distance d3+d4 from multi-slit 12 to second grating 15: 1370 (mm)
Size of multi-slit 12: 10 (square mm); slit cycle 22.8 (μm)
Size of first grating 14: 50 (square mm); slit cycle: 4.3 (μm)
Size of second grating 15: 50 (square mm); slit cycle: 5.3 (μm)

Figure 5:
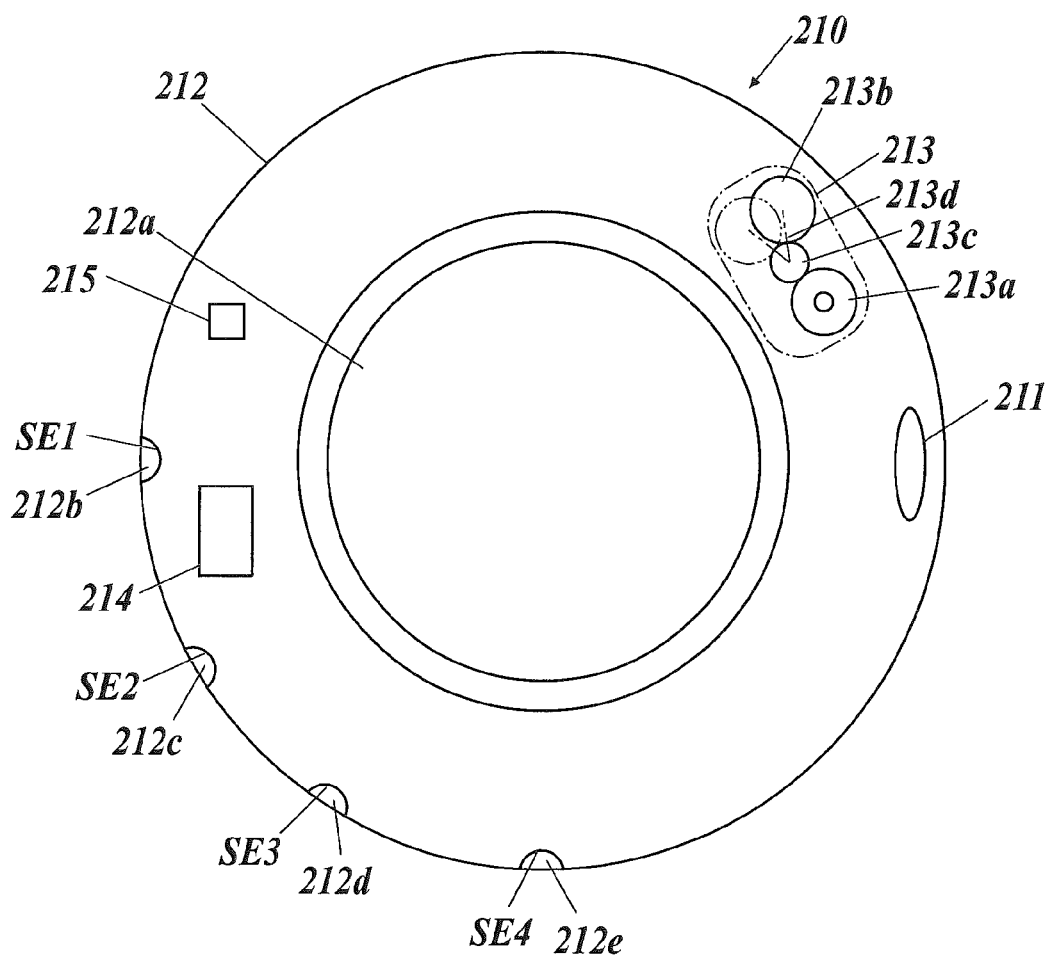
FIG. 5 is a plan view of a grating rotating unit.
Figure 6:
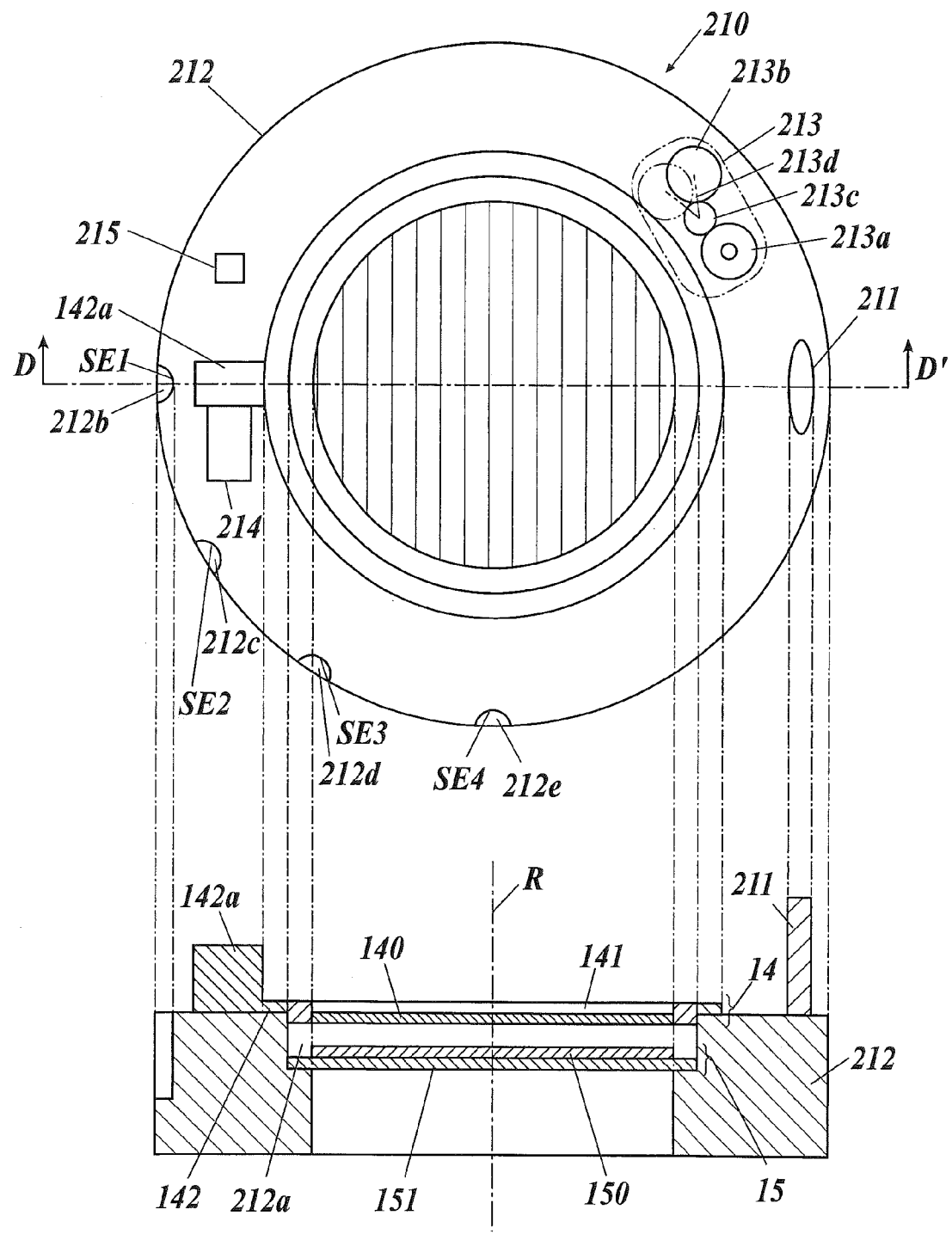
FIG. 6 is a plan view and side view of the grating rotating unit in a state where a first grating and a second grating are mounted thereon.

In this embodiment, the first grating 14 and the second grating 15 are mounted on a grating rotating unit 210. FIG. 5 shows a plan view of a grating rotating unit 210. FIG. 6 shows a plan view of the grating rotating unit 210 in a state where the first grating 14 and the second grating 15 are mounted thereon, and a cross-sectional view of the grating rotating unit 210 concerned, taken along a line D-D'.

As shown in FIG. 5, the grating rotating unit 210 is composed by including a handle 211, a relative angle adjusting unit 213, a stopper 214 and the like on a rotating tray 212.

The rotating tray 212 includes an opening portion 212a for holding the first grating 14 and the second grating 15.

Here, in this embodiment, the first grating 14 is composed of: a circular grating portion 140 formed in such a manner that the plurality of slits is arrayed; and a first holder portion 141 and a second holder portion 142 for attaching this grating portion 140 to the opening portion 212a (refer to FIG. 6). The first holder portion 141 is a member, which is attached onto an outer circumference of the grating portion 140, and has substantially the same radius (a radius of an outer circumference) as that of the opening portion 212a. The first holder portion 141 is fitted to the opening portion 212a at the time of mounting the first grating 14. The second holder portion 142 is a member, which is attached further to the outside of the first holder portion 141, and has a radius (a radius of an outer circumference) slightly larger than that of the opening portion 212a. In the second holder portion 142, a part of the outer circumference thereof is subjected to a gear process. Moreover, a protruding portion 142a is provided on a predetermined position of the outer circumference of the second holder portion 142.

The second grating 15 is composed of: a circular grating portion 150 formed in such a manner that the plurality of slits is arrayed; and a holder portion 151 for attaching this grating portion 150 to the opening portion 212a. The holder portion 151 is a disc-like member that has a substantially similar radius to a radius of the opening portion 212a. The grating portion 150 is held on an upper surface of a center of the holder portion 151 (refer to FIG. 6).

In the event of mounting the first grating 14 and the second grating 15 on the rotating tray 212, first, the second grating 14 is fitted to a bottom surface of the opening portion 212a. Next, the first grating 14 is fitted to the opening portion 212a from the above of the second grating 15. In such a way, in a state shown in FIG. 6, the first grating 14 and the second grating 15 are held in the rotating tray 212.

With regard to the first grating 14 and the second grating 15, which are held on the opening portion 212a, a relative angle thereof in the slit arraying direction is adjusted by the relative angle adjusting unit 213 in response to an imaging mode.

Here, the X-ray imaging apparatus 1 has: the first imaging mode of performing the imaging in the plurality of steps for use in the reconstructed image by the fringe scanning method; and the second mode of performing the imaging in one or two directions for use in the reconstructed image for the Fourier transform method. A relative angle between a slit direction of the first grating 14 and a slit direction of the second grating, which is required for the imaging for the fringe scanning method, depends on the cycle of the second grating and the number of fringes. In the fringe scanning method, it is known that, as the number of interference fringes in the moire images is smaller, and in addition, as the interference fringes are sharper, the reconstructed image to be created based on the moire images becomes sharper (refer to Non-Patent Literature 2). Accordingly, if it is assumed that the cycle of the second grating is set at 5.3 µm, and that the number of interference fringes in an image with a size of 60 square mm is set to range approximately from zero to three, then it is necessary to set the relative angle from 0° to ±0.015°. Meanwhile, the relative angle between the slit direction of the first grating 14 and the slit direction of the second grating 15, which is required for the imaging for the Fourier transform method, depends on a pixel pitch and spatial resolution of the X-ray detector 16. If it is assumed that the X-ray detector 16 is a detector (spatial resolution: 30 µm to 200 µm) used in general, it is necessary to set the relative angle therein from 0.4° to 3°. Hence, in order to perform the imaging while switching the first imaging mode and the second imaging mode, it is necessary to adjust the relative angle between the first grating and the second grating in response to the imaging mode. However, for example, in the above-described configuration, an angular deviation of 0.005° in the fringe scanning method is equivalent to one cycle of the fringes. In order to always maintain a state where the fringes are expanded in the fringe scanning method, adjustment with milli-degree accuracy is required, and accordingly, it is difficult to manually adjust the relative angle between the slit directions of the first grating 14 and the second grating 15.

Accordingly, in the X-ray imaging apparatus 1, the relating angle adjusting unit 213 makes it possible to automatically adjust the relative angle between the first grating 14 and the second grating 15 in response to such an imaging mode set by an operation unit 182.

As shown in FIGS. 5 and 6, the relative angle adjusting unit 213 is composed of a motor unit 213a, a first gear 213b, a second gear 213c, and a lever 213d. The motor unit 213a is engaged with the second gear 213c, and rotates the second gear 213c in response to the control from the control unit 181. With regard to the second gear 213c, a center thereof is connected to a center of the first gear 213b through the lever 213d, and a circumference thereof is engaged with the first gear 213b. When the second gear 213c rotates in response to drive of the motor unit 213a, then about the center of the second gear 213c taken as a rotation axis, the first gear 213b rotates and moves along a circumference of the second gear 213c, and is engaged with a gear portion of the second holder portion 142 of the first grating 14, thus making it possible to rotate the first grating 14 about the X-ray irradiation axis without rotating the second grating 15.

In this embodiment, at the time of factory shipment, in order so that the relative angle between the slit directions of the first grating 14 and the second grating 15 can become an optimum relative angle for the time of the first imaging mode (the imaging mode for the fringe scanning method) when the protruding portion 142a of the second holder portion 142 thrusts against the stopper (protrusion) 214 provided on the rotating tray 212, the position of the stopper 214 and the relative angle between the first grating 14 and the second grating 15 are adjusted in advance, and the first grating 14 and the second grating 15 are mounted on the opening portion 212a. When the second imaging mode (the imaging mode for the Fourier transform) is set, the motor unit 213a of the relative angle adjusting unit 213, which adopts a pulse motor, is driven (subjected to energization control) by the control unit 181 so that the relative angle between the first grating 14 and the second grating 15 can become optimum for the second imaging mode. In such a way, the first gear 213b rotates through the second gear 213c, and is engaged with the gear portion of the second holder portion 142, and the second holder portion 142 rotates so that the relative angle between the first grating 14 and the second grating 15 can become optimum for the second imaging mode. Thereafter, the pulse motor concerned is varied to an energization state, and is set to an energization state (less than 50% of a rated current at a drive time, and the like) to an extent of exerting motor self-holding force (excitation force) that overcomes spring force to be described later, and can thereby maintain the second holder portion 142 at the phase concerned.

Note that, since a rotation angle at this time is as small as approximately 1°, preferably, first, the second holder portion 142 is rotated counterclockwise by the pulse motor of the motor unit 213a until the protruding portion 142a reaches a reference position, and when a sensor (not shown) senses that the protruding portion 142a has reached the reference position 215, a rotation direction of the second holder portion 142 is switched to a clockwise direction, and the second holder portion 142 is rotated by the micro-step drive.

The second holder portion 142 is urged by a spring (not shown). When the engagement between the first gear 213b and the second holder portion 142 is released by the drive of the motor unit 213a, the protruding portion 142a returns to the position of the stopper 214 by urging force of the spring. That is to say, the first grating 14 and the second grating 15 return to the relative angle optimum for the first imaging mode.

In such a way as described above, the relative angle between the first grating 14 and the second grating 15 is set to the angle corresponding to the imaging mode.

Moreover, with respect to the subject, the grating rotating unit 210 can integrally rotate the first grating 14 and the second grating 15, between which the relative angle is adjusted, about the X-ray irradiation axis (shown by a dotted line R in FIG. 6).

Here, in the Talbot interferometer and the Talbot-Lau interferometer, each of which uses a one-dimensional grating (slit), there are characteristics that a structure extended linearly in parallel to the slit directions of the first grating 14 and the second grating 15 cannot be imaged sharply. Hence, it is necessary to adjust angles of the slit directions of the first grating 14 and the second grating 15 in response to an arrangement direction of the structure of interest in the subject. By a mechanism that follows, the grating rotating unit 210 can integrally rotate the first grating 14 and the second grating 15 about the X-ray irradiation axis while maintaining the relative angle therebetween, and can adjust the angles of the slit directions of the first grating 14 and the second grating 15 with respect to the arrangement direction of the structure of interest in the subject.

As mentioned above, the handle 211 is provided on the rotating tray 212. The handle 211 is a protrusion for allowing an operator such as a radiographer to manually rotate the rotating tray 212 about the X-ray irradiation axis (shown by the dotted line R of FIG. 6) taken as an axis. Moreover, the rotating tray 212 has recessed portions 212b to 212e for fixing the rotation angle of the rotating tray 212. The recessed portions 212b to 212e are provided at positions located at predetermined rotation angles (here, 0°, 30°, 60°, 90°) from a position predetermined to be 0° (here, a position where the recessed portion 212b is opposite to a ball of a tray fixing member 171b is defined as the position of 0°). In the recessed portions 212b to 212e, angle sensing sensors SE1 to SE4 are provided, respectively. The angle sensing sensors SE1 to SE4 sense that the rotating tray 212 is engaged with the tray fixing member 171b, and outputs a signal of this sensing to the control unit 181.

As described above, the rotating tray 212 is manually rotated, and accordingly, it is not necessary to provide an electric cord and the like for integrally rotating the first grating 14 and the second grating 15 within a range that can be touched by the patient, and safety can be ensured.

Note that, in this embodiment, positions (angles) of the first grating 14 and the second grating 15 when the rotating tray 212 is set at 0° are defined as home positions. Moreover, a position (angle) where the slit direction of the first grating 14 and the slit direction of the multi-slit 12 are parallel to each other when the first grating 14 and the second grating 15 are at the home positions is defined as a home position of the multi-slit 12.

Figure 7A:
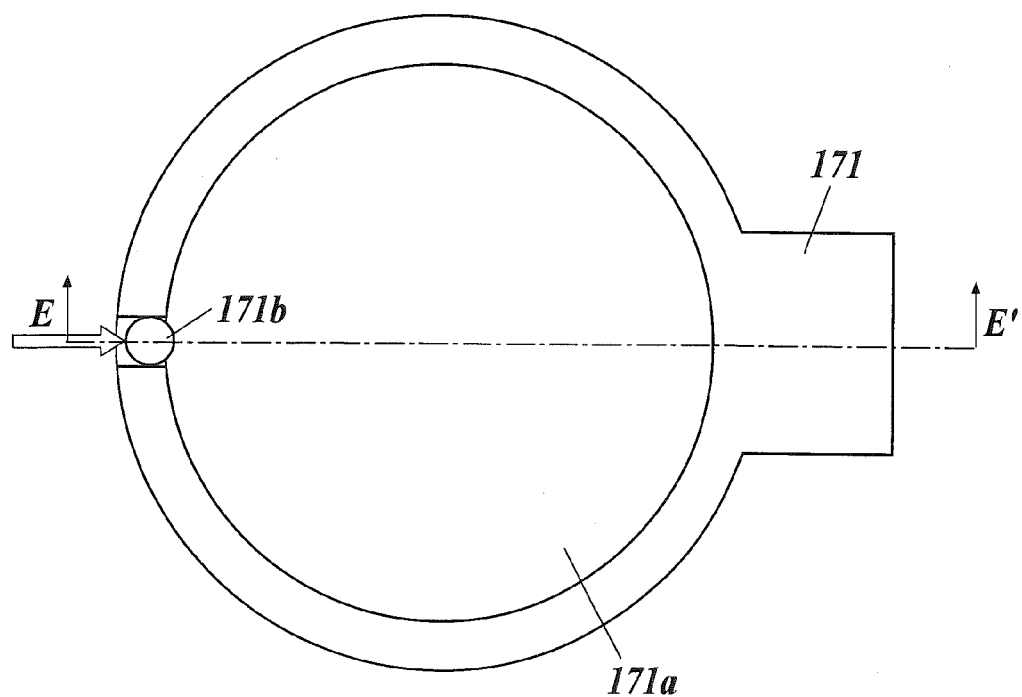
FIG. 7A is a plan view enlargedly showing a holding portion of the grating rotating unit in a holding portion of FIG. 1.
Figure 7B:
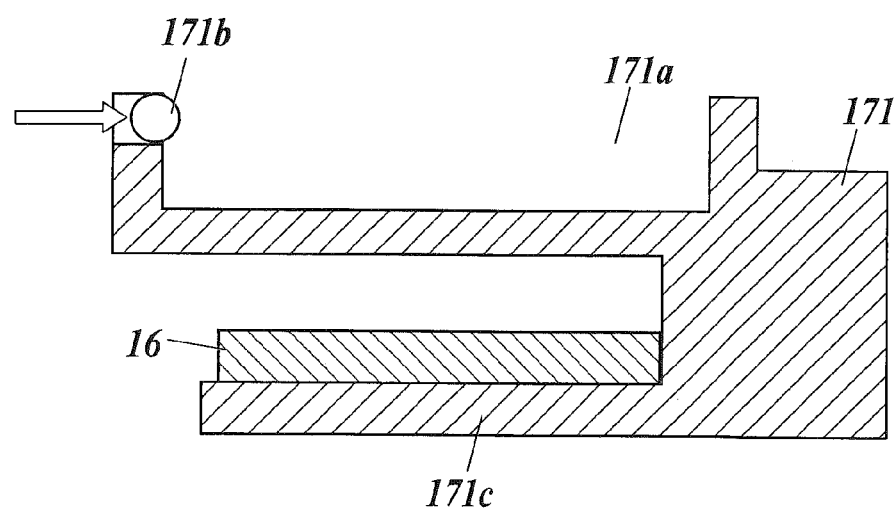
FIG. 7B is a cross-sectional view of the holding portion, taken along a line E-E' in FIG. 7A.
Figure 7C:
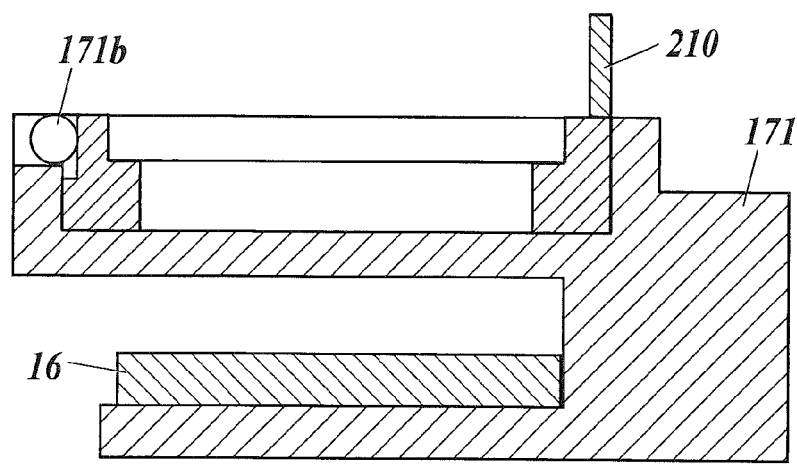
FIG. 7C is a view showing a state where the grating rotating unit is held in the holding portion.

FIG. 7A is a plan view enlargedly showing a holding portion 171 for the grating rotating unit 210 in the holding portion 17, and FIG. 7B is a cross-sectional view taken along a line E-E' in FIG. 7A. FIG. 7C is a view showing a state where the grating rotating unit 210 is held in the holding portion 17.

As shown in FIG. 7A and FIG. 7B, in the holding portion 171, there are provided: an opening portion 171a, which has a size precisely fitted to the rotating tray 212 of the grating rotating unit 210, and rotatably holds the rotating tray 212; and the tray fixing member 171b for fixing the rotation angle of the rotation tray 212. In order that the transmission of the X-ray cannot be inhibited, preferably, a space between a bottom of the opening portion 171a and a mounting portion of the X-ray detector 16 is made hollow, or is sealed by aluminum, carbon or the like with high X-ray transmissivity. The tray fixing member 171b composed of: the ball to be engaged with any of the recessed portions 212b to 212e where the recessed portion concerned is located so as to be opposite to the tray fixing member 171b; and a slide guide (a guide of a compression spring, not shown) for guiding the ball in an arrow direction of FIG. 7A and FIG. 7B. When the rotation of the rotating tray 212 is stopped at the position where any of the recessed portions 212b to 212e is opposite to the tray fixing member 171b, the ball is engaged with the opposite recessed portion by the slide guide of the tray fixing member 171b, and in addition, the engagement of the ball is sensed by the angle sensing sensor (SE1 to SE4) provided in the recessed portion, and such a sensing signal is outputted to the control unit 181. In such a way, the control unit 181 is configured to be capable of sensing the rotation angle of the rotating tray 212, that is, rotation angles of the first grating 14 and the second grating 15.

Figure 7D:
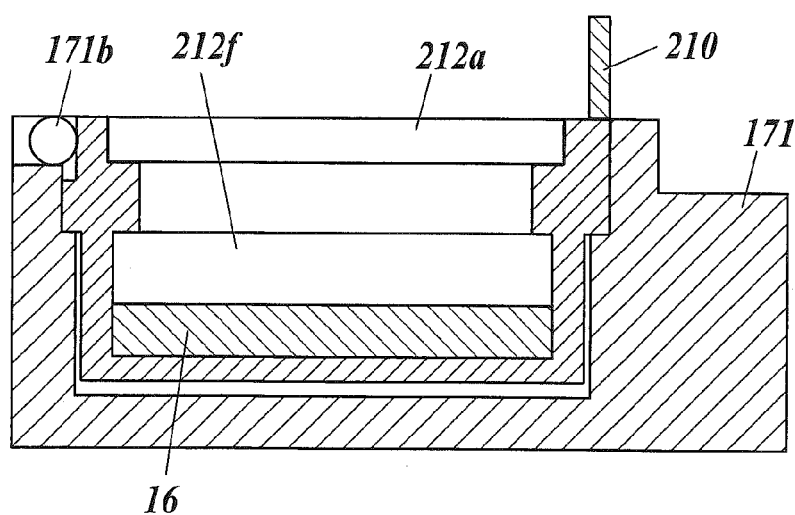
FIG. 7D is a cross-sectional view showing a rotation tray capable of rotating the first grating, the second grating and an X-ray detector with one another.

Moreover, as shown in FIG. 7D, a configuration may be adopted so that a mounting portion 212f for the X-ray detector 16 can be provided below the opening portion 212a of the rotating tray 212, and that the first grating 14, the second grating 15 and the X-ray detector 16 can thereby rotate integrally with one another. With this configuration, there is no anisotropic influence on sharpness in vertical and horizontal directions of the X-ray detector 16, and accordingly, vertical and horizontal sharpness the reconstructed image can be made substantially constant regardless of the rotation angles of the first grating 14 and the second grating 15.

Returning to FIG. 1, in the X-ray detector 16, conversion elements which generate electric signals in response to the X-ray are two-dimensionally arranged. The X-ray detector 16 reads the electric signals, which are generated by the conversion elements concerned, as image signals. A pixel size in the X-ray detector 16 is 10 to 300 (μm), preferably, 50 to 200 (μm).

Preferably, the X-ray detector 16 is fixed at a position in the holding unit 17 so as to abut against the second grating 15. This is because, as the distance between the second grating 15 and the X-ray detector 16 becomes larger, the moire image to be obtained by the X-ray detector 16 becomes more blurred.

As the X-ray detector 16, an FPD (Flat Panel Detector) can be used. As the FPD, there are: an indirect conversion type of converting the X-ray to the electric signal by photoelectric conversion elements through a scintillator; and a direct conversion type of converting the X-ray directly to the electric signal, and either thereof may be used.

In the indirect conversion type, the photoelectric conversion elements are two-dimensionally arranged together with TFTs (thin film transistors) under a scintillator plate made of CsI, $Gd_2O_2$ or the like, whereby the respective pixels are configured. When the X-ray incident onto the X-ray detector 16 is absorbed to the scintillator plate, the scintillator plate emits light. By the light thus emitted, electric charges are accumulated in the respective photoelectric conversion elements, and the electric charges thus accumulated are read out as an image signal.

In the direct conversion type, an amorphous selenium film with a film thickness of 100 to 1000 (μm) is formed on glass by thermal vapor deposition of amorphous selenium, and an amorphous selenium film and electrodes are deposited on an array of the TFTs arranged two-dimensionally. When the amorphous selenium film absorbs the X-ray, a voltage is liberated into an object in a form of an electron-hole pair, and such voltage signals between the electrodes are read by the TFTs.

Note that imaging means such as a CCD (Charge Coupled Device) and an X-ray camera may be used as the X-ray detector 16.

A description is made of a series of processing by the FPD at the time of the X-ray imaging.

First, the FPD resets itself, and removes therefrom unnecessary electric charges remaining after the previous imaging (reading). Thereafter, the accumulation of the electric charges is performed at timing when the irradiation of the X-ray is started, and the accumulated electric changes are read as the image signal at timing when the irradiation of the X-ray is ended. Note that, immediately after such resetting, after the image signal is read, and so on, dark reading for offset correction is performed.

Figure 8:
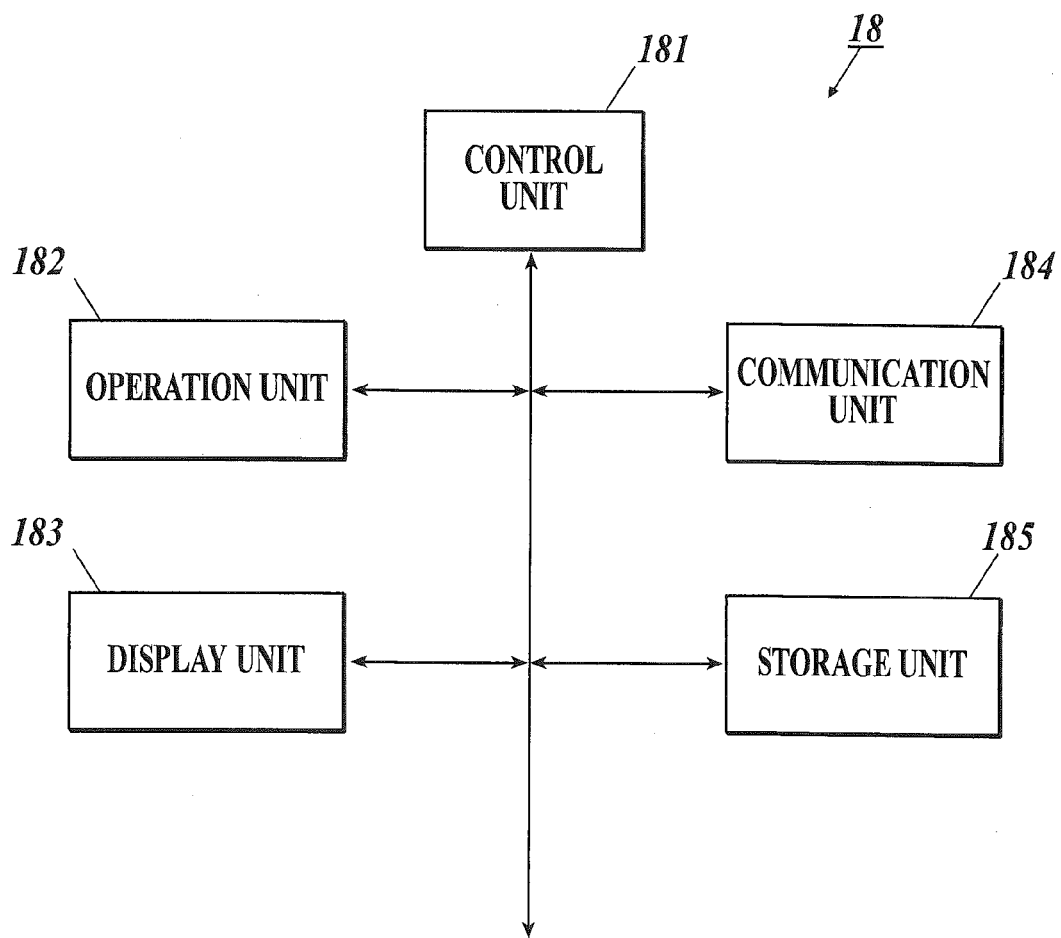
FIG. 8 is a block diagram showing a functional configuration of a main body section.

As shown in FIG. 8, the main body section 18 is composed by including the control unit 181, the operation unit 182, a display unit 183, a communication unit 184, and a storage unit 185.

The control unit 181 is composed of a CPU (Central Processing Unit), a RAM (Random Access Memory), and the like, and by cooperation with programs stored in the storage unit 185, controls the respective units of the X-ray imaging apparatus 1, and executes a variety of processing. For example, the control unit 181 executes the variety of processing including imaging control processing to be described later.

In addition to an exposure switch and a group of keys for use in input operations of imaging conditions and the like, the operation unit 182 includes a touch panel composed integrally with a display of the display unit 183, generates operation signals corresponding to operations for these, and outputs the generated operation signals to the control unit 181.

In accordance with display control of the control unit 181, the display control unit 183 displays an operation screen, an operation situation of the X-ray imaging apparatus 1, and the like on the display.

The communication unit 184 includes a communication interface, and communicates with the controller 5 on a network. For example, the communication unit 184 transmits the moire image, which is read by the X-ray detector 16 and stored in the storage unit 185, to the controller 5.

The storage unit 185 stores programs to be executed by the control unit 181, and data necessary to execute the programs. Moreover, the storage unit 185 stores the moire image obtained by the X-ray detector 16.

The controller 5 controls imaging operations of the x-ray imaging apparatus 1 in accordance with operations by the operator. Moreover, the controller 5 functions as an image processing unit that creates the reconstructed image for the diagnosis by using the moire image obtained by the X-ray imaging apparatus 1.

Figure 9:
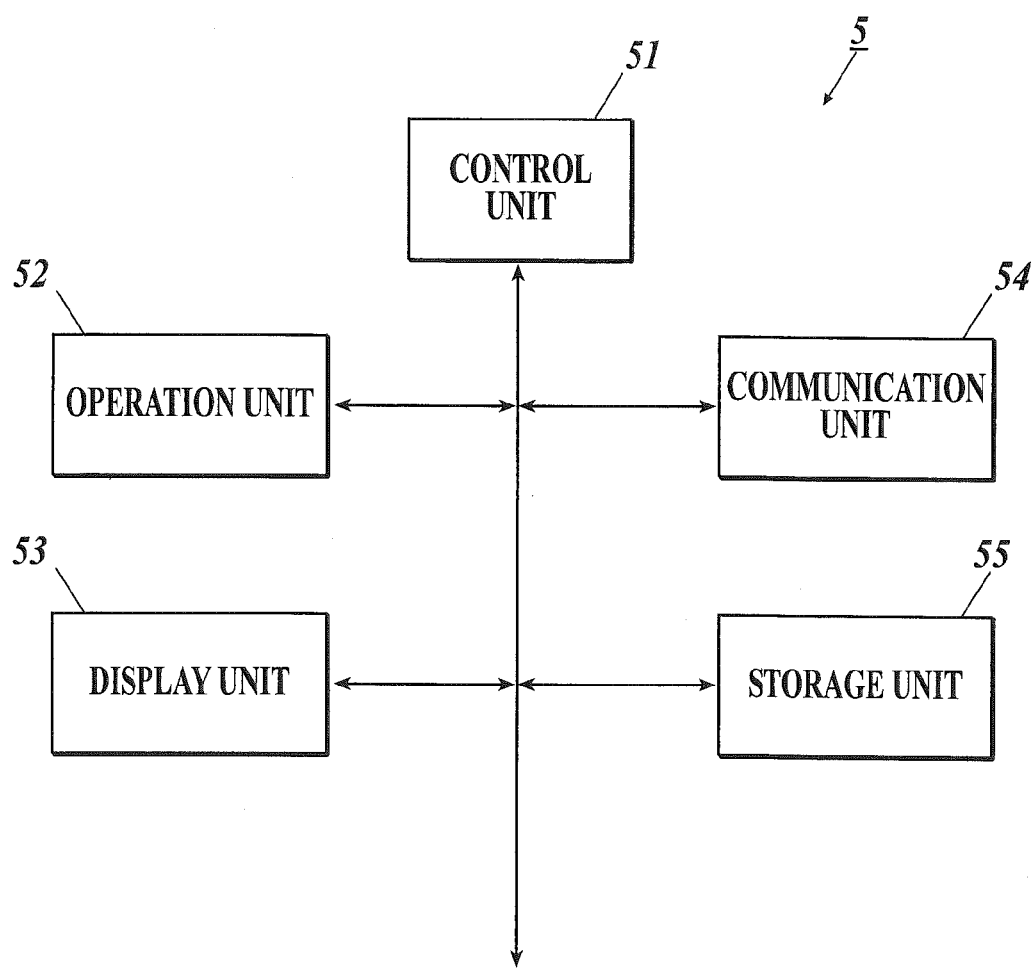
FIG. 9 is a block diagram showing a functional configuration of a controller.

As shown in FIG. 9, the controller 5 includes a control unit 51, an operation unit 52, a display unit 53, a communication unit 54, and a storage unit 55.

The control unit 51 is composed of a CPU (Central Processing Unit), a RAM (Random Access Memory) and the like, and by cooperation with programs stored in the storage unit 55, executes a variety of processing, which includes: reconstructed image creation/display processing by the fringe scanning method to be described later; and reconstructed image creation/display processing by the Fourier transform method to be described later.

The operation unit 52 is composed by including: a keyboard including cursor keys, number input keys, a variety of function keys and the like; and a pointing device such as a mouse, and outputs, as input signals, a depression signal of a key depressed on the keyboard and an operation signal by the mouse to the control unit 51. The operation unit 52 may also be configured to include a touch panel composed integrally with a display of the display unit 53, to generate operation signals corresponding to operations for these, and to output the generated operation signals to the control unit 51. In this embodiment, for example, the operation unit 52 can set types of images to be displayed in Step S22 of FIG. 14B and Step S43 of FIG. 21, switching timing of the display of the images, and the like for each of regions and for each of users (physicians).

For example, the display unit 53 is composed by including a monitor such as a CRT (Cathode Ray Tube) or an LCD (Liquid Crystal Display), and displays an operational screen, the operation situation of the X-ray imaging apparatus 1, the reconstructed image thus created, and the like in accordance with display control of the control unit 51.

The communication unit 54 includes a communication interface, and communicates with the X-ray imaging apparatus 1 and the X-ray detector 16 on the network through wired communication or wireless communication. For example, the communication unit 54 transmits the imaging conditions and the control signal to the X-ray imaging apparatus 1, and receives the moire images from the X-ray imaging apparatus 1 or the X-ray detector 16.

The storage unit 55 stores programs to be executed by the control unit 51, and data necessary to execute the programs. For example, the storage unit 55 stores imaging order information indicating orders reserved by an RIS, an HIS or the like or by reservation devices (not shown). The imaging order information is information such as a patient name, an imaging target region and an imaging mode.

Moreover, the storage unit 55 stores setting information set by the operation unit 52, for example, the types of the images to be displayed in Step S22 of FIG. 14B and Step S43 of FIG. 21, the switching timing of the display of the images, and the like in association with region information and user IDs.

Furthermore, in association with the imaging order information, the storage unit 55 stores the moire images obtained by the X-ray detector 16, and the reconstructed images for the diagnosis, which are created based on the moire images.

Moreover, the storage unit 55 stores a reference image (described later in detail) showing a typical case of a lesion in association with a name of the lesion, a type of the image (fringe scanning method or Fourier transform method, absorption image or differential phase image or small-angle scattering image) and the like.

Furthermore, the storage unit 55 prestores gain correction data, a defective pixel map and the like, which correspond to the X-ray detector 16.

In the controller 5, when a list display of the imaging order information is instructed by an operation of the operation unit 52, the control unit 51 reads out the imaging order information from the storage unit 55, and displays the imaging order information on the display unit 53. When the imaging order information is designated by the operation unit 52, setting information regarding the imaging conditions (including the imaging mode) corresponding to the designated imaging order information, an warm-up instruction for the X-ray source 11 and the like are transmitted to the X-ray imaging apparatus 1 by the communication unit 54. In such a way, the imaging mode is set for the X-ray imaging apparatus 1. That is to say, the controller 5 functions as a setting unit that sets the imaging mode. Moreover, in the case where the X-ray detector 16 is a cableless cassette-type FPD device, the control unit 51 activates the X-ray detector 16 to an imaging enabled state from a sleep state for preventing exhaustion of an internal battery.

In the X-ray imaging apparatus 1, preparation of the X-ray imaging is executed when the setting information regarding the imaging conditions, and the like are received from the controller 5 by the communication unit 184.

A description is made of an X-ray imaging method (an imaging method of a first imaging mode) by the Talbot-Lau interferometer in the above-described X-ray imaging apparatus 1.

Figure 10:
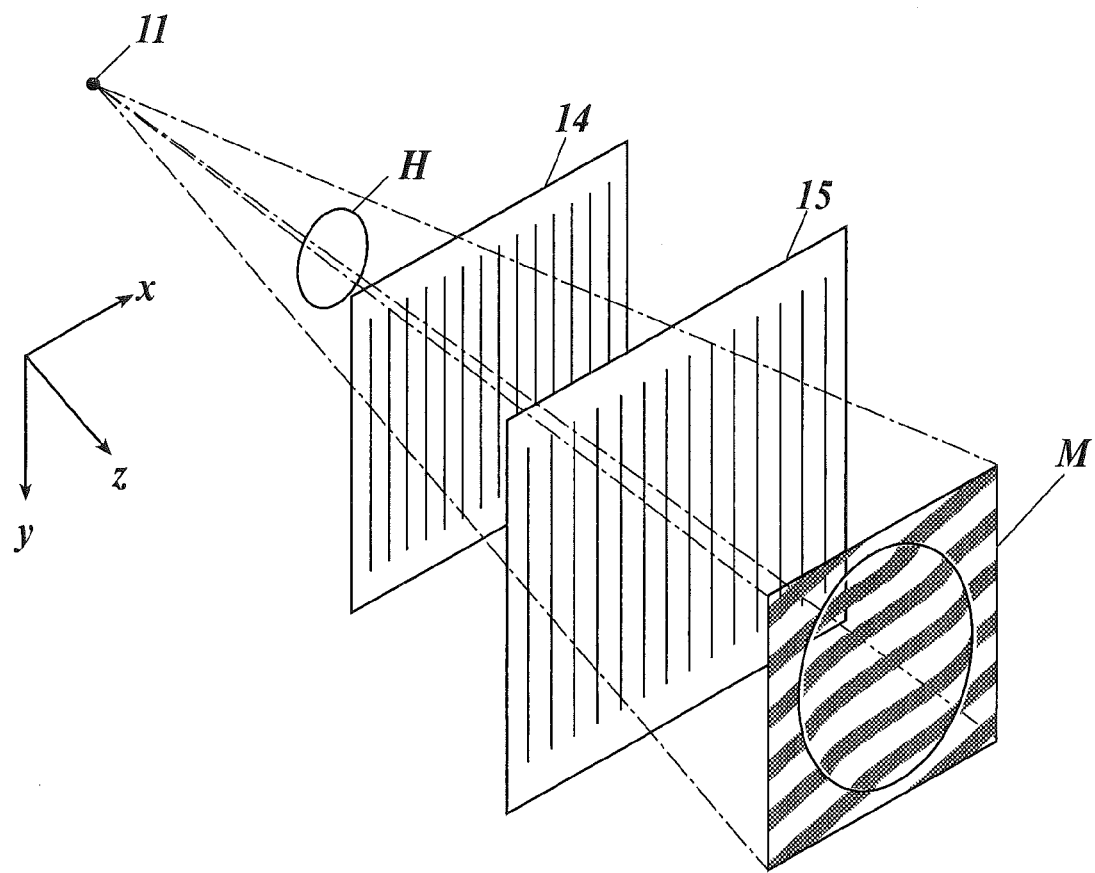
FIG. 10 is a view explaining a principle of a Talbot interferometer.

As shown in FIG. 10, when the X-ray irradiated from the X-ray source 11 transmits through the first grating 14, the X-ray that has transmitted forms images at a constant interval in the z-direction. These images are called self-images, and a phenomenon that the self-images are formed refers to the Talbot effect. In parallel to the first grating 14, the second grating 15 is arranged at a position where the self-images are formed, and a grating direction of the second grating 15 is slightly tilted from a position parallel to a grating direction of the first grating 14, and accordingly, a moire image is obtained by the X-ray that has transmitted through the second grating 15. When a subject H exists between the X-ray source 11 and the first grating 14, a phase of the X-ray deviates owing to the subject H, and accordingly, as shown in FIG. 10, interference fringes in the moire image M are disturbed at a margin of the subject H, which is taken as a boundary. This disturbance of the interference fringes is detected by processing the moire image M, whereby an image of the subject can be formed. This is the principle of the Talbot interferometer and the Talbot-Lau interferometer.

In the X-ray imaging apparatus 1, the multi-slit 12 is arranged at a position near the X-ray source 11 between the X-ray source 11 and the first grating 14, and the X-ray imaging by the Talbot-Lau interferometer is performed. The Talbot-Lau interferometer premises that the X-ray source 11 is an ideal point source; however, in the actual imaging, a focal point having a somewhat large focal point diameter is used, and accordingly, by the multi-slit 12, the X-ray source 11 turns to multiple light sources as if X-rays were irradiated while a plurality of the point sources continued with one another. This is the X-ray imaging method by the Talbot-Lau interferometer, and a similar Talbot effect to that in Talbot interferometer can be obtained even in the case where the focal point diameter is somewhat large.

In the conventional Talbot-Lau interferometer, the multi-slit 12 has been used for the purpose of turning the X-ray source 11 to the multiple light sources as described above and of increasing an exposure dose, and the first grating 14 or the second grating 15 has been relatively moved in order to obtain a plurality of the moire images. However, in this embodiment, the first grating 14 or the second grating 15 is not relatively moved, but the multi-slit 12 is moved with respect to the first grating 14 and the second grating 15 while keeping on fixing the positions of the first grating 14 and the second grating 15, whereby a plurality of the moire images at a constant cycle interval is obtained.

Note that, in the case of obtaining the moire image by the second imaging mode, the movement of the multi-slit 12 is not performed, but the imaging is performed once, or the imaging is performed twice while rotating the subject and the slit directions by 90°.

Figure 11:
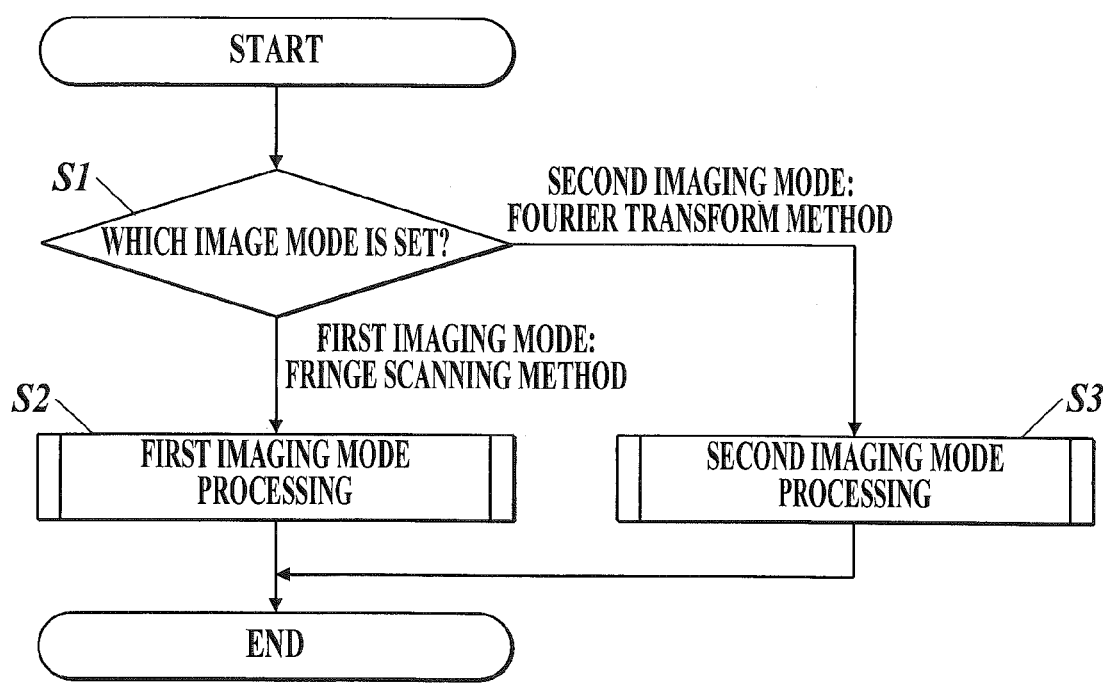
FIG. 11 is a flowchart showing imaging control processing by a control unit of the X-ray imaging apparatus.

FIG. 11 is a flowchart showing imaging control processing to be executed by the control unit 181 of the X-ray imaging apparatus 1. The imaging control processing is executed by cooperation between the control unit 181 and the programs stored in the storage unit 185.

First, based on the setting information received from the controller 5, it is determined which imaging mode of the first imaging mode (for the fringe scanning method) and the second imaging mode (for the Fourier transform method) is set (Step S1). When it is determined that the first imaging mode is set (Step S1; first imaging mode), first imaging mode processing is executed (Step S2). Meanwhile, when it is determined that the second imaging mode is set (Step S1; second imaging mode), second imaging mode processing is executed (Step S3).

Figure 12A:
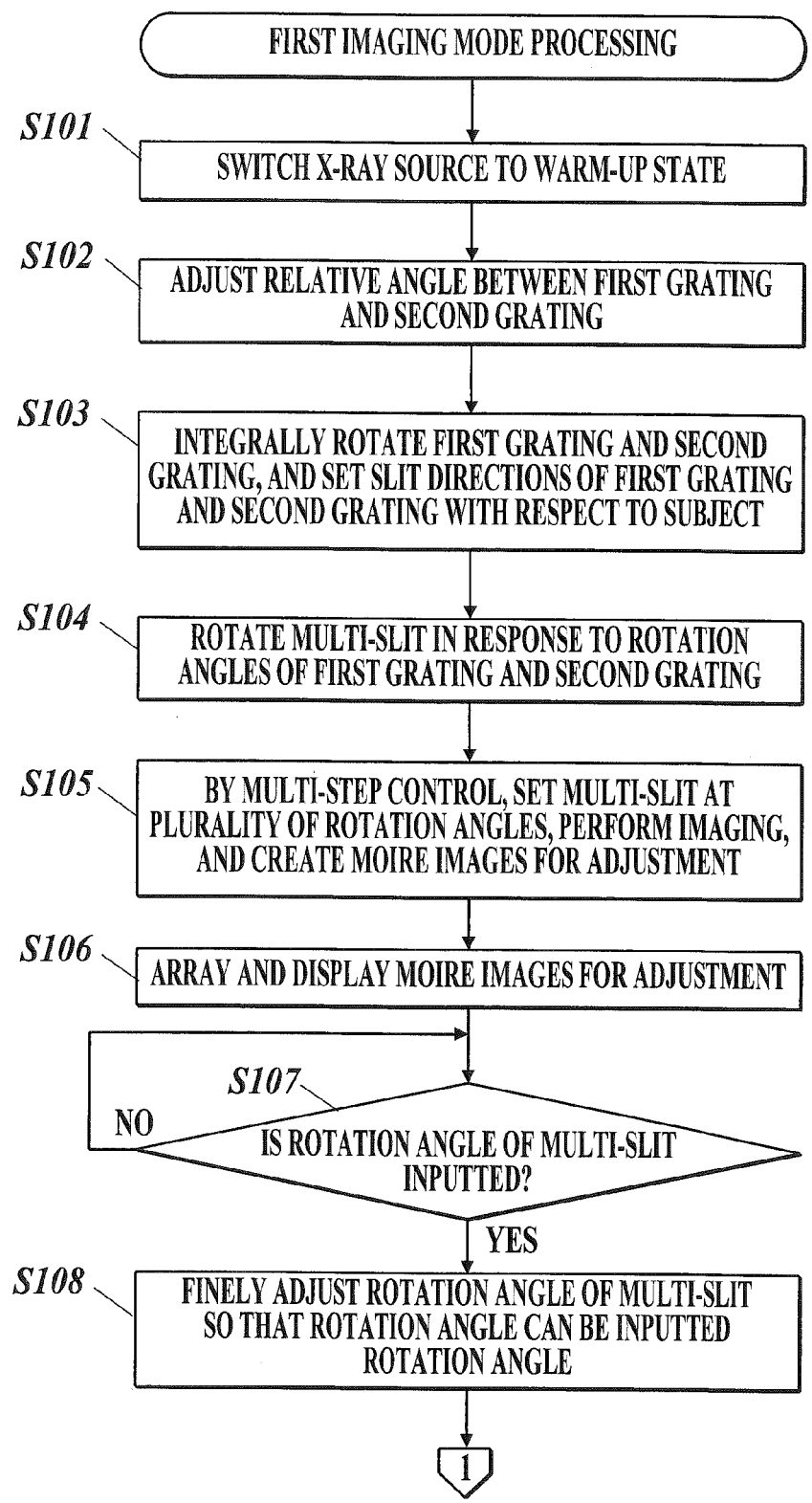
FIG. 12A is a flowchart showing first imaging mode processing to be executed in Step S2 of FIG. 11.
Figure 12B:
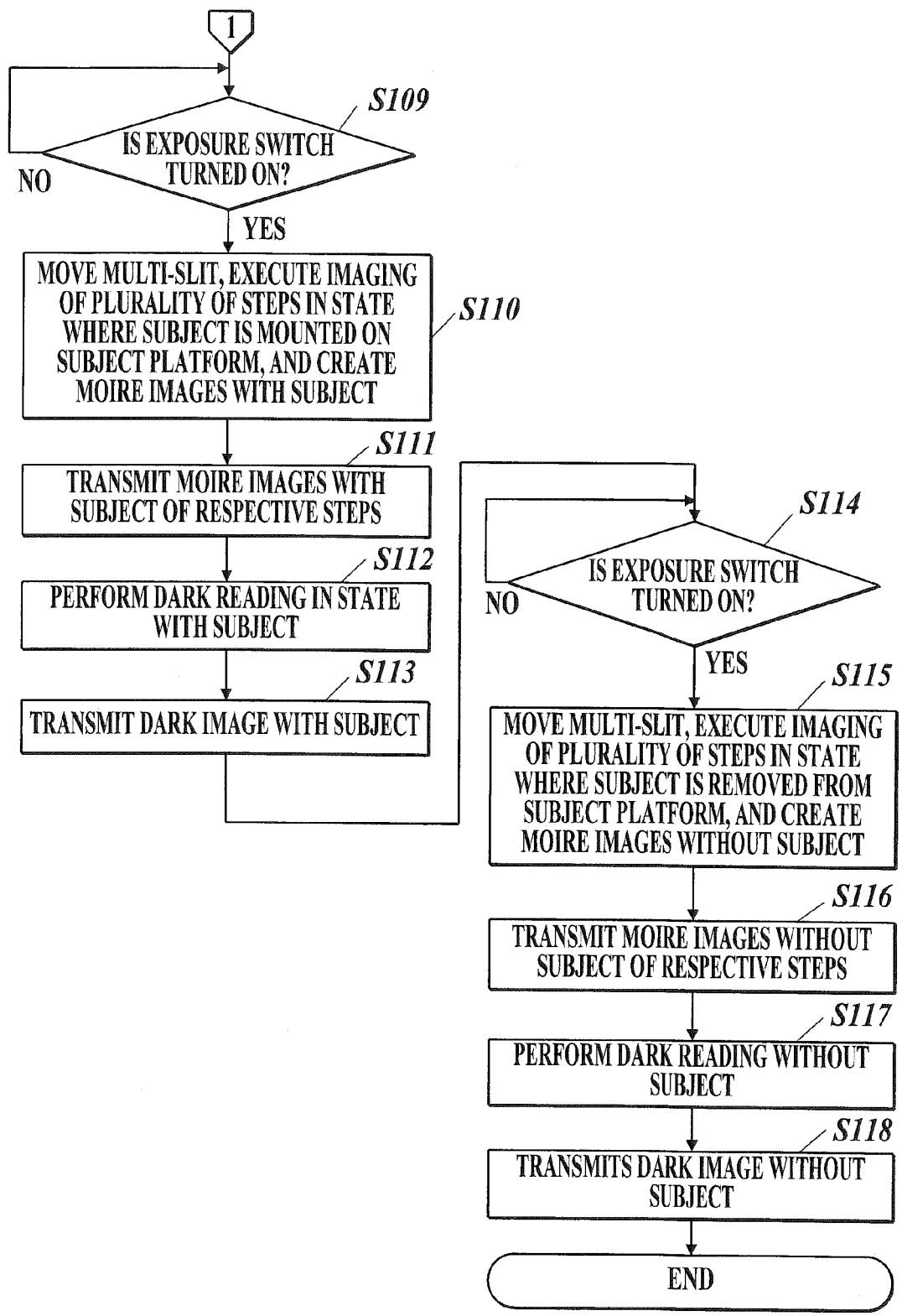
FIG. 12B is a flowchart showing the first imaging mode processing to be executed in Step S2 of FIG. 11.

FIGS. 12A and 12B are flowcharts showing the first imaging mode processing to be executed by the control unit 181 of the X-ray imaging apparatus 1 in Step S2 of FIG. 11. The first imaging mode processing is executed by cooperation between the control unit 181 and the programs stored in the storage unit 185.

Here, the above-mentioned X-ray imaging method by the Talbot-Lau interferometer is used for the X-ray imaging in the first imaging mode, and the fringe scanning method is used for the reconstruction of the subject image. In the X-ray image apparatus 1, the drive unit 122 is driven and stopped by the control of the control unit 181, whereby the multi-slit 12 is moved by a plurality of steps at an equal interval, the imaging is performed at each of the steps, and a moire image at each of the steps is obtained.

The number of steps is 2 to 20, preferably, 3 to 10. In terms of obtaining a reconstructed image with high visibility in a short time, the number of steps is preferably 5 (Reference Literature (1) K. Hibino, B. F. Oreb and D. I. Farrant, Phase shifting for nonsinusoidal waveforms with phase-shift error, J. Opt. Soc. Am. A, Vol. 12, 761-768 (1995), Reference Literature (2) A. Momose, W. Yashiro, Y. Takeda, Y. Suzuki and T. Hattori, Phase Tomography by X-ray Talbot Interferometry for biological imaging, Jpn. J. Appl. Phys., Vol. 45, 5254-5262 (2006)).

As shown in FIG. 12A and FIG. 12B, first, the X-ray source 11 is switched to a warm-up state by the control unit 181 (Step S101).

Subsequently, the relative angle adjusting unit 213 of the grating rotating unit 210 is controlled, and the first grating 14 is rotated so that the relative angle between the first grating 14 and the second grating 15 can be optimum for the first imaging mode (so that the protruding portion 142a can be located at the position of contacting the stopper 214). In such a way, the relative angle between the first grating 14 and the second grating 15 is adjusted (Step S102).

Subsequently, the first grating 14 and the second grating 15 are integrally rotated in response to the operation of the operator, and the slit directions of the first grating 14 and the second grating 15 with respect to the subject are set (Step S103). That is to say, the operator such as the radiographer rotates the handle 211 of the grating rotating unit 210, and sets the slit directions of the first grating 14 and the second grating 15 in response to the arrangement direction of the structure of interest in the subject, which is mounted on the subject platform 13. When the rotation of the handle 211 is stopped, and the position thereof is fixed by the engagement of the ball of the tray fixing member 171b, which is urged by the spring, then the sensing signal is outputted from any of the angle sensing sensors SE1 to SE4 to the control unit 181, and in the control unit 181, the rotation angle of the rotating tray 212 (that is, the first grating 14 and the second grating 15) of the grating rotating unit 210 from the home position, the rotation angle corresponding to the set slit directions, is obtained.

Subsequently, in response to such rotation angles of the first grating 14 and the second grating 15, the motor unit 121a of the multi-slit rotating unit 121 is controlled by a pulse, and the multi-slit 12 is rotated in response to the rotation angles of the first grating 14 and the second grating 15 (Step S104). For example, the pulse motor of the motor unit 121a is controlled, and the multi-slit 12 is rotated at a dash from the home position thereof by a rotation angle approximate to the rotation angle of the rotating tray 212 (for example, by a rotation angle of approximately 29° in the case where the rotating tray 212 is set at 30°).

Subsequently, the motor unit 121a is switched to micro-step precise control, and the imaging is performed at a plurality of the rotation angles while rotating the multi-slit 12 little by little, whereby the plurality of moire images for the adjustment are generated (Step S105). For example, in the case where the rotating tray 212 is set at 30°, then the multi-slit 12 is set at three rotation angles, which are 29.5°, 30° and 30.5°, a low-dose X-ray is irradiated thereto by the X-ray source 11, and the imaging is performed. In such a way, three moire images for the adjustment are obtained. Note that, in Step S105, the imaging is performed in a state where the subject is not mounted on the subject platform 13.

The plurality of moire images for the adjustment, which is imaged, is arrayed and displayed on the display unit 183 in association with the rotation angles of the multi-slit 12 (Step S106).

Here, as mentioned above, the relative angle between the first grating 14 and the second grating 15 is adjusted in Step S102 so that the number of interference fringes can be minimum, and accordingly, in Step S103, the first grating 14 and the second grating 15 are rotated by the rotation of the rotating tray 212 while keeping on maintaining the relative angle concerned. However, when the rotating tray, which mounts the first grating 14 and the second grating 15 thereon, rotates, and the relative angle between the multi-slit 12 and the first and second gratings 14 and 15 is changed, then the sharpness of the interference fringes (that is, moirés) is changed. Accordingly, it is necessary to adjust the relative angle between the multi-slit 12 and the first and second gratins 14 and 15, that is, the rotating tray 212 that mounts these thereon.

In general, as the relative angle between the multi-slit 12 and the first grating 14 is smaller, moire images of which interference fringes have higher sharpness are obtained. However, since the multi-slit 12 is arranged in the vicinity of the X-ray source 11 as a heat generation portion, the multi-slit 12 is prone to be affected by heat. Therefore, in consideration of deformation and the like of the multi-slit 12, it is effective not only to rotate the multi-slit 12 by the same angle as that of the rotating tray 212, but also to perform fine adjustment in Steps S105 to S108 by performing the micro-step drive for the motor unit 121a.

The operator observes the moire images displayed on the display unit 183 in step S106, and selects a rotation angle, at which the interference fringes are sharpest, as the rotation angle for use in the imaging. Note that, here, the sharpness of the interference fringes is visually observed by the operator; however, in the case where a maximum value in a sine curve (refer to FIG. 17) to be described later is MAX, and a minimum value therein is MIN, then a sharpness degree (definition) that indicates a degree of each of the sharpness of the interference fringes can be represented by the following expressions. The rotation angle, at which the sine curve takes the maximum value, may be set not by the operator but automatically by the program by using the sharpness degree of the interference fringe.

Sharpness degree of interference fringe=(MAX−MIN)/(MAX+MIN)=amplitude/average value When the rotation angle of the multi-slit 12 is inputted by the operation unit 182 (Step S107; YES), the motor unit 121a is driven again, and the position of the multi-slit 12 is finely adjusted so that the rotating angle of the multi-slit 12 from the home position thereof can be the inputted rotation angle (Step S108).

After the rotation angle of the multi-slit 12 is adjusted, when the subject is mounted on the subject platform 13, and the exposure switch is operated to be turned on by the operator (Step S109; YES), then the multi-slit 12 is moved in the slit arraying direction by the drive unit 122, and the imaging in the plurality of steps is executed, whereby a plurality of moire images with the subject is created (Step S110).

First, the irradiation of the X-ray by the X-ray source 11 is started in a state where the multi-slit 12 is stopped. After being reset, in the X-ray detector 16, the electric charges are accumulated at the timing of the X-ray irradiation, and the accumulated electric charges are read as the image signal at the timing when the X-ray irradiation is stopped. This is imaging equivalent to one step. At the timing when the imaging equivalent to one step is ended, the drive unit 122 is activated by the control of the control unit 181, and the movement of the multi-slit 12 is started. When the multi-slit 12 moves by a predetermined amount, then the movement of the multi-slit 12 is stopped in such a manner that the drive unit 122 is stopped, and imaging of a next step is performed. In such a way, the movement and stop of the multi-slit 12 are repeated by a predetermined number of steps, and when the multi-slit 12 is stopped, the irradiation of the X-ray and the reading of the imaging signal are performed. The read image signal is outputted as the moire image to the main body section 18.

For example, it is assumed that the slit cycle of the multi-slit 12 is 22.8 (μm), and that imaging of five steps is performed in 10 seconds. The imaging is performed every time when the multi-slit 12 moves by 4.56 (μm) corresponding to ⅕ of the slit cycle thereof and stops.

In the case of moving the second grating 15 (or the first grating 14) as heretofore, the slit cycle of the second grating 15 is relatively small, and a movement thereof in each step also becomes small; however, the slit cycle of the multi-slit 12 is relatively large, and a movement thereof in each step is also large. For example, with regard to the second grating 15 with a slit cycle of 5.3 (μm), a movement thereof in each step is 1.06 (μm), and meanwhile, with regard to the multi-slit 12 with a slit cycle of 22.8 (μm), a movement thereof in each step is 4.56 (μm), which is as large as approximately four times the movement of the second grating 15. In the case of using the same drive transmission system (including a drive source and a deceleration transmission system) and of performing the imaging by repeating the activation and stop of the drive unit 122 in the event of the imaging in each step, a ratio of an error in the movement owing to an influence of a backlash or the like of the drive unit 122 at the time of the activation and stop, the error occupying an actual movement corresponding to a controlled variable (number of drive pulses) of the pulse motor (a drive source) for the moving, becomes smaller in the method of moving the multi-slit 12 as in this embodiment. This indicates that it is easy to obtain a moire image following a sine curve to be described later, and that a high-definition reconstructed image can be obtained even when the activation and the stop are repeated. Alternatively, this indicates that, in the case where even an image in accordance with a conventional method is sufficiently suited for the diagnosis, accuracy (in particular, activation characteristics and stopping characteristics) of the entire drive transmission system including the motor (drive source) is alleviated, leading to the fact that it is possible to reduce cost of components composing the drive transmission system.

When the imaging in each step is ended, the moire image in each step is transmitted to the controller 5 from the communication unit 184 of the main body section 18 (Step S111), The moire mage with the subject is transmitted one by one to the controller 5 from the main body section 18 every time when the imaging in each step is ended.

Subsequently, the dark reading is performed in the X-ray detector 16, and a dark image (offset correction data) for correcting image data with the subject is obtained (Step S112). The dark reading is performed at least once. Alternatively, the dark reading may be performed several times, and an average value thereof may be obtained as a dark image. The dark image is transmitted from the communication unit 184 to the controller 5 (Step S113). The offset correction data that is based on the dark reading concerned is commonly used for the correction of each moire image signal.

Note that, with regard to such obtainment of the dark image, the dark reading of the step concerned may be performed after the moire image is obtained in each step, and offset correction data dedicated to each step may be created.

Subsequently, the processing turns to a waiting state for the operator to turn on the exposure switch (Step S114). Here, in order that the moire image without the subject can be created, the operator removes the subject from the subject platform 13, and evacuates the subject. When such preparation for the imaging without the subject is completed, the exposure switch is depressed.

When the exposure switch is depressed (Step S114; YES), the multi-slit 12 is moved in the slit direction thereof by the drive unit 122, and the imaging is executed without the subject in a plurality of steps, and a plurality of moire images without the subject is created (Step S115). When the imaging in each step is ended, the moire image in each step is transmitted to the controller 5 from the communication unit 184 of the main body section 18 (Step S116). The moire images without the subject are transmitted one by one to the controller 5 from the main body section 18 by the communication unit 184 every time when the imaging in each step is ended.

Subsequently, the dark reading is performed in the X-ray detector 16, and a dark image without the subject is obtained (Step S117). The dark reading is performed at least once. Alternatively, the dark reading may be performed a plurality of times, and an average value thereof may be obtained as a dark image. The dark image is transmitted from the communication unit 184 to the controller 5 (Step S118), and a series of the imaging for one imaging order is ended.

Note that, with regard to the obtainment of the dark image, the dark reading in each step may be performed after the moire image is obtained for each step, and offset correction data dedicated to each step may be created.

Note that, most preferably in terms of accuracy, the dark reading of the plurality of moire images without the subject is implemented immediately after the imaging of the moire images with the subject; however, data, which is obtained in advance, for example, at the time when the operation is started, may be used for the purpose of saving a time until the reconstruction of the subject image.

In the controller 5, when the moire images are received by the communication unit 54, the received moire images are stored in the storage unit 55 in association with the imaging order information designated at the time when the imaging is started.

Figure 13A:
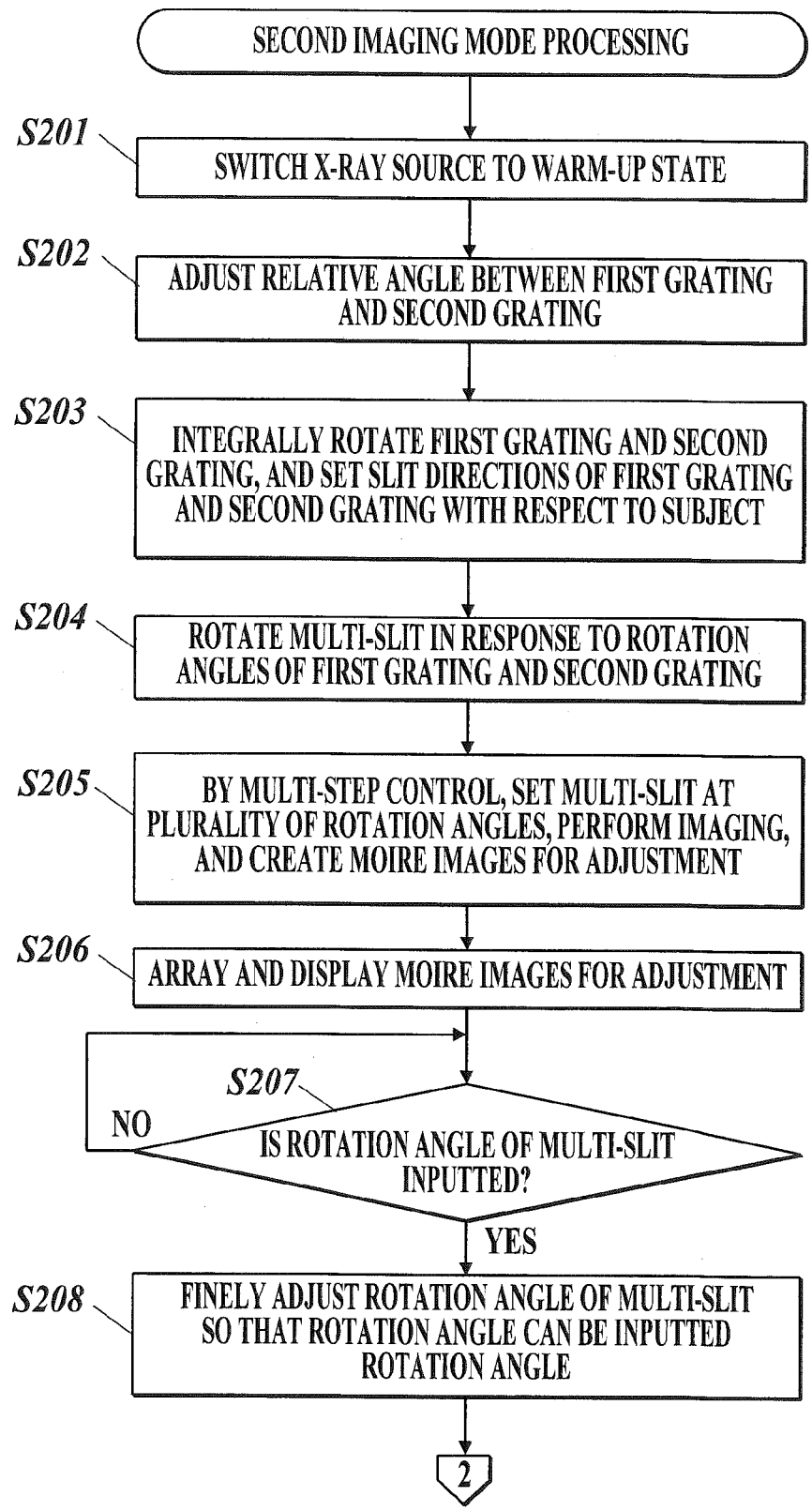
FIG. 13A is a flowchart showing second imaging mode processing to be executed in Step S3 of FIG. 11.
Figure 13B:
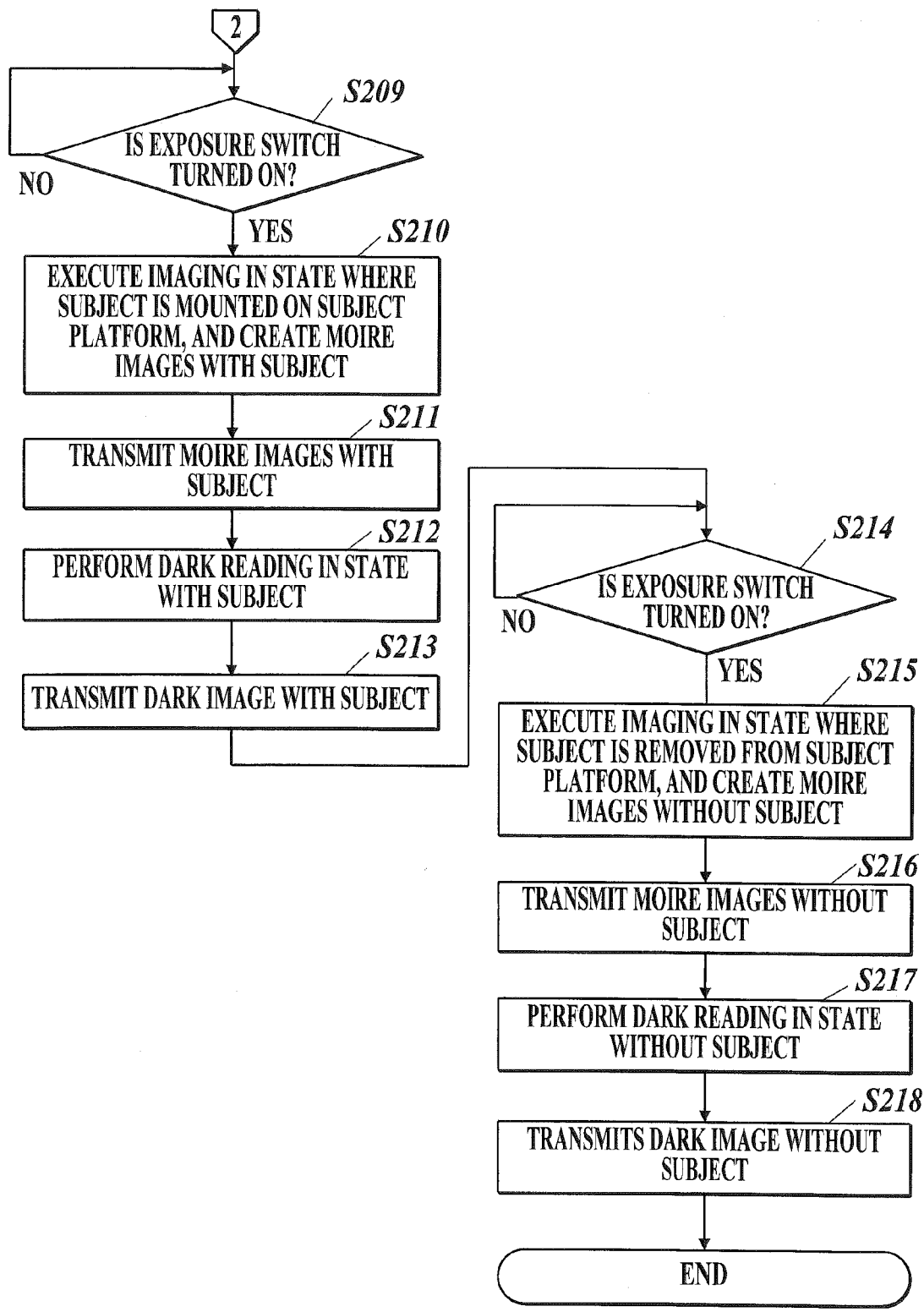
FIG. 13B is a flowchart showing the second imaging mode processing to be executed in Step S3 of FIG. 11.

FIGS. 13A and 13B are flowcharts showing the second imaging mode processing to be executed by the control unit 181 of the X-ray imaging apparatus 1 in Step S3 of FIG. 11. The second imaging mode processing is executed by cooperation between the control unit 181 and the programs stored in the storage unit 185.

As shown in FIG. 13A and FIG. 13B, first, the X-ray source 11 is switched to the warm-up state by the control unit 181 (Step S201).

Subsequently, the relative angle adjusting unit 213 of the grating rotating unit 210 is controlled, and the relative angle between the first grating 14 and the second grating 15 is adjusted so as to be optimum for the second imaging mode (so that the protruding portion 142a can be located at the position of rotating by a predetermined angle from the home position) (Step S202).

Subsequently, processing of Step S203 to Step S208 is performed. The processing of Steps S203 to S208 is similar to that described in Steps S103 to S108 in FIG. 12A, and accordingly, a description thereof is incorporated by reference.

When the subject is mounted on the subject platform 13, and the exposure switch is operated to be turned on by the operator (Step S209; YES), then the imaging is executed, and a moire image with the subject is created (Step S210). That is to say, a radiation is irradiated from the X-ray source 11, and reading thereof is performed in the X-ray detector 16. Note that, in the second imaging mode, imaging of only one piece is performed in a state where the drive unit 122 is left stopped and the multi-slit 12 is not moved.

When the imaging is ended, the moire image obtained by the imaging is transmitted to the controller 5 from the communication unit 184 of the main body section 18 (Step S211).

Subsequently, dark reading is performed in the X-ray detector 16, and a dark image (offset correction data) for correcting image data with the subject is obtained (Step S212). The dark reading is performed at least once. Alternatively, the dark reading may be performed a plurality of times, and an average value thereof may be obtained as a dark image. The dark image is transmitted from the communication unit 184 to the controller 5 (Step S213). The offset correction data that is based on the dark reading concerned is commonly used for the correction of the moire image signal.

Subsequently, the processing turns to a waiting state for the operator to turn on the exposure switch (Step S214). Here, in order that the moire image without the subject can be created, the operator removes the subject from the subject platform 13, and evacuates the subject. When such preparation for the imaging without the subject is completed, the exposure switch is depressed.

When the exposure switch is depressed (Step S214; YES), the imaging is executed without the subject, and the moire image without the subject is created (Step S215). In a similar way to Step S210, also in Step S215, such imaging of only one piece is performed in a state where the drive unit 122 is left stopped and the multi-slit 12 is not moved.

When the imaging is ended, the moire image is transmitted to the controller 5 from the communication unit 184 of the main body section 18 (Step S216).

Subsequently, the dark reading is performed in the X-ray detector 16, and a dark image without the subject is obtained (Step S217). The dark reading is performed at least once. Alternatively, the dark reading may be performed a plurality of times, and an average value thereof may be obtained as a dark image. The dark image is transmitted from the communication unit 184 to the controller 5 (Step S218), and a series of the imaging for one imaging order is ended.

Note that, most preferably in terms of accuracy, the dark reading of the plurality of moire images without the subject is implemented immediately after the imaging of the moire image with the subject; however, data, which is obtained in advance, for example, at the time when the operation is started, may be used for the purpose of saving a time until the reconstruction of the subject image.

In the control unit 51 of the controller 5, when the moire image is received by the communication unit 54, the reconstructed image creation/display processing by the fringe scanning method is executed in the case where the imaging mode set in the imaging order information, which is a processing target at present, is the first imaging mode, and the reconstructed image creation/display processing by the Fourier transform method is executed in the case where the imaging mode thus set is the second imaging mode.

FIGS. 14A and 14B are flowcharts showing the reconstructed image creation/display processing by the fringe scanning method to be executed by the control unit 51. The reconstructed image creation/display processing by the fringe scanning method is executed by cooperation between the control unit 51 and the programs stored in the storage unit 55.

First, in Steps S11 to S13, for each of the plurality of moire images with the subject, and for each of the plurality of moire images without the subject, correction processing for correcting variations among the respective pixels of the X-ray detector 16 is performed. Specifically, offset correction processing (Step S11), gain correction processing (Step S12), and defective pixel correction processing (Step S13) are executed.

In Step S11, based on the dark image for the correction of the image data with the subject, offset correction is implemented for each of the moire images with the subject. Based on the dark image for the correction of the image data without the subject, offset correction is implemented for each of the moire images without the subject. In Step S12, gain correction data corresponding to the X-ray detector 16 used for the imaging is read out from the storage unit 55, and gain correction is implemented for each of the moire images based on the readout gain correction data.

In Step S13, the defective pixel map (data indicating positions of the defective pixels) corresponding to the X-ray detector 16 used for the imaging is read out from the storage unit 55, and a value (signal value) of a pixel in each moire image, which is located at a position indicated by the defective pixel position map, is interpolated by peripheral pixels, and is calculated.

Subsequently, X-ray intensity fluctuation correction (trend correction) is performed among a plurality of the moire images (Step S14). In the fringe scanning method, one reconstructed image is created based on the plurality of moire images. Therefore, if there are fluctuations (variations) in intensity of the X-ray to be irradiated in the imaging of each moire image, then a fine reconstructed image cannot be obtained, leading to a possibility that a minute signal change may be overlooked. Accordingly, in Step S14, processing for correcting a signal value difference owing to the X-ray intensity fluctuations among the plurality of moire images at the imaging time is performed.

As specific processing, any of the following may be used, which is: a method of performing the correction by using a signal value of a pixel at one point predetermined in each moire image; a method of correcting (performing one-dimensional correction) a signal value difference in a predetermined direction of the X-ray detector 16 among the respective moire images; and a method of correcting (performing two-dimensional correction) a signal value difference in a two-dimensional direction among the respective moire images.

Figure 15:
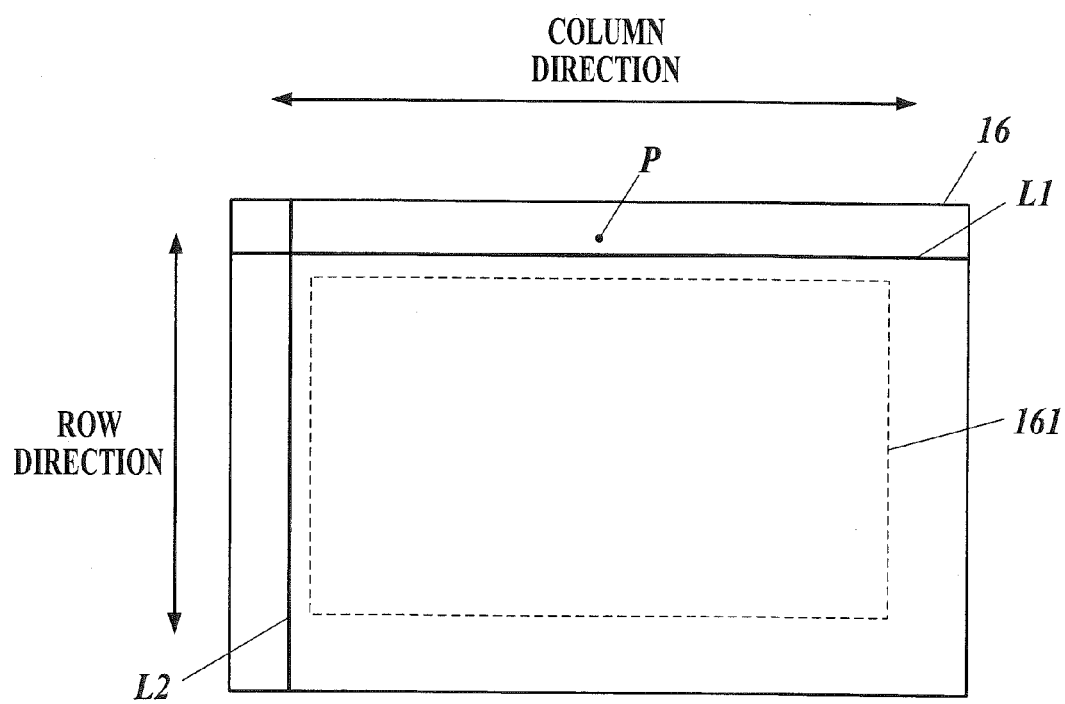
FIG. 15 is a view for explaining correction of X-ray intensity variations among a plurality of moire images.

In the method of performing the correction by using a signal value of a pixel at one point, first, as shown in FIG. 15, for each of the plurality of moire images, a signal value of a pixel located at a predetermined position P directly corresponding to an X-ray region outside of the moire image region (subject arrangement region) 161 of the X-ray detector 16 is obtained. Subsequently, a first moire image (for example, a moire image with the subject, which is imaged at first) is standardized by an average signal value of pixels at the position P in a second moire images and after, which are obtained as described above, and a correction coefficient of each of the second moire images and after is calculated based on a value at the position P after such standardization. Then, each of the second moire images and after is multiplied by the correction coefficient, whereby the X-ray intensity variations are corrected. In this correction method, overall variations in the X-ray intensity among the respective pieces of the imaging can corrected with ease. Note that sensing means such as a sensor for sensing the X-ray exposure dose may be provided on a back side of the X-ray detector 16, and the signal value difference caused by the variations in X-ray intensity at the imaging time among the respective moire images can be corrected base on the X-ray exposure dose at the time of imaging each of the moire images, the X-ray exposure dose being outputted from the sensing means.

In the one-dimensional correction, first, for each of the plurality of moire images, an average signal value of pixels in a predetermined row L1 (the row is directed in a reading line direction in the X-ray detector 16) is calculated. Next, the first moire image is standardized by the average signal value of the pixels in the second moire image and after, and a correction coefficient in the row direction of each of the moire images which are the second moire image and after is calculated based on a signal value of each pixel in the row L1 after such standardization, and on a signal value of each pixel in rows L1 of the second moire image and after. Then, each of the second moire images and after is multiplied by the correction coefficient corresponding to the position in the row direction, whereby X-ray intensity variations in the row direction are corrected. In this correction method, the X-ray intensity variations in the one-dimensional direction among the respective pieces of the imaging can be corrected with ease. For example, in a certain pieces of the imaging, in the case where a time rag occurs between the irradiation timing by the X-ray source 11 and the reading timing of the X-ray detector 16, X-ray intensity variations in a reading line direction of the X-ray detector 16, the variations being caused by the time rag, can be corrected.

In the two-dimensional correction, first, for each of the plurality of moire images, average signal values of pixels in predetermined row L1 and column L2 (the column is directed in a direction perpendicular to the reading line direction in the X-ray detector 16) are calculated. Subsequently, the first moire image is standardized by average signal values of pixels in the rows L1 of the second moire image and after, and a correction coefficient in the row direction of each of the second moire images and after is calculated based on signal values of the respective pixels in the row L1 after such standardization and signal values of the respective pixels of the second row L1 and after. In a similar way, the first moire image is standardized by average signal values of pixels in the column L2 of the second moire image and after, and a correction coefficient in the column direction of each of the second moire images and after is calculated based on signal values of the respective pixels in the column L2 after such standardization and signal values of the respective pixels of the second column L2 and after. Then, the correction coefficients in the row direction and the column direction are multiplied by each other, and a correction coefficient of each pixel in each of the second moire image and after is calculated. Then, each pixel is multiplied by the correction coefficients in the row direction and the column direction, whereby X-ray intensity variations in the two-dimensional direction are corrected. In this correction method, X-ray intensity variations in the two-dimensional direction among the respective pieces of the imaging can be corrected with ease.

Figure 16:
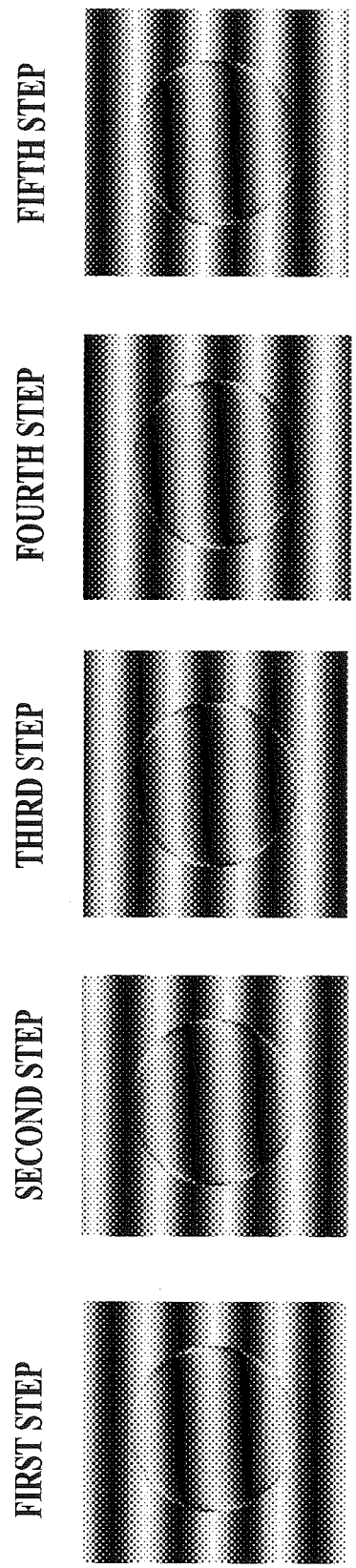
FIG. 16 is a view showing moire images to be obtained by imaging of five steps.
Figure 17:
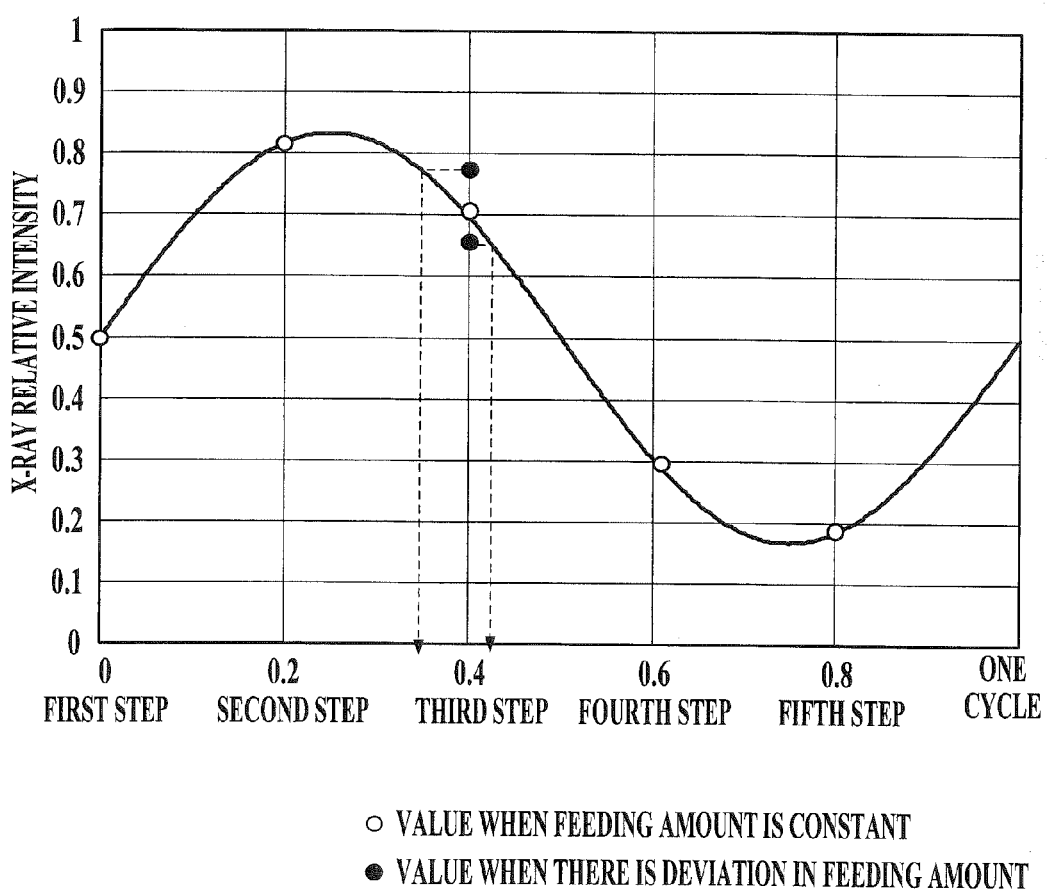
FIG. 17 is a graph showing X-ray relative intensities of pixels of interest of the moire images of the respective steps.

Subsequently, analysis of the moire images is performed (Step S15), and it is determined whether or not the moire images can be used for creating the reconstructed image (Step S16). In the case where the multi-slit 12 can be moved by a constant feeding amount with ideal feeding accuracy, then as shown in FIG. 16, five moire images for one slit cycle of the multi-slit 12 can be obtained by performing imaging in five steps. The moire image of each step is a result of performing fringe scanning at every constant cycle interval which is 0.2 cycle. Accordingly, when attention is paid to one arbitrary pixel in each moire image, X-ray relative intensity obtained by normalizing a signal value thereof forms a sine curve as shown in FIG. 17. Hence, the controller 5 obtains the X-ray relative intensity by paying attention to a certain pixel in the obtained moire image in each step. If the X-ray relative intensity obtained from each of the moire images forms a sine curve as shown in FIG. 17, then this represents that the moire images at the constant cycle interval are already obtained, and accordingly, it can be determined that the moire images can be used for the creation of the reconstructed image.

Note that a shape of the sine curve described above depends on the opening width of the multi-slit 12, the cycles of the first grating 14 and the second grating 15, and an inter-grating distance between the first grating and the second grating. Moreover, the shape concerned becomes a triangular wave shape in the case of coherent light such as radiation light; however, the shape concerned takes a sine curve since the X-ray functions as semi-coherent light owing to the multi-slit effect. The analysis of Step S15 is performed for each of the moire images with the subject and for each of the moire images without the subject.

In the case where there is a moire image, which cannot form the sine curve, among the moire images of the respective steps, it is determined that such a moire image cannot be used for the creation of the reconstructed image (Step S16; NO), and control information for instructing to change the imaging timing and to perform re-imaging is transmitted from the controller 5 to the X-ray imaging apparatus 1 (Step S17). For example, as shown in FIG. 17, in the case where a moire image is obtained at 0.35 cycle owing to cycle deviation while the third step is originally set at 0.4 cycle, then it is conceived that a cause thereof is degradation in feeding accuracy in the drive unit 122 (for example, superimposition of noise on a drive pulse of the pulse motor, and the like). Hence, the re-imaging just needs to be instructed to perform imaging only of the third step by setting the timing for the imaging earlier by 0.05 cycle. Alternatively, there may be issued such an instruction to perform the re-imaging for all of the five steps, and only for the third step, to set the timing for the imaging earlier by 0.05 cycle. In the case where all of the moire images in the five steps are deviated from the sine curve by a predetermined amount, there may be issued such an instruction to increase or decrease the number of drive pulses from the activation of the drive unit 122 to the stop thereof.

In the X-ray imaging apparatus 1, the imaging timing is adjusted in accordance with the control information concerned, and the re-imaging is executed.

Meanwhile, in the case where it is determined that the moire image can be used for the creation of the reconstructed image (Step S16; YES), then the creation of the reconstructed image with the subject and the reconstructed image without the subject is performed by using the pluralities of respective moire images with the subject and without the subject (Step S18 to Step S20).

Specifically, the interference fringes of the plurality of moire images are added together, whereby an absorption image (X-ray absorption image) is created (Step S18). Moreover, the phases of the interference fringes are calculated by using the principle of the fringe scanning method, and a differential phase image is created (Step S19). Furthermore, the visibility of the interference fringes is calculated by using the principle of the fringe scanning method (Visibility=2× amplitude/average value), and a small-angle scattering image is created (Step S20).

Subsequently, correction processing for removing the phases of the interference fringes from the reconstructed image with the subject and removing image non-uniformity (artifact) therefrom is performed by using the reconstructed image without the subject (Step S21). The processing of Step S21 includes processing for removing image non-uniformity (artifact) including non-uniformity in an X-ray dose distribution, which is caused by the change of the slit directions of the multi-slit 12, the first grating 14 and the second grating 15 at the time of the imaging, non-uniformity in a dose distribution, which is caused by manufacture variations in the slits, and non-uniformity caused by unexpected appearance of mainly the subject holder 130 in the image.

For example, in the case where the reconstructed image with the subject is a differential phase image, there is performed processing for subtracting a signal value of each pixel of the differential phase image without the subject from a signal value of each pixel of the differential phase image with the subject, the signal value (of the pixel at the same position) corresponding to the signal value of the differential phase image without the subject (refer to Publicly Known Literature (A); Timm Weitkamp, Ana Diazand, Christian David, franz Pfeiffer and Marco Stampanoni, Peter Cloetens and Eric Ziegler, X-ray Phase Imaging with a grating interferometer, OPTICSEXPRESS, Vol. 13, No. 16, 6296-6004 (2005), Publicly Known Literature (B); Atsushi Momose, Wataru Yashiro, Yoshihiro Takeda, Yoshio Suzuki and Tadashi Hattori, Phase Tomography by X-ray Talbot Interferometry for Biological Imaging, Japanese Journal of Applied Physics, Vol. 45, No. 6A, 2006, pp. 5254-5262 (2006)).

In the case where the reconstructed image with the subject is an absorption image or a small-angle scattering image, then as described in Publicly Known Literature (C), there is performed division processing for dividing the signal value of each pixel in the reconstructed image with the subject by a signal value of each pixel, which corresponds thereto, in the reconstructed image without the subject (Publicly Known Literature (C); F. Pfeiffer, M. Bech, O. Bunk, P. Kraft, E. F. Eikenberry, C H. Broennimann, C. Grunzweig, and C. David, Hard-X-ray dark-field imaging using a grating interferometer, nature materials Vol. 7, 134-137 (2008)).

Even if there is not only non-uniformity in the X-ray dose distribution, which is caused by the change of the respective gratings, which are the slit directions of the multi-slit 12, the first grating 14 and the second grating 15, and by characteristics of the subject platform, but also variations among characteristics of the individual pixels in the X-ray detector 16 for use in the imaging, the above-described processing is preferable since influences from the above-described non-uniformity and variations can be removed thereby. Hence, even if the slit direction is varied in response to the subject, an arrangement direction of the X-ray detector 16 with respect to the subject can be fixed (the position is not changed), and a display orientation of the subject in the reconstructed image which is to be displayed on the controller 5 always becomes in the same direction on the controller display screen. Accordingly, it becomes unnecessary to perform the operation of aligning the orientation of the reconstructed image in the controller 5 in the case of performing the comparison and interpretation of the image concerned with the pas images in the process of such follow-up and the like, and this is more preferable.

Figure 18A:
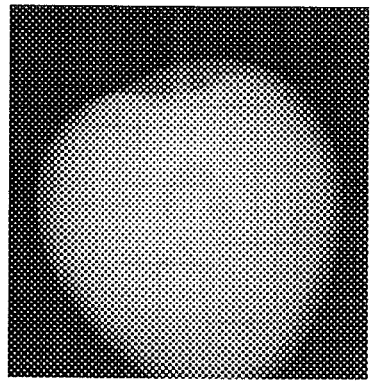
FIG. 18A is a view showing an example of an absorption image.
Figure 18B:
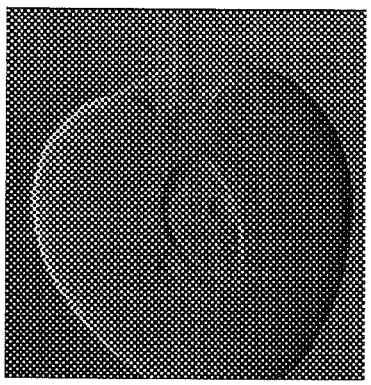
FIG. 18B is a view showing an example of a differential phase image.
Figure 18C:
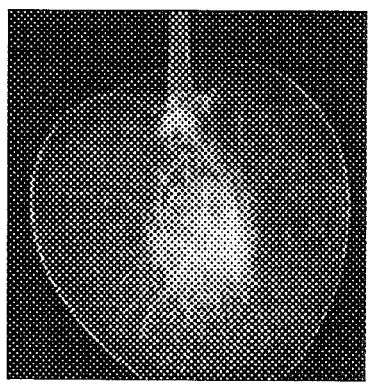
FIG. 18C is a view showing an example of a small-angle scattering image.

FIG. 18A to FIG. 18C show an example of the reconstructed images created by the fringe scanning method based on moire images obtained by imaging a cherry taken as a subject. FIG. 18A is an absorption image, FIG. 18B is a differential phase image, and FIG. 18C is a small-angle scattering image.

As shown in FIG. 18A, the absorption image has a feature in representing a large structural change of the subject. As shown in FIG. 18B, the differential phase image has a feature in representing a phase change of a margin of a subject tissue. As shown in FIG. 18, the small-angle scattering image has a feature in representing scattering in the subject tissue.

When the processing of step S21 is ended, the reconstructed images thus created are displayed on the display unit 53 (Step S22).

Figure 19:
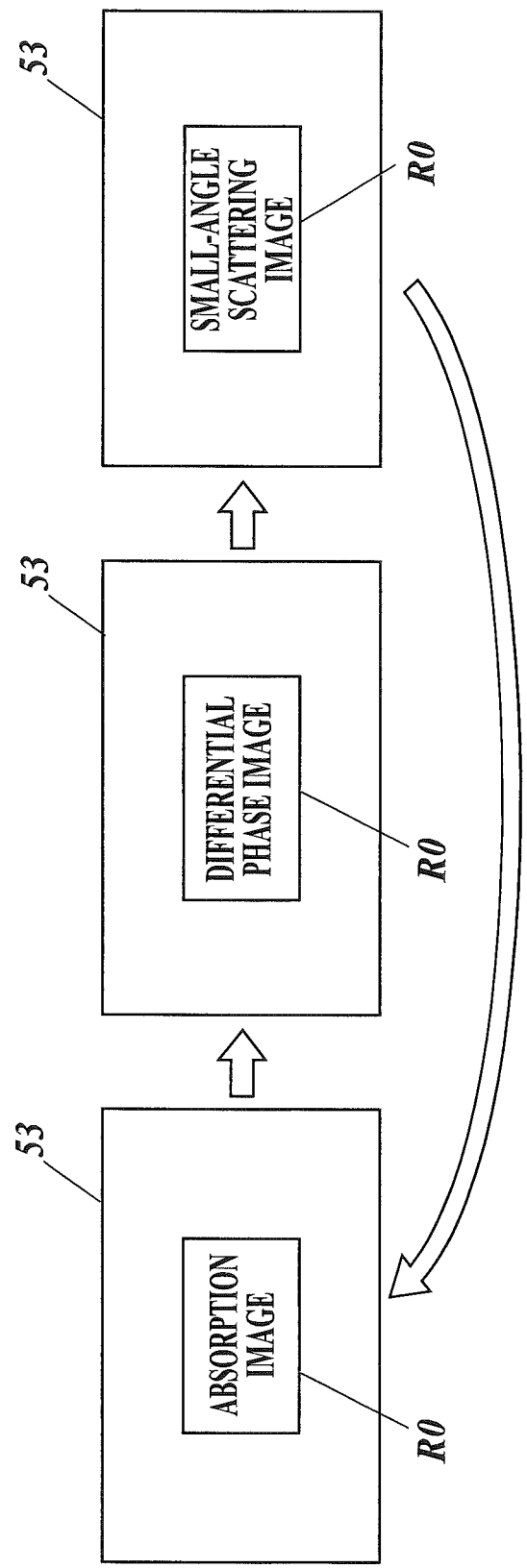
FIG. 19 is a view showing an example of a display method in an event of displaying the reconstructed image on the display unit in step S22 of FIG. 14B.

FIG. 19 shows an example of a display method in an event of displaying the reconstructed images on the display unit 53 in step S22. As shown in FIG. 19, in Step S22, there images, which are the absorption image, the differential phase image and the small-angle scattering image, are displayed on the same position (region R0) of the display unit 53 while being sequentially switched at every predetermined time.

The three images, which are the absorption image, the differential phase image and the small-angle scattering image, the images being created by the processing from Step S11 to Step S21, are those created by different pieces of processing from the imaged images (moire images) obtained by a single imaging set. Accordingly, as shown in FIGS. 18A to 18C, the positions of the subject in the three images are the same, and the three images individually have information of different features in the subject. Hence, as shown in FIG. 19, if the three images are displayed on the same position (region R0) of the display unit 53 while being sequentially switched at every predetermined time, then it is unnecessary for the physician who performs the interpretation to move a line of sight thereof, and a fatigue is not induced. Accordingly, the physician can perform the interpretation while maintaining a high degree of concentration. Moreover, by an afterimage effect (a so-called subliminal effect) in the event where the images are switched at every predetermined time, the physician becomes capable of reconstructing the plural pieces of information (features) regarding the subject in his/her brain, and becomes capable of carrying out the highly accurate diagnosis.

Note that, in FIG. 19, the three images, which are the absorption image, the differential phase image and the small-angle scattering image, are circularly displayed while being sequentially switched in this order; however, a display order of the images is not limited to this. Moreover, the number of images to be displayed just needs to be two types or more, and for example, the absorption image and the differential phase image may be displayed while being alternately switched, the differential phase image and the small-angle scattering image may be displayed while being alternately switched, or the absorption image and the small-angle scattering image may be displayed while being alternately switched. As mentioned above, the types of the images to be displayed in such a switched manner and the switching timing of the images can be preset for each of the regions and for each of the users. Moreover, preferably, on the screen outside of the image region of the display unit 53, a top button, a pause button and the like are provided, whereby it is made possible to continuously display any image in a static state in response to the operation of the operation unit 52.

Moreover, in Step S22, in addition to the reconstructed images for the diagnosis (that is, diagnostic images) obtained by the imaging performed this time, reference images may be displayed in combination. For example, as shown in FIG. 20, first, two types or more of the diagnostic images are circularly displayed on a region R1 while being sequentially switched at every predetermined time. When a shift to the next display is instructed from the operation unit 52, the reference images of the same type as that of the displayed diagnostic image are circularly displayed on a region R2 while being sequentially switched at every predetermined time. The reference images are images which the physician refers to in the event of interpreting the diagnostic images, and for example, are a reconstructed image by the fringe scanning method, which is imaged previously in the X-ray imaging apparatus 1 with regard to the same imaged region of the same patient, and a reconstructed image by the fringe scanning method with regard to a typical case. When an instruction for the parallel display is issued from the operation unit 52, the same type of diagnostic image and reference image (for example, an absorption image and an absorption image, a differential phase image and a differential phase image, and a small-angle scattering image and a small-angle scattering image) are arrayed and displayed on the regions R1 and R2 while being sequentially switched. In this case, the type of images to be displayed may be switched in response to a switching instruction from the operation unit 52. Moreover, the same types of images may be arrayed left and right, and all the types of images may be displayed on one screen. The circular display of the reference images may be performed before the circular display of the diagnostic images.

Next, a description is made of the creation and display of the reconstructed image by the Fourier transform method.

FIG. 21 is a flowchart showing reconstructed image creation/display processing by the Fourier transform method, which is to be executed by the control unit 51. The reconstructed image creation/display processing by the Fourier transform method is executed by cooperation between the control unit 51 and the programs stored in the storage unit 55.

First, in Steps S31 to S33, for each of the plurality of moire images with the subject, and for each of the plurality of moire images without the subject, correction processing for correcting variations among the respective pixels of the X-ray detector 16 is performed. Specifically, offset correction processing (Step S31), gain correction processing (Step S32), and defective pixel correction processing (Step S33) are executed. Contents of the respective pieces of processing are similar to those described in Steps S11 to S13 of FIG. 14A, and accordingly, a description thereof is incorporated by reference.

Subsequently, X-ray intensity fluctuation correction (trend correction) is performed among the moire images with the subject and the moire images without the subject (Step S34). Specific processing contents of the X-ray intensity fluctuation correction are similar to those described in Step S14 of FIG. 14A, and accordingly, a description thereof is incorporated by reference.

Subsequently, in processing of Step S35 and after, the creation of the reconstructed images of the subject by the Fourier transform method is performed. The creation of the reconstructed images by the Fourier transform method can be performed by a publicly known method (refer to Non-Patent Literature 1).

Figure 22A:
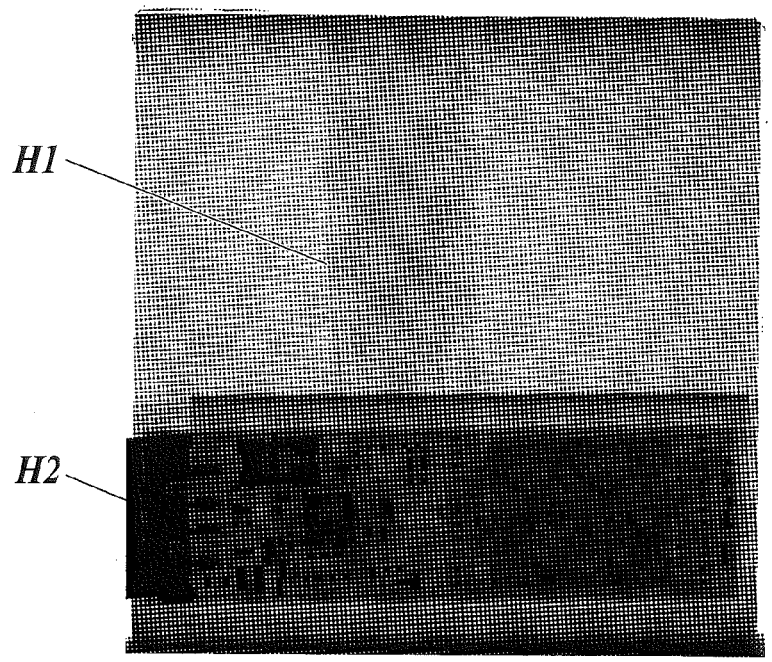
FIG. 22A is a view showing an example of a moire image with a subject, the image being imaged in a second imaging mode.
Figure 22B:
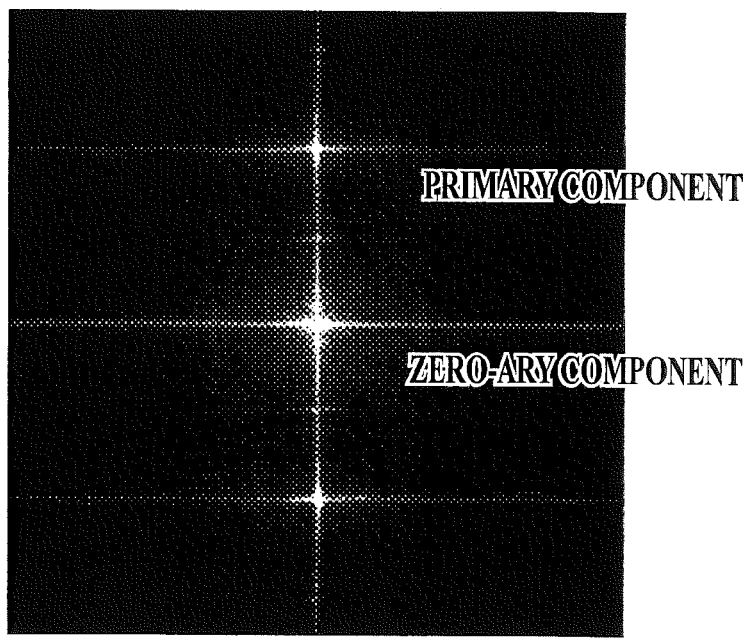
FIG. 22B is a view showing a result of performing two-dimensional Fourier transform for the moire image of FIG. 22A.
Figure 23A:
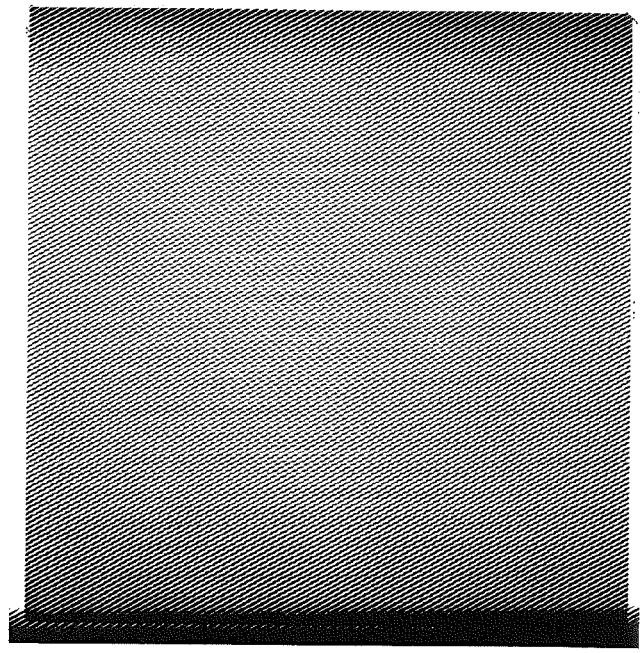
FIG. 23A is a view showing an example of a moire image without the subject, the imaging being imaged in the second imaging mode.
Figure 23B:
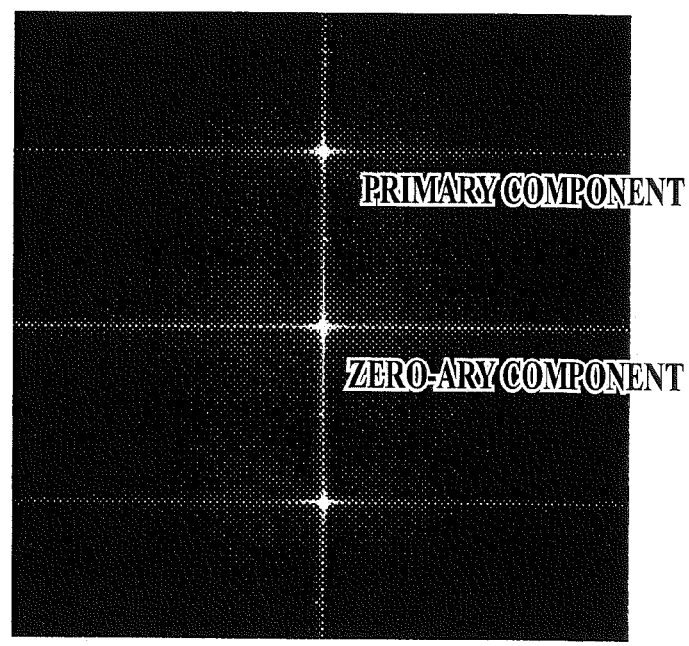
FIG. 23B is a view showing a result of performing the two-dimensional Fourier transform for the moire image of FIG. 23A.

First, each of the moire images with the subject and the moire images without the subject, which are already corrected, is subjected to the Fourier transform (two-dimensional Fourier transform) (Step S35). FIG. 22A shows an example of the moire image with the subject, which is imaged in the second imaging mode. Reference symbol H1 in FIG. 22A denotes a felt-tip pen, and reference symbol H2 therein denotes a USB memory. FIG. 22B shows a result of performing the two-dimensional Fourier transform for the moire image of FIG. 22A. FIG. 23A shows an example of the moire image without the subject, which is imaged in the second imaging mode. FIG. 23B shows a result of performing the two-dimensional Fourier transform for the moire image of FIG. 23A. Calculation results after the Fourier transform are complex numbers, and accordingly, in each of FIG. 22B and FIG. 23B, a norm (amplitude) between a real part and an imaginary part is displayed.

As shown in each of FIG. 22B and FIG. 23B, when one moire image is subjected to the Fourier transform, a low-frequency component (referred to as a zero-ary component) and a component (referred to as a primary component) in the vicinity of an interference fringe frequency are obtained in line, or in addition to the zero-ary component and the primary component, a high-frequency component (depending on the coherence of the X-ray imaging apparatus 1) is further obtained in line thereto. A direction where the zero-ary component and the primary component are thus arrayed is related to a direction of the fringes of the moire image, and becomes substantially orthogonal to the direction of the fringes of the moire image.

Here, a description is made of a relationship between grating orientations (slit directions) of the multi-slit 12, the first grating 14 and the second grating 15 and orientations where the interference fringes, the zero-ary component and the primary component are arrayed.

Figure 24:
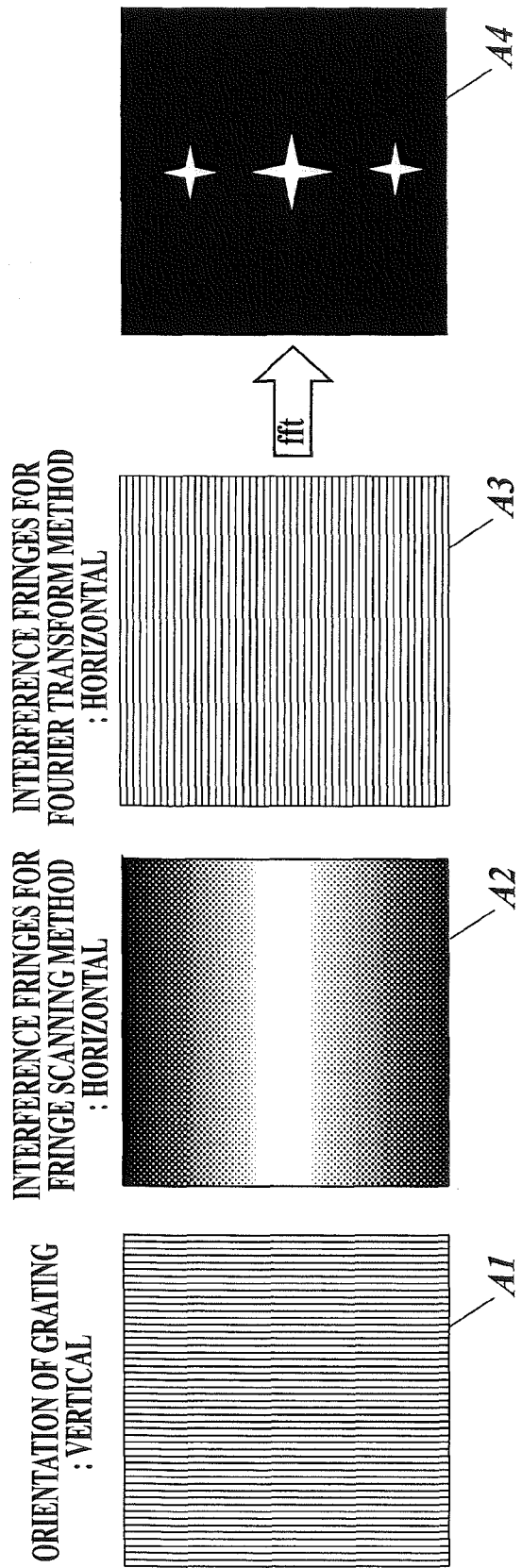
FIG. 24 is a view showing a grating direction when a slit direction of the grating is arranged longitudinally, interference fringes imaged in the first imaging mode, interference fringes imaged in the second imaging mode, and a result of performing Fourier transform for the interference fringes imaged in the second imaging mode.

For example, as shown by reference symbol A1 of FIG. 24, in the case where the grating orientations of the multi-slit 12, the first grating 14 and the second grating 15 are vertical, fringes of the moire image (an image obtained by slightly tilting the second grating with respect to the first grating 14) become horizontal as shown by reference symbol A2 of FIG. 24. As shown by reference symbol A3 of FIG. 24, fringes of the moire image (an image obtained by further tilting the second grating) for the Fourier transform become finer horizontal fringes in comparison with those denoted by reference symbol A2 of FIG. 24. As shown by reference symbol A4 of FIG. 24, an image obtained by performing the Fourier transform for the moire image for the Fourier transform becomes an image in which the zero-ary component and the primary component are arrayed vertically.

Figure 25:
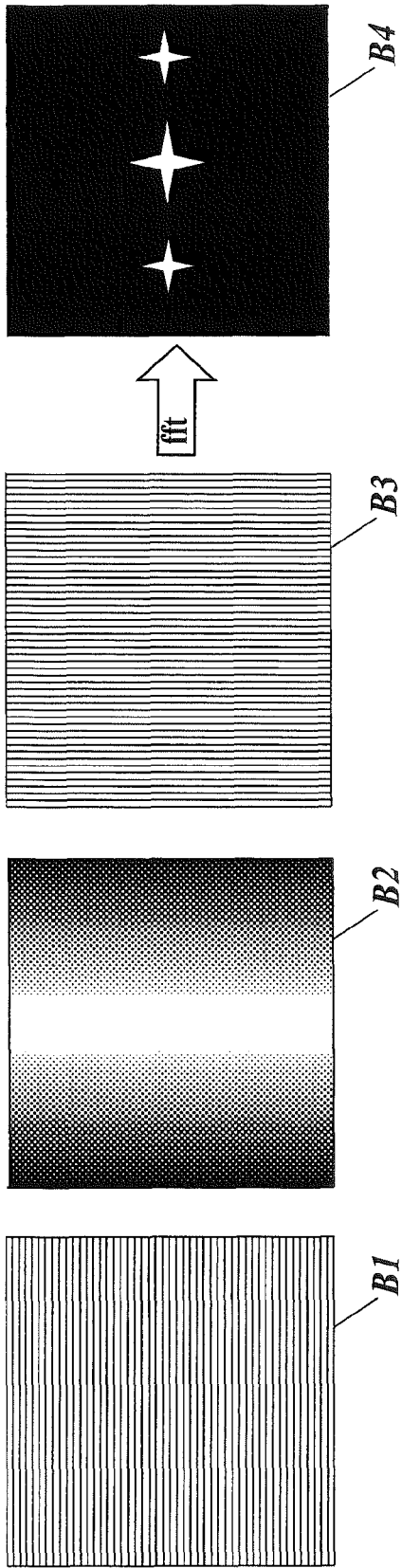
FIG. 25 is a view showing a grating direction when the slit direction of the grating is arranged laterally, interference fringes imaged in the first imaging mode, interference fringes imaged in the second imaging mode, and a result of performing the Fourier transform for the interference fringes imaged in the second imaging mode.

As shown by reference symbol B1 of FIG. 25, in the case where the grating orientations of the multi-slit 12, the first grating 14 and the second grating 15 are horizontal, fringes of the moire image (an image obtained by slightly tilting the second grating with respect to the first grating 14) become vertical as shown by reference symbol B2 of FIG. 25. As shown by reference symbol B3 of FIG. 25, fringes of the moire image (an image obtained by further tilting the second grating) for the Fourier transform become finer vertical fringes in comparison with those denoted by reference symbol B2 of FIG. 25. As shown by reference symbol B4 of FIG. 25, an image obtained by performing the Fourier transform for the moire image for the Fourier trans form becomes an image in which the zero-ary component and the primary component are arrayed horizontally.

As shown by reference symbol C1 of FIG. 26, in the case where the grating orientations of the multi-slit 12, the first grating 14 and the second grating 15 are diagonal at 45°, fringes of the moire image (an image obtained by slightly tilting the second grating with respect to the first grating 14) become diagonal at 45° (diagonal in a direction reverse to the slit direction) as shown by reference symbol C2 of FIG. 26. As shown by reference symbol C3 of FIG. 26, fringes of the moire image (an image obtained by further tilting the second grating) for the Fourier transform become finer diagonal fringes in the same direction as that denoted by reference symbol C2 of FIG. 26. As shown by reference symbol C4 of FIG. 26, an image obtained by performing the Fourier transform for the moire image for the Fourier transform becomes an image in which the zero-ary component and the primary component are arrayed diagonally at 45° in a reverse direction to the fringe direction.

Figure 27:
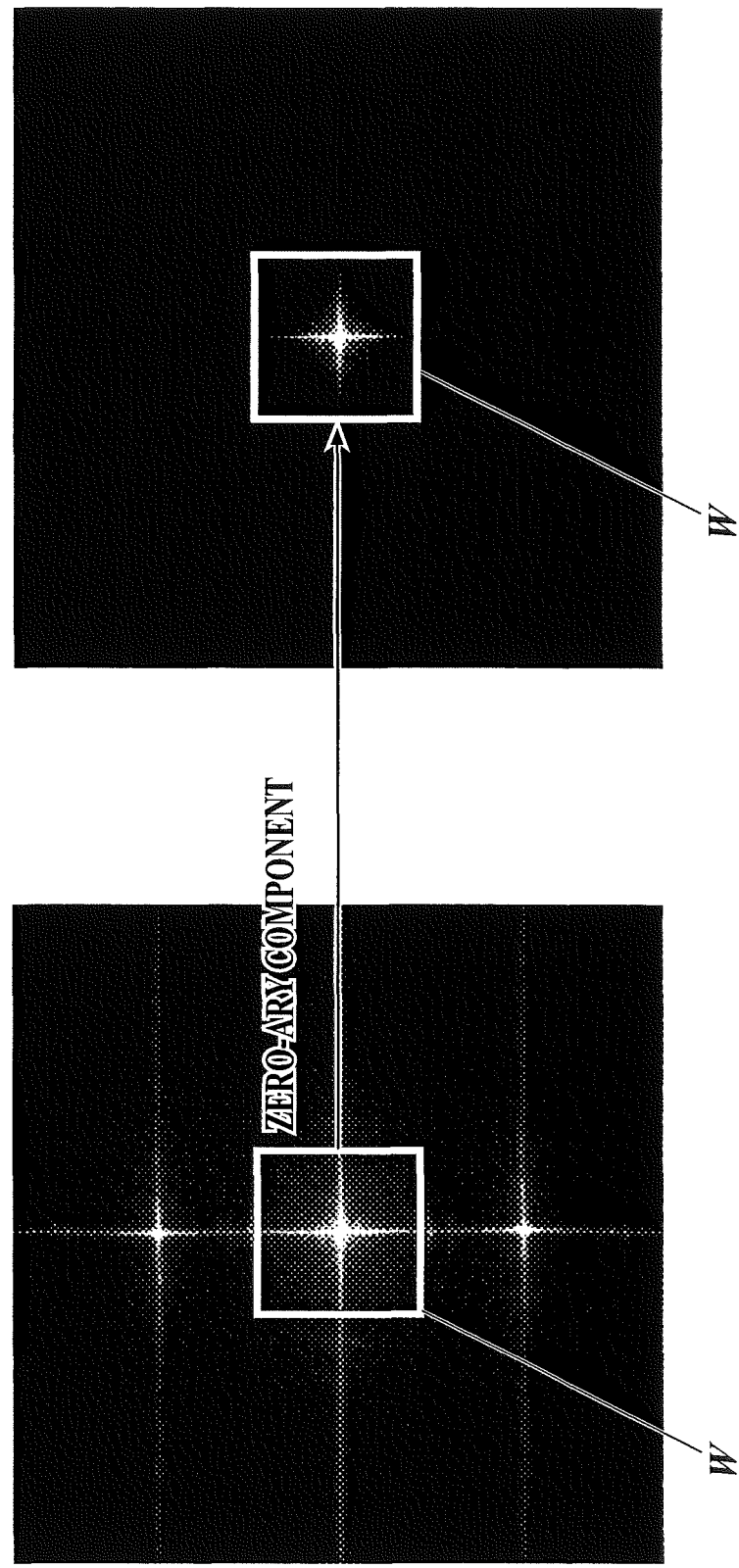
FIG. 27 is a view showing an example where a zero-ary component obtained by performing the Fourier transform is cut out by a Hanning window.

Subsequently, in each image (each of the image with the subject and the image without the subject) obtained by the Fourier transform, the zero-ary component is cut out by a Hanning window W shown in FIG. 27 (Step S36). The zero-ary component is cut out by the Hanning window W, whereby a peripheral portion of the Hanning window W is dropped to zero, and a center portion of the Hanning window W is passed as it is.

Figure 28:
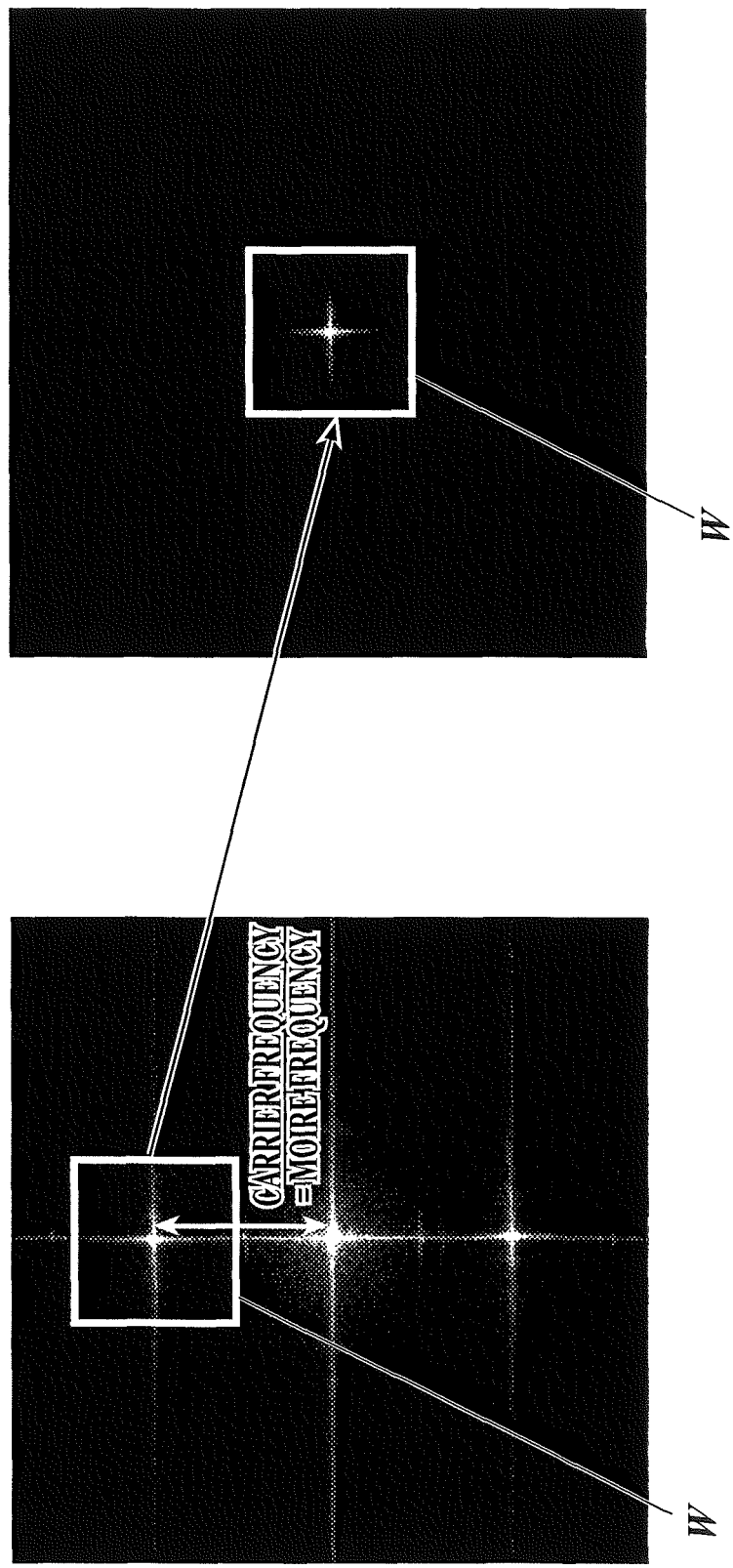
FIG. 28 is a view showing an example where a primary component obtained by the Fourier transform is shifted by an amount of a carrier frequency and is cut out by the Hanning window.

Subsequently, in the image obtained by the Fourier transform, as shown in FIG. 28, the primary component is shifted by a carrier frequency (=moire frequency), and is cut out by the Hanning window W (Step S37). A window function for such cutout is not limited to the Hanning window, and a Hamming window, a Gaussian window and the like may be used in response to the purpose.

Subsequently, each of the zero-ary component and the primary component, which are cut out, is subjected to inverse Fourier transform (Step S38).

When the inverse Fourier transform is ended, creation of each of the reconstructed images with the subject and without the subject is performed by using the zero-ary component and the primary component, which are subjected to the inverse Fourier transform (Step S39 to Step S41). Specifically, an absorption image is created from amplitude of the zero-ary component (Step S39). Moreover, a differential phase image is created from a phase of the primary component (Step S40). Furthermore, a small-angle scattering image is created from an amplitude ratio (=Visibility) of the zero-ary component and the primary component (Step S41).

Subsequently, correction processing for removing the phases of the interference fringes from the reconstructed image with the subject and removing image non-uniformity (artifact) therefrom is performed by using the reconstructed image without the subject (Step S42). The processing of Step S42 is similar to that described in Step S21 of FIG. 14B, and accordingly, a description thereof is incorporated by reference.

Figure 29:
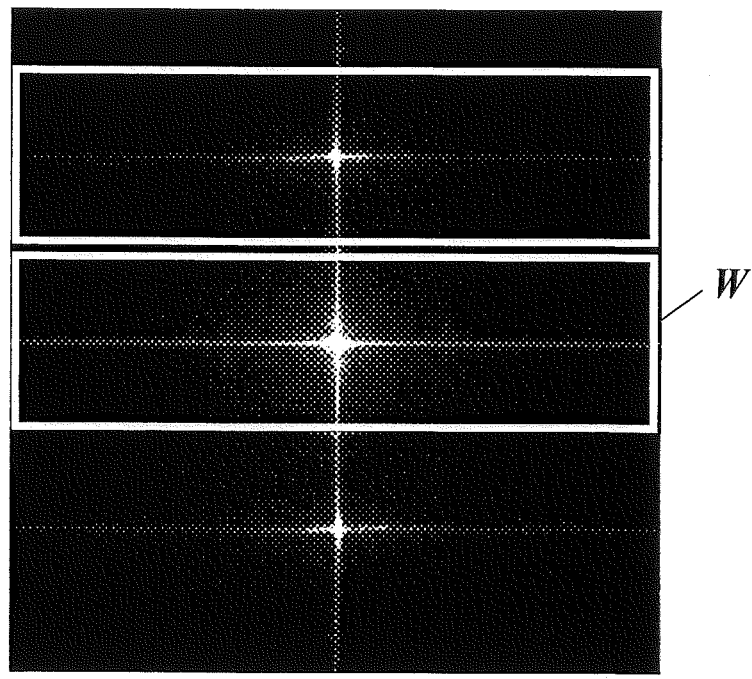
FIG. 29 is a view showing an example of a window in an improved Fourier transform method.

Note that, in the above-mentioned conventional Fourier transform method, high-frequency components are discarded in both of the vertical and horizontal directions in the event of cutting out the zero-ary component and the primary component, and accordingly, the spatial resolution is deteriorated, and an image blurred as a whole is formed. Here, the inventors of this application have focused on that, in the case of using the one-dimensional grating as the X-ray grating, the information regarding the differential phase images and the small-angle scattering image of the Talbot interferometer and the Talbot-Lau interferometer is only in one direction perpendicular to the slit direction of the gratings (multi-slit 12, first grating 14, second grating 15). Then the inventors have found out that, if the window W for use in Steps S36 and S37 is formed not into a square of a conventional type but into a rectangle extended in the direction perpendicular to the slit direction of the gratings as shown in FIG. 29, then a high-frequency component of the signal in the direction where the image information is included, the direction being perpendicular to the slit direction of the gratings, can be taken out so as not to be dropped, and the blur in the direction perpendicular to the slit direction of the gratings can be reduced (this is referred to as an improved Fourier transform method. The present invention has a feature in using the mater that the image information is not originally included in a direction parallel to the slit direction of the gratings, where the decrease of the spatial resolution is inevitable in theory, and at the time of twice imaging to be describe later, a great advantage is obtained with respect to the Fourier transform method using the two-dimensional grating (FIG. 29 shows an example of setting a rectangular window W for reference symbol A4 of FIG. 24).

Figure 30A:
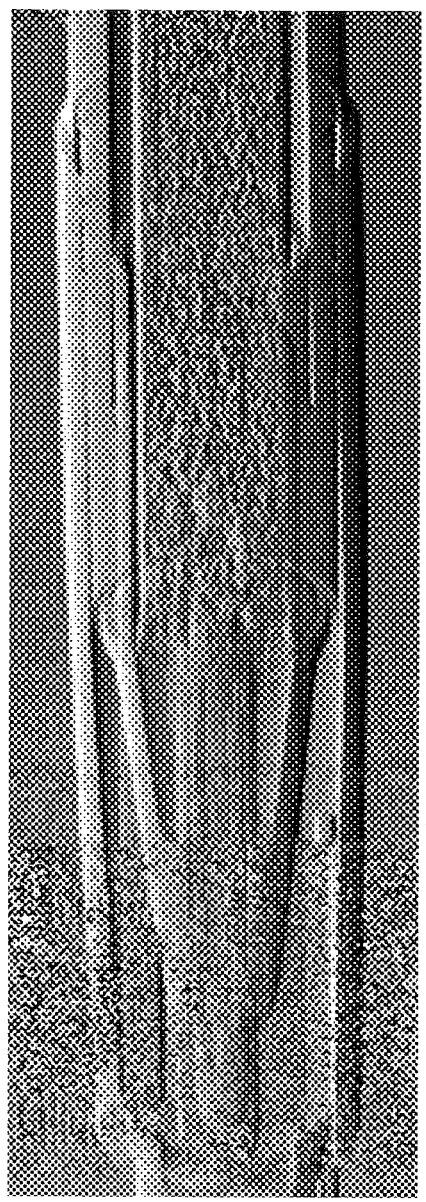
FIG. 30A is a view showing an example of a reconstructed image of the subject, the reconstructed image being obtained by the fringe scanning method.
Figure 30B:
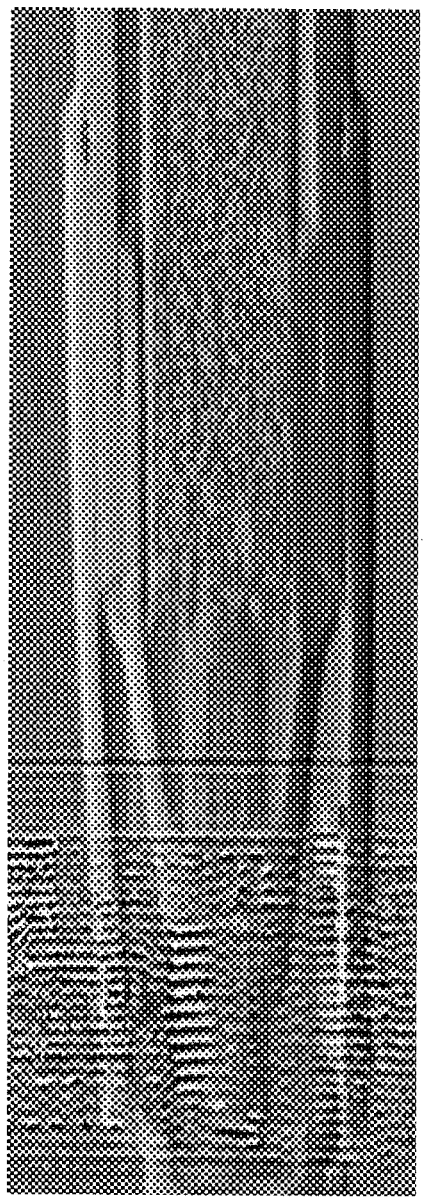
FIG. 30B is a view showing an example of a reconstructed image obtained by the improved Fourier transform method.
Figure 30C:
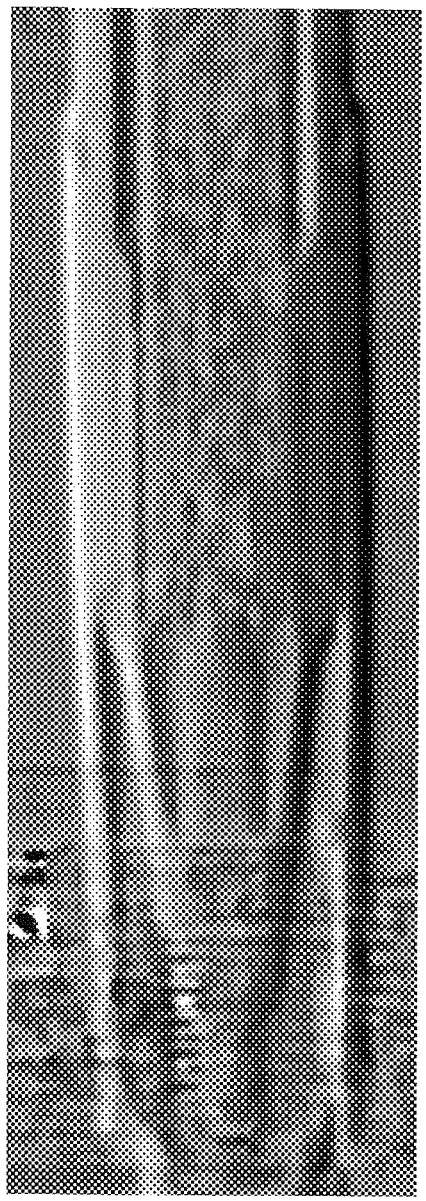
FIG. 30C is a view showing an example of a reconstructed image obtained by a conventional Fourier transform method.

FIG. 30A shows an example of the reconstructed image of the subject, which is obtained by the fringe scanning method. FIG. 30B shows an example of the reconstructed image, which is obtained by the improved Fourier transform method. FIG. 30C shows an example of the reconstructed image, which is obtained by the conventional Fourier transform method. The reconstructed images of FIG. 30A to FIG. 30C are differential phase images obtained by being imaged while setting the slit direction of the gratins to the vertical direction. As shown in FIG. 30A, in the image obtained by the fringe scanning method, the blur is small both in the vertical direction and the lateral direction. As shown in FIG. 30B, the image obtained by the improved Fourier transform method is blurred only in the vertical direction, and is not blurred in the horizontal direction. As shown in FIG. 30C, the image obtained by the conventional Fourier transform method is blurred both in the vertical direction and the horizontal direction.

Note that, though the differential phase images are shown in FIG. 30A to FIG. 30C, the directions of the blur according to the respective methods are similar also in the absorption images and the small-angle scattering images.

As described above, in the improved Fourier transform method, only the signal component in the direction parallel to the slit direction of the gratings is blurred. Accordingly, the first imaging is performed by arranging the subject so that a longitudinal direction thereof can be the direction perpendicular to the slit direction of the gratings, thereafter, the second imaging is performed by rotating the subject or the gratings so that the relative angle therebetween can be 90°, the reconstructed images are individually created from the moire images obtained individual at the first imaging and the second imaging, and the two reconstructed image thus created are synthesized with each other, and in such a way, a two-dimensional image of the subject, in which the blur is small in both of the vertical direction and the horizontal direction, can be obtained (in the case of the differential phase images and the small-angle scattering image).

It is also possible to perform the imaging by the Fourier transform method by using the two-dimensional grating. However, since the primary components exist both vertically and horizontally, the window W for the cutout is restricted to a range that is narrow both vertically and horizontally. Therefore, it is inevitable that the spatial resolution is largely decreased. Meanwhile, in accordance with this method, it becomes possible to create the two-dimensional image by using the one-dimensional grating without largely decreasing the resolution. Note that, in the synthesis image that is based on the imaging in two directions, subject information on four corners thereof is chipped off; however, in the radiography in the medical field, it is generally frequent that the region of interest of the subject is placed at the center portion of the imaging region. Accordingly, it is less likely that the above-described chip-off of the subject is regarded as a problem. Moreover, the number of times of the imaging itself is saved to be twice, and accordingly, it is also possible to suppress an influence of a body motion of the subject.

Note that, in the event of changing the imaging direction (that is, changing the slit direction with respect to the subject), it is necessary to simultaneously rotate the multi-slit 12, the first grating 14 and the second grating 15 by 90° in a similar way to the fringe scanning method.

In the case where the first imaging and the second imaging are performed while changing the relative angle between the first grating 14 and the second grating 15 by 90°, the control unit 51 of the controller 5 executes the reconstructed image creation/display processing according to the Fourier transform method, which is shown in FIG. 21, for each of the first imaged image and the second imaged image, and thereafter, synthesizes the two images with each other. Note that, in the case where, between the first image and the second image, the same portion of the subject is not rendered on the same pixel (that is, in the case where the subject is deformed or moved), either one of the images is moved in parallel or rotationally, and both of the images are positionally aligned at positions where an error therebetween becomes minimum, and thereafter, both of the images are synthesized with each other. As a synthesis method, a variety of method can be used. For example, it is defined that the pixel of the first imaged image is f1 (x, y), that the pixel of the second imaged image is f2 (x, y), and that the pixel of the synthesis image is g (x, y). Then, in each pixel, the following calculation is performed (a square root of a sum of squares is taken), and an average value of power is taken:

$g(x,y)=\sqrt{(f1(x,y)^2+f2(x,y)^2)}$

Moreover, color display may be performed, for example, in such a manner that the first imaged image is displayed red, and that the second imaged image is displayed blue.

Incidentally, as understood from the images of FIG. 30A to FIG. 30C, the reconstructed image obtained by the fringe scanning method is sharper and less blurred than the reconstructed images obtained by the Fourier transform methods. However, in the imaging for the fringe scanning method, plural pieces of the images are continuously taken, and accordingly, the imaging time becomes long (approximately one minute) in response to the capturing time of the detector, the processing time before and after the X-ray exposure, the mechanism operation time, and the like, and therefore, the body motion is likely to occur. As opposed to this, in such a Fourier transform method, one image is imaged in the single imaging. Accordingly, the imaging time depends only on the exposure time of the X-ray, and can be suppressed to approximately five seconds. Therefore, an effect of suppressing the body motion can be expected. Moreover, in the improved Fourier transform method, the deterioration of the spatial resolution is suppressed to be small. Hence, both of the fringe scanning method and the Fourier transform method are used in combination, for example, in the following manner: (1) the fringe scanning method is used in the case where it is possible to fix the subject. and the Fourier transform method is used in the case where it is desired that the body motion be suppressed; (2) the Fourier transform method is used in a simple test, and the fringe scanning method is used in a more detailed (precise) test. In such a way, it becomes possible to obtain an image corresponding to the purpose, and to perform imaging in which a load on the patient is small and the number of re-imaging times is small. In this embodiment, the relative angle between the first grating 14 and second grating 15 can be adjusted with ease, and the imaging for the fringe scanning method and the imaging for the Fourier transform method can be switched, and accordingly, it becomes possible to perform the optimum imaging corresponding to the purpose of the imaging.

Returning to FIG. 21, the created reconstructed image is displayed on the display unit 53 (Step S43).

In Step S43, the reconstructed image is displayed by a similar display method to that described in Step S22 of FIG. 14B. That is to say, as shown in FIG. 19, two types or more of images among the absorption image, the differential phase image and the small-angle scattering image are displayed at the same position of the display unit 53 while being sequentially switched at every predetermined time.

As mentioned above, two types or more of the images to be displayed are created by the different pieces of processing from the imaged images (moire images) obtained by the single imaging set. Accordingly, as shown in FIG. 18A to FIG. 18C, the positions of the subject in the three images are the same, and the three images individually represent information of different features in the subject. Hence, as shown in FIG. 19, if the three images are displayed on the same position of the display unit 53 while being sequentially switched at every predetermined time, then it is unnecessary for the physician who performs the interpretation to move the line of sight thereof, and a fatigue is not induced. Accordingly, the physician can perform the interpretation while maintaining a high degree of concentration. Moreover, by an afterimage effect (a so-called subliminal effect) in the event where the images are switched at every predetermined time, the physician becomes capable of reconstructing the plural pieces of information (features) regarding the subject in his/her brain, and becomes capable of carrying out the highly accurate diagnosis.

Moreover, in a similar way to Step S22, also in Step S43 of FIG. 21, in addition to the reconstructed images for the diagnosis obtained by the imaging performed this time, reference images may be displayed in combination. For example, as shown in FIG. 31, first, two types or more of the diagnostic images are circularly displayed on a region R1 while being sequentially switched at every predetermined time. When a shift to the next display is instructed from the operation unit 52, the reference images of the same type as that of the displayed diagnostic image are circularly displayed on a region R2 while being sequentially switched at every predetermined time. The reference images are images which the physician refers to in the event of interpreting the diagnostic images, and for example, are a reconstructed image by the Fourier transform method, which is imaged previously with regard to the same imaged region of the same patient, and a reconstructed image by the Fourier transform method with regard to a typical case. The circular display of the reference images may be performed before the circular display of the diagnostic images.

Note that, as mentioned above, the reconstructed image by the fringe scanning method is sharper and less blurred than the reconstructed images by the Fourier transform method. Hence, in the case where the reference image of the reconstructed image by the fringe scanning method exists in the storage unit 55, then as shown in FIG. 31, preferably, the reference image by the fringe scanning method is circularly displayed in response to the operation from the operation unit 52. Moreover, preferably, in response to the instruction from the operation unit 52, the same type of the diagnostic image and the same type of the reference image according to the fringe scanning method (for example, the reference image is a reference image as the absorption image according to the fringe scanning method when the absorption image is displayed as the diagnostic image) are arrayed and displayed on the regions R1 and R2 while being sequentially switched. In this case, the type of images to be displayed may be switched in response to a switching instruction from the operation unit 52. Moreover, the same types of images may be arrayed left and right, and all the types of images may be displayed on one screen.

Here, in the above-described absorption image, differential phase image and small-angle scattering image, which are created and displayed in the X-ray imaging apparatus 1 and the controller 5, the positions of the subject are the same thereamong, and these three images individually represent the information of the different features in the subject. Hence, for example, these images are applied to a subject region such as the mamma in which it has been difficult to grasp the feature of the lesion by the conventional interpretation using only the absorption image, whereby the diagnostic accuracy can be enhanced to a great extent.

On the absorption image, information regarding a large structural change appears. On the differential phase image, information regarding a phase change of a margin of a tissue appears. On the small-angle scattering image, information regarding scattering in the tissue appears. Hence, in the case of treating the mamma as the subject, then on the absorption image, there appears information regarding distributions of the mammary gland and the fat in the entire mamma, a tumor or a cancer with a clear margin, and the like. On the differential phase image, there appears information regarding tissue calcification, spicula, such tumor/cancer, an architectural distortion of the mammary gland, and the like. In the tumor/cancer and the architectural distortion, there are those where the spicula exist and the spicula do not exist. On the small-angle scattering image, there appears information regarding the architectural distortion of the mammary gland, the tumor/cancer, the spicula and the like. Hence, the absorption image, the small-angle scattering image (differential phase image) and the differential phase image (small-angle scattering image) are sequentially displayed on the display unit 53 while being switched in this order, whereby it becomes possible to carry out a highly accurate diagnosis in which pieces of the information on the respective images are integrated with one another.

For example, while a tumor/cancer existing on the fat has a clear margin, a tumor/cancer existing on the mammary gland has an unclear margin. Accordingly, first, the distributions of the mammary gland and the fat in the entire mamma are grasped in advance by the absorption image, and next, the image is switched to the differential phase image and the small-angle scattering image, and it is confirmed whether or not there is a shadow of the tumor/cancer by the differential phase image and the small-angle scattering image while being conscious of a region of the mammary gland grasped by the absorption image, whereby the detection accuracy of the tumor/cancer with the unclear margin can be enhanced.

As described above, with regard to the absorption image, which has been heretofore used for the diagnosis, and is familiar to the physician him/herself, a primary diagnosis that is based on the diagnostic resolution cultivated by each physician through a diagnosis for long is carried out, and thereafter, the differential phase image and/or the small-angle scattering image is displayed, and re-interpretation that is based on the image concerned is carried out, whereby the physician him/herself becomes capable of revising a result of the primary diagnosis as to whether or not there is an abnormal shadow and whether the abnormal shadow exhibits benignity or malignancy. Moreover, when the interpretation of the absorption image is carried out one more time after the interpretation of the differential phase image and/or the small-angle scattering image, then the physician gradually becomes capable of visually recognizing the abnormal shadow, a difference between the benignity and the malignancy, and the like, which have been invisible at the beginning. By repeating this diagnosis method, the physician will finally establish a new and enhanced diagnostic resolution, and will become capable of carrying out a diagnosis with higher accuracy even in a diagnosis that is based only on the absorption image, and this is preferable.

Moreover, it is said to be highly possible that the tumor/cancer may be malignant in the case of involving the spicula. Accordingly, first, by the absorption image, it is confirmed whether or not there is a large tumor/cancer, and next, the image is switched to the small-angle scattering image, and it is confirmed whether or not there are peripheral spicula present on the periphery of the large tumor/cancer grasped by the absorption image, or single spicula free from the tumor/cancer, whereby detection accuracy of the tumor/cancer and the spicula, which have a high possibility to be malignant, can be enhanced. Moreover, it is confirmed whether or not there is a shadow of the tumor/cancer by the small-angle scattering image, next, the image is switched to the differential phase image, and it is conformed whether or not there are peripheral spicula present on the periphery of the large tumor/cancer grasped by the small-angle scattering image, or single spicula, whereby the detection accuracy of the tumor/cancer and the spicula, which have a high possibility to be malignant, can be enhanced.

Moreover, the controller 5 is given an abnormal shadow candidate detection function (CAD (Computer-Aided Diagnosis) function), candidates for the abnormal shadow are detected individually from the absorption image, the differential phase image and the small-angle scattering image, and the respective images and detection results (referred to as CAD results) of such abnormal shadow candidates in the respective images are displayed while being switched, whereby detection accuracy of the abnormality shadow candidates can be enhanced. The CAD function is realized by cooperation between the control unit 51 of the controller 5 and an abnormal shadow candidate detection program stored in the storage unit 55. Moreover, on the display unit 53, the respective images are displayed at the same position (region R0), and the CAD results are displayed on a CAD result column R4 (refer to FIGS. 32A and 32B).

Here, the absorption image has been heretofore used as the mammogram for the diagnosis, and such detection processing for the abnormal shadow candidates by the CAD has also been performed only for the absorption image. In detection algorithms for the abnormal shadow candidates, detection sensitivities thereof are various; however, in general, as such detection sensitivity is higher, a ratio of false positives also becomes large. Therefore, there have been problems that, in the case of using a detection algorithm with high detection sensitivity in order to eliminate overlook of true positives, the number of false positives is also increased, and that, in the case of using an algorithm with low detection sensitivity in order to reduce the number of false positives, the true positives are overlooked. Moreover, for example, even in lesions having the same spicula, depending on sizes and types of the lesions, there is a lesion from which more information appears better by the differential phase image, and there is a case where more information appears better by the small-angle scattering image. Accordingly, the detection of the abnormal shadow candidates is performed by the same detection algorithm individually for the absorption image, the differential phase image and the small-angle scattering image, which represent different features of the same subject, and the CAD results are displayed in combination at the time when the respective images in FIG. 19 and the like are displayed, whereby the physician becomes capable of comprehensively determining normality and abnormality by comparing the respective images with one another and the CAD detection results in the respective images with one another. Accordingly, such excessive pickup of the false positives, which is described above, and the overlook of the true positives, which is described above, can be reduced.

Figure 32A:
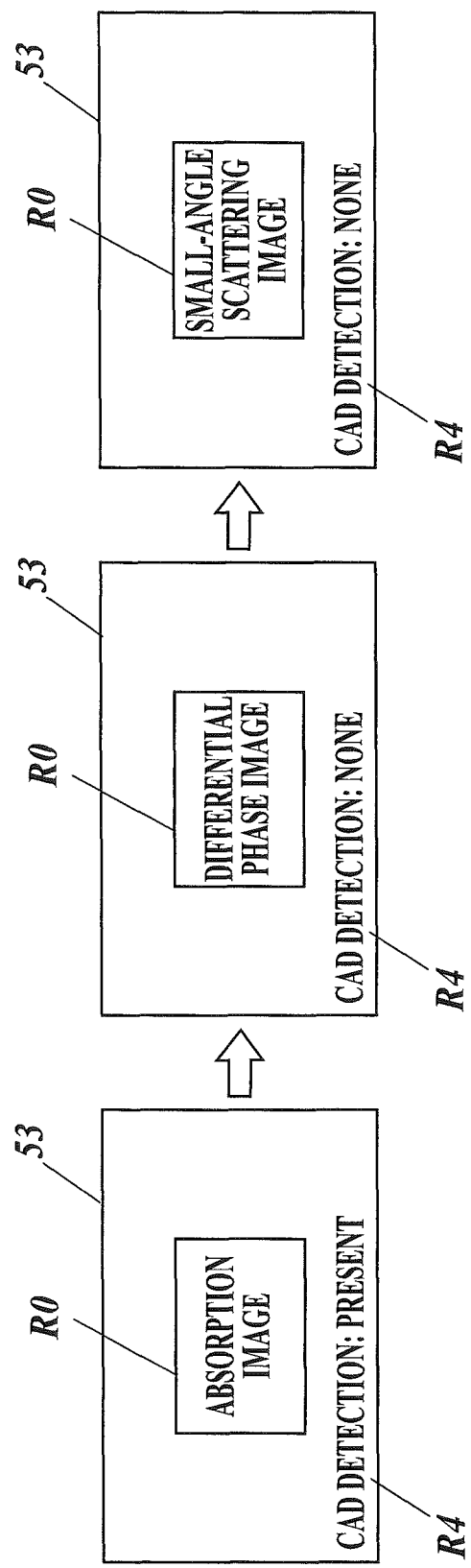
FIG. 32A is a view showing a display example of CAD results in a case where detection of candidates for an abnormal shadow is performed for a displayed image by a detection algorithm with high detection sensitivity.

For example, in the absorption image, in the case of carrying out the detection by a detection algorithm in which detection sensitivity is high (higher than standard), and displaying the respective images and the CAD detection results while switching the same, as shown in FIG. 32A, in the case where the detection result of the CAD in the absorption image is "there is CAD detection" and the detection result of the CAD in the differential phase image and/or the small-angle scattering image is "there is no CAD detection", it can be determined that it is highly possible that the CAD result may pick up the false positive. Accordingly, in the case of the display shown in FIG. 32A, first, the physician grasps the distributions of the mammary gland and the fat in the entire mamma as the subject by the absorption image, picks up a portion suspected to be abnormal. Subsequently, the physician switches the display to the differential phase image and/or the small-angle scattering image, and observes the portion suspected to be abnormal in the absorption image. In this case, if the portion concerned is confirmed to be normal, the portion concerned is determined to be the false positive, and can be deleted.

Figure 32B:
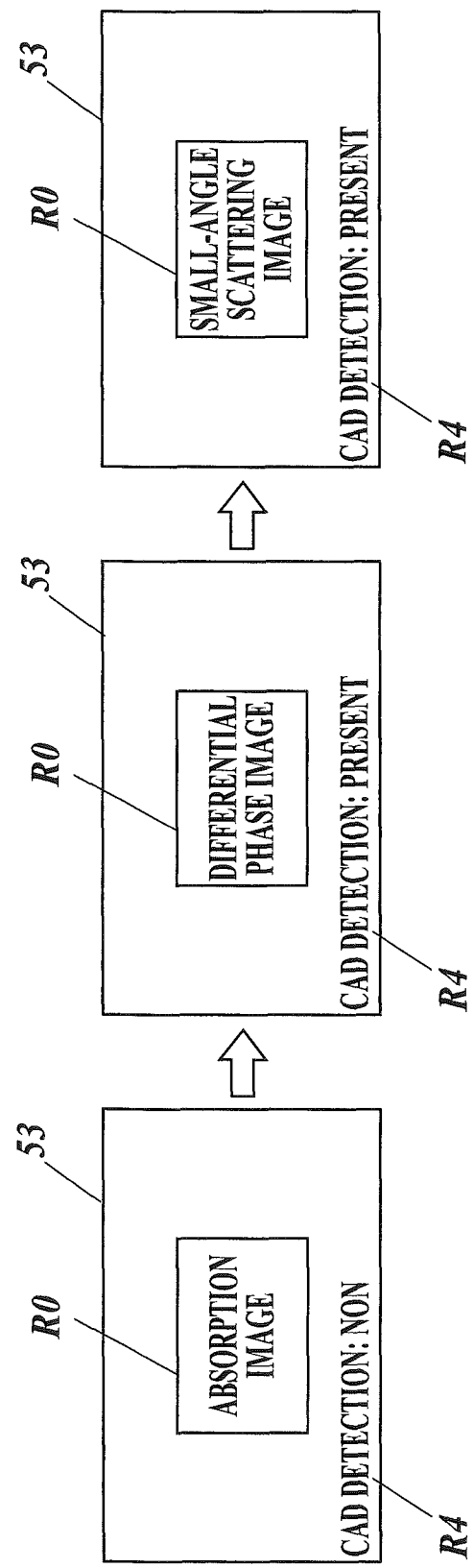
FIG. 32B is a view showing a display example of CAD results in a case where the detection of the candidates for the abnormal shadow is performed for the displayed image by a detection algorithm with low detection sensitivity.

Moreover, for example, in the absorption image, in the case of carrying out the detection by a detection algorithm in which detection sensitivity is low (lower than standard), and displaying the respective images and the CAD detection results while switching the same, as shown in FIG. 32B, in the case where the detection result of the CAD in the absorption image is "there is no CAD detection" and the detection result of the CAD in the differential phase image and/or the small-angle scattering image is "there is CAD detection", it is conceived possible that the true possible in the CAD may be overlooked. Accordingly, in the case of the display shown in FIG. 32B, first, the physician grasps the distributions of the mammary gland and the fat in the entire mamma as the subject by the absorption image, picks up a portion suspected to be abnormal. Subsequently, the physician switches the display to the differential phase image and/or the small-angle scattering image, and observes the portion suspected to be abnormal in the absorption image. In this case, if the portion concerned is confirmed to be abnormal, then the portion concerned can be diagnosed to be the abnormal shadow.

Figure 33A:
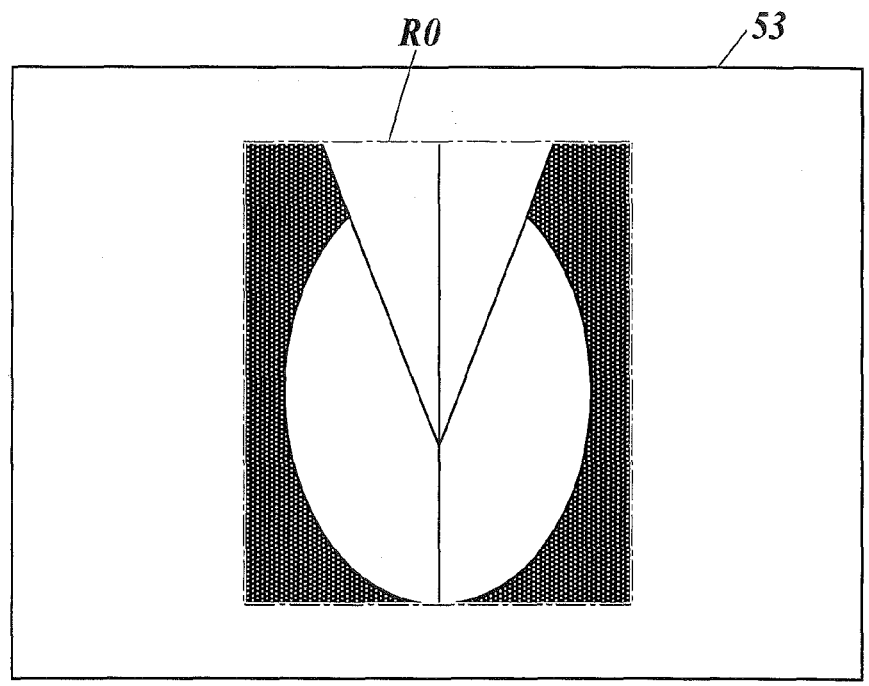
FIG. 33A is a view showing an example of a display mode of a mammogram.
Figure 33B:
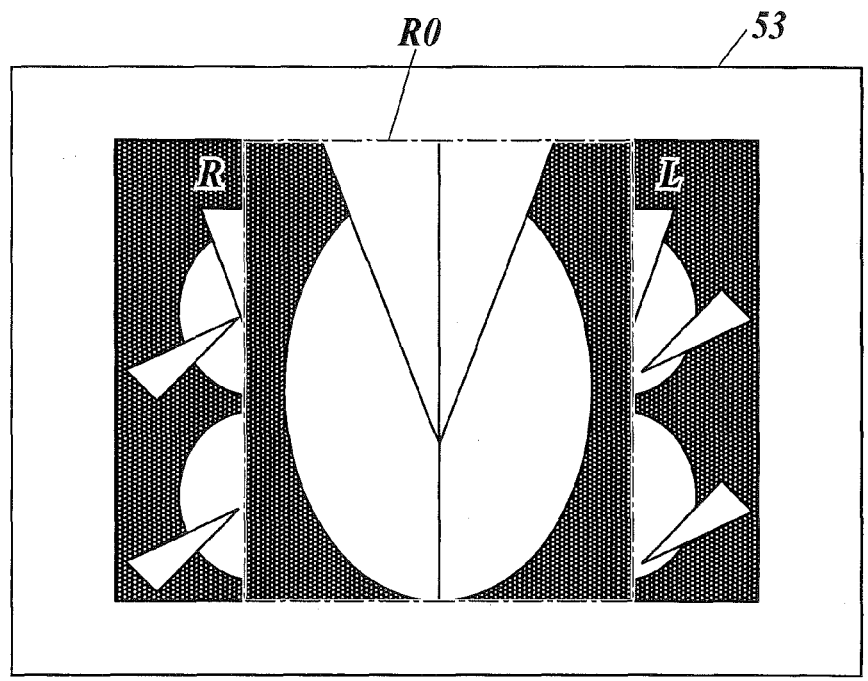
FIG. 33B is a view showing another example of the display mode of the mammogram.

Here, with regard to a display mode of the mammogram on the region R0, as shown in FIG. 33A, two images, which are a left mammogram and a right mammogram, may be displayed while bringing chest walls thereof into contact with each other. Alternatively, the left mammogram or the right mammogram may be displayed singly. Alternatively, the mammogram may be displayed as pairs of MLOs and CCs. Moreover, as shown in FIG. 33B, reduction images of the mammograms may be displayed outside of the region R0, and annotations may be displayed at positions of the abnormal shadow candidates detected by the CAD in the reduction images. In such a way, the positions of the abnormal shadow candidates detected by the CAD can be confirmed, and it becomes possible to observe the mammograms without being obstructed by the annotations.

As described above, in accordance with the medical image display system, the subject is imaged in the X-ray imaging apparatus 1 in accordance with the first imaging mode by the fringe scanning-type imaging apparatus or the second imaging mode by the Fourier transform-type imaging apparatus. In the controller 5, based on the moire images obtained by the imaging, at least two images of the X-ray absorption image, the differential phase image and the small-angle scattering image are created. Then, the at least two images thus created are displayed on the same position of the display unit 53 while being sequentially switched.

The three images, which are the absorption image, the differential phase image and the small-angle scattering image, which are created and displayed by the above-described medial image display system, are those created by different pieces of processing from the imaged images (moire images) obtained by the single imaging set. Accordingly, the positions of the subject in the three images are the same, and the three images individually have the information of different features in the subject. Hence, if the at least two images are displayed on the same position (region R0) of the display unit 53 while being sequentially switched at every predetermined time, then it is unnecessary for the physician who performs the interpretation to move the line of sight thereof, and the fatigue is not induced. Accordingly, the physician can perform the interpretation while maintaining a high degree of concentration. Moreover, by the afterimage effect (a so-called subliminal effect) in the event where the images are switched at every predetermined time, the physician becomes capable of reconstructing the plural pieces of information (features)

regarding the subject in his/her brain, and becomes capable of carrying out the highly accurate diagnosis.

Moreover, in the controller 5, the imaging is performed while mounting the subject on the subject platform, and in addition, the imaging is performed without mounting the subject on the subject platform. Then, based on the moire images with the subject, at least two images with the subject, from among the X-ray absorption image, the differential phase image and the small-angle scattering image, are created, and based on the moire images without the subject, at least two images without the subject, which are of the same types as those of the at least two images with the subject, are created. For the images with the subject, the correction such as the removal of the phases of the interference fringes and the removal of the image non-uniformity is performed by using the images without the subject. Hence, it becomes possible to provide the physician with the images free from the influence of the interference fringes and the non-uniformity.

Moreover, before or after the at least two created images are displayed on the same position of the display unit 53 while being sequentially switched, at least two reference images are displayed on the same position of the display unit 53 while being switched, the position being different from the position of the two images to be interpreted, whereby the diagnostic accuracy in the event of performing the diagnosis by using the reference images can be enhanced.

Note that the above-described embodiment is a preferred example of the present invention, and the present invention is not limited to this.

For example, in the above-described embodiment, the description is made of the example where the X-ray imaging apparatus 1 is configured as the Talbot-Lau interferometer, which includes the multi-slit, relatively moves the multi-slit with respect to the first grating and the second grating, and thereby creates the plurality of moire images for the fringe scanning method. However, the X-ray imaging apparatus 1 may be configured as a Talbot interferometer, which relatively moves the first grating and the second grating at a constant cycle interval, repeats the processing for allowing the radiation detector to read the image signals in response to the X-ray, which is irradiated by the X-ray source, every time when the first grating and the second grating move at the constant cycle interval, and thereby creates the plurality of moire images for the fringe scanning method. Then, an absorption image, a differential phase image and a small-angle scattering image, which are obtained by reconstructing the plurality of moire images created by the Talbot interferometer, may be displayed on the same position of the display unit 53 as mentioned above while being sequentially switched.

Moreover, in the above-described embodiment, the reconstructed images which are based on the one-dimensional image data imaged by the apparatus capable of both methods of the fringe scanning method and the Fourier transform method (including the improved type) are used; however, the present invention is not limited to this, and an apparatus dedicated to the Fourier transform method (including the improved type) may be used.

Furthermore, the present invention may be applied to reconstructed images which are based on two-dimensional image data imaged by an imaging apparatus dedicated for the Fourier transform method, which uses two-dimensional gratings as the first grating and the second grating, and by an imaging apparatus dedicated for the Fourier transform method, which further uses a multi-grating (two-dimensional grating) in combination in the vicinity of the focal position.

Moreover, in the above-described embodiment, the display method of the present invention is described by mentioning the example of displaying the absorption image, the differential phase image and the small-angle scattering image on the same position of the display unit 53 while sequentially switching the same; however, the display method of the present invention is not limited to this, and is applicable to the case of displaying a plurality of images created by implementing different types of image processing for the same imaged image.

Moreover, in the event of such switching display, in order that it can be visually recognized with ease that the image is switched, for example, chroma (color) of each display screen can be switched to a black monotone, a red monotone, a blue monotone, and the like.

Moreover, in the above-described embodiment, the X-ray source 11, the multi-slit 12, the subject platform 13, the first grating 14, the second grating 15 and the X-ray detector 16 are arranged in this order (this arrangement is hereinafter referred to as a first arrangement); however, even if an arrangement is made in order of the X-ray source 11, the multi-slit 12, the first grating 14, the subject platform 13, the second grating 15 and the X-ray detector 16 (this arrangement is hereinafter referred to as a second arrangement), it is possible to obtain the reconstructed images by moving the multi-slit 12 while keeping on fixing the first grating 14 and the second grating 15.

In the second arrangement, the center of the subject and the first grating 14 are separated from each other by the thickness of the subject, and this second arrangement is a little inferior to the arrangement of the above-described embodiment in terms of the sensitivity. However, meanwhile, in consideration of the reduction of the exposure dose to the subject, the arrangement concerned utilizes the X-ray more effectively by the absorption amount of the X-ray in the first grating 14.

Moreover, an effective spatial resolution at the position of the subject depends on the focal point diameter of the X-ray, the spatial resolution of the detector, the magnification of the subject, the thickness of the subject, and the like; however, in the case where the spatial resolution of the detector in the above-described embodiment is 120 μm (half width of Gaussian approximation) or less, the effective spatial resolution becomes smaller in the second arrangement that in the first embodiment. Preferably, the arrangement order of the first grating 14 and the subject platform 13 is decided in consideration of the sensitivity, the spatial resolution, the X-ray absorption in the first grating 14 and the like.

Moreover, the order of imaging the image with the subject and the image without the subject is not limited to the above-described embodiment, and either thereof may take first. The same is also applied to the order of the creation of the reconstructed image with the subject and the creation of the reconstructed image without the subject.

Besides the above, detailed configurations and detailed operations of the respective devices which compose the medical image display system are also changeable as appropriate within the scope without departing from the spirit of the invention.

Note that the entire disclosure of Japanese Patent Application No. 2010-219031 filed on Sep. 29, 2010, which includes the description, the scope of claims, the drawings and the abstract, are incorporated herein by reference in its entirety.

INDUSTRIAL APPLICABILITY

This invention is applicable to a medical image display system that displays the X-ray image in the medical field.

Explanation of Reference Numerals
1 X-RAY IMAGING APPARATUS
11 X-RAY SOURCE
12 MULTI-SLIT
12a RACK
12b HOLDER
121 MULTI-SLIT ROTATING UNIT
121a MOTOR UNIT
121b GEAR UNIT
121c GEAR UNIT
121d GEAR SUPPORT PORTION
121e OPENING PORTION
122 DRIVE UNIT
122a MOTOR UNIT
122b GEAR UNIT
122c PINION
13 SUBJECT PLATFORM
130 SUBJECT HOLDER
131 ELLIPSOIDAL SHAPE
133 FINGER SPACER
14 FIRST GRATING
140 GRATING PORTION
141 FIRST HOLDER PORTION
142 SECOND HOLDER PORTION
142a PROTRUDING PORTION
15 SECOND GRATING
150 GRATING PORTION
151 HOLDER PORTION
16 X-RAY DETECTOR
17 HOLDING PORTION
17a CUSHIONING MEMBER
171a OPENING PORTION
171b TRAY FIXING MEMBER
18 MAIN BODY SECTION
181 CONTROL UNIT
182 OPERATION UNIT
183 DISPLAY UNIT
184 COMMUNICATION UNIT
185 STORAGE UNIT
18a DRIVE UNIT
210 GRATING ROTATING UNIT
211 HANDLE
212 ROTATING TRAY
212a OPENING PORTION
212b TO 212e RECESSED PORTION
213 RELATIVE ANGLE ADJUSTING UNIT
213a MOTOR UNIT
213b FIRST GEAR
213c SECOND GEAR
213d LEVER
214 STOPPER
5 CONTROLLER
51 CONTROL UNIT
52 OPERATION UNIT
53 DISPLAY UNIT
54 COMMUNICATION UNIT
55 STORAGE UNIT

The invention claimed is:

1. A medical image display method comprising:
an imaging step of imaging a subject by a fringe scanning-type imaging apparatus or a Fourier transform-type imaging apparatus, the apparatus including an X-ray source that irradiates an X-ray, a first grating and a second grating, each of which being arrayed in a direction perpendicular to an irradiation axis direction of the X-ray, a subject platform, and an X-ray detector in which conversion elements generating electric signals in response to the irradiated X-ray are arranged two-dimensionally, the X-ray detector reading, as image signals, the electric signals generated by the conversion elements;
an image processing step of creating an X-ray absorption image, a differential phase image and a small-angle scattering image by an image processing unit based on the image signals of the subject, the imaging signals being obtained in the imaging step;
a first displaying step of displaying the X-ray absorption image created in the image processing step;
a second displaying step of displaying at least one of the differential phase image and the small-angle scattering image created in the image processing step on the same position of a display unit while sequentially switching the X-ray absorption image and the at least one of the images; and
a third displaying step of displaying the other one of the differential phase image and the small-angle scattering image created in the image processing step on the same position of the display unit while sequentially switching the at least one of the images and the other one of the images.

2. The medical image display method of claim 1, further comprising a step of performing abnormal shadow extraction processing for the at least one of the images created in the image processing step, wherein
when an image which is subjected to the abnormal shadow extraction processing is displayed, an abnormal shadow extraction processing result is displayed together with the image.

3. The medical image display method of claim 1, further comprising a step of performing abnormal shadow extraction processing in the same algorithm for each image created in the image processing step, wherein
an abnormal shadow extraction processing result is displayed together with each image.

* * * * *